(12) United States Patent
Neamati et al.

(10) Patent No.: US 11,214,567 B2
(45) Date of Patent: Jan. 4, 2022

(54) SMALL MOLECULE INHIBITORS OF MYC AND USES THEREOF

(71) Applicants: The Regents of the University of Michigan, Ann Arbor, MI (US); YUNNAN UNIVERSITY, Yunnan (CN)

(72) Inventors: Nouri Neamati, Ann Arbor, MI (US); Yi Jin, Kunming (CN); Jun Lin, Kunming (CN)

(73) Assignees: The Regents of the University of Michigan, Ann Arbor, MI (US); YUNNAN UNIVERSITY, Yunnan (CN)

( * ) Notice: Subject to any disclaimer, the term of this patent is extended or adjusted under 35 U.S.C. 154(b) by 2 days.

(21) Appl. No.: 16/641,130

(22) PCT Filed: Aug. 23, 2018

(86) PCT No.: PCT/US2018/047711
§ 371 (c)(1),
(2) Date: Feb. 21, 2020

(87) PCT Pub. No.: WO2019/040724
PCT Pub. Date: Feb. 28, 2019

(65) Prior Publication Data
US 2020/0172528 A1 Jun. 4, 2020

Related U.S. Application Data

(60) Provisional application No. 62/549,237, filed on Aug. 23, 2017.

(51) Int. Cl.
*C07D 413/10* (2006.01)
*C07D 413/14* (2006.01)
*A61K 45/00* (2006.01)

(52) U.S. Cl.
CPC ......... *C07D 413/10* (2013.01); *C07D 413/14* (2013.01); *A61K 45/00* (2013.01)

(58) Field of Classification Search
CPC ..... C07D 413/10; C07D 413/14; A61K 45/00
USPC ....................................................... 514/314
See application file for complete search history.

(56) References Cited

PUBLICATIONS

Jiang et al., Tautomeric-Dependent Lactam Cycloaddition with Nitrile Oxide: Facile Synthesis of 1,2,4-Oxadiazole[4,5-a]indolone Derivatives, 2017, ACS Omega, 2, 3123-3134 (Year: 2017).*
Amati, B. et al., Oncogenic activity of the c-Myc protein requires dimerization with Max. Cell. Jan. 29, 1993;72(2):233-45.
Berg, T.; et al., Small-molecule antagonists of Myc/Max dimerization inhibit Myc-induced transformation of chicken embryo fibroblasts. Proc Natl Acad Sci U S A. Mar. 19, 2002;99(6):3830-5.
Chen, B.-J.; et al., Small molecules targeting c-Myc oncogene: promising anti-cancer therapeutics. Int J Biol Sci. Sep. 13, 2014; 10(10): 1084-96.
Efferth, T.; et al., Molecular target-guided tumor therapy with natural products derived from traditional Chinese medicine. Curr Med Chem. 2007; 14(19):2024-32.
Felsher, D. W. Myc Inactivation Elicits Oncogene Addiction through Both Tumor Cell-Intrinsic and Host-Dependent Mechanisms. Genes Cancer. Jun. 2010; 1(6):597-604.
Halder, K.; et al., Quadruplex-duplex competition in the nuclease hypersensitive element of human c-myc promoter: C to T mutation in C-rich strand enhances duplex association. Biochem Biophys Res Commun. Feb. 4, 2005;327(1):49-56.
Kerwin, S. M.; et al., Perylene diimide G-quadruplex DNA binding selectivity is mediated by ligand aggregation. Bioorg Med Chern Lett. Feb. 11, 2002;12(3):447-50.
Lee, H.-M.; et al., Identification of natural product fonsecin B as a stabilizing ligand of c-myc G-quadruplex DNA by high-throughput virtual screening. Chem Commun (Camb). Jul. 14, 2010;46(26):4680-2.
Li, Q.; et al., Searching drug-like anti-cancer compound(s) based on G-quadruplex ligands. Curr Pharm Des. 2012; 18(14): 1973-83.
Luscher, B.; et al., Regulation of gene transcription by the oncoprotein MYC. Gene. Feb. 25, 2012;494(2): 145-60.
Ma, D.-L.; et al., Discovery of a natural product-like c-myc G-quadruplex DNA groove-binder by molecular docking. PLoS One. 2012;7(8):e43278.
McKeown, M. R.; Bradner, J. E. Therapeutic Strategies to Inhibit MYC. Cold Spring Harbor Perspectives in Medicine Oct. 1, 2014;4(10):a014266.
Mo, H.; et al., Identification of small molecules that induce apoptosis in a Myc-dependent manner and inhibit Myc-driven transformation. Proc Natl Acad Sci U S A. Apr. 18, 2006;103(16):6344-9.
Nasiri, H. R.; et al., Targeting a c-MYC G-quadruplex DNA with a fragment library. Chem Commun (Camb). Feb. 18, 2014;50(14):1704-7.
Ou, T.-M.; et al., Stabilization of G-quadruplex DNA and down-regulation of oncogene c-myc by quindoline derivatives. J Med Chem. Apr. 5, 2007; 50(7): 1465-74.
Ou, T.-M.; et al., Inhibition of cell proliferation by quindoline derivative (SYUIQ-05) through its preferential interaction with c-myc promoter G-quadruplex. Journal of Medicinal Chemistry 2011, 54, 5671-5679.
Pivetta, C.; et al., Perylene side chains modulate G-quadruplex conformation in biologically relevant DNA sequences. Bioorg Med Chem. Oct. 15, 2008;16(20):9331-9.

(Continued)

*Primary Examiner* — Kristin A Vajda
(74) *Attorney, Agent, or Firm* — Casimir Jones, S.C.; Robert A. Goetz

(57) ABSTRACT

This invention is in the field of medicinal chemistry. In particular, the invention relates to a new class of small-molecules having an oxadiazole-oxadiazolone structure (e.g., oxadiazole-phenyl-oxadiazolone compounds, oxadiazole-pyridine-oxadiazolone compounds, oxadiazole-indole-oxadiazolone compounds, oxadiazole-quinoline-oxadiazolone compounds, oxadiazole-pyrrole-oxadiazolone compounds, and oxadiazole-vinyl-oxadiazolone compounds), and their use as therapeutics for the treatment of cancer and other diseases.

13 Claims, 28 Drawing Sheets

(56) References Cited

PUBLICATIONS

Shin-Ya, K.; et al., Telomestatin, a novel telomerase inhibitor from *Streptomyces anulatus*. J Am Chem Soc. Feb. 14, 2001; 123(6): 1262-3.

Sun, D.; et al., Facilitation of a structural transition in the polypurine/polypyrimidine tract within the proximal promoter region of the human VEGF gene by the presence of potassium and G-quadruplex-interactive agents. Nucleic Acids Res. Oct. 25, 2005;33(18):6070-80.

Verdun, R. E.; et al., Replication and protection of telomeres. Nature. Jun. 21, 2007;447(7147):924-31.

Wang, H.; et al., Improved low molecular weight Myc-Max inhibitors. Mol Cancer Ther. Sep. 2007;6(9):2399-408.

Wang, J.; et al., A Pt(II)-Dip complex stabilizes parallel c-myc G-quadruplex. Chem Commun (Camb). May 25, 2013;49(42):4758-60.

Zhang, J.; et al., Recent progress and future potential for metal complexes as anticancer drugs targeting G-quadruplex DNA. Curr Med Chem. 2012;19(18):2957-75.

\* cited by examiner

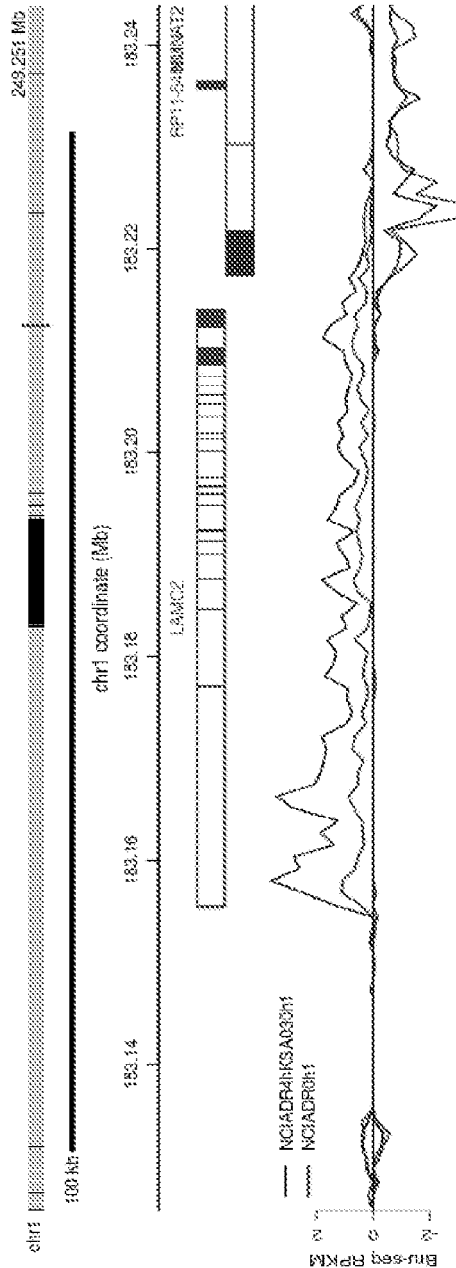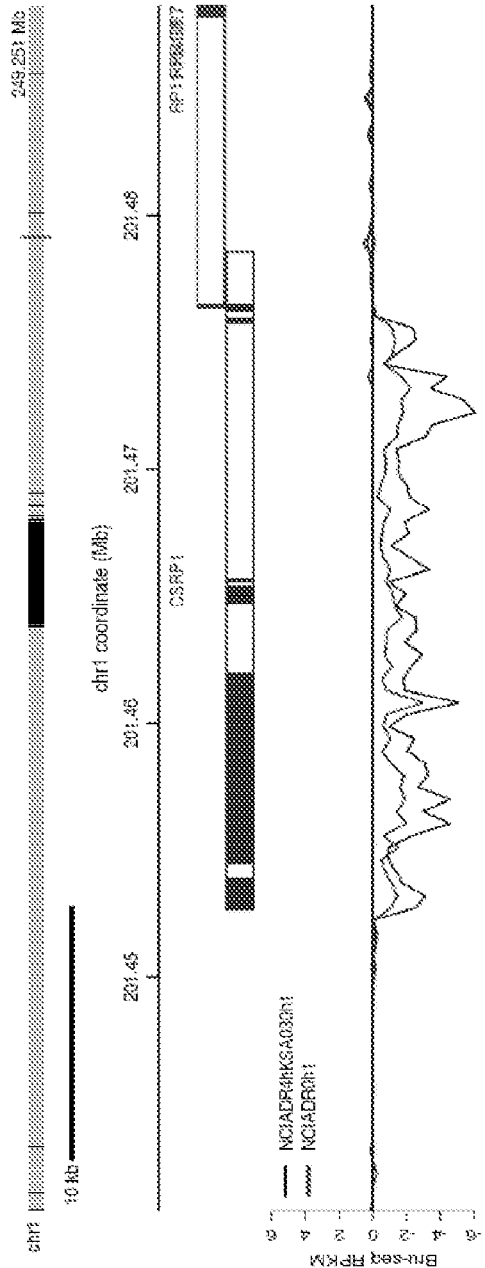
FIG. 8A
FIG. 8B

SMALL MOLECULE INHIBITORS OF MYC AND USES THEREOF

FIELD OF THE INVENTION

This invention is in the field of medicinal chemistry. In particular, the invention relates to a new class of small-molecules having an oxadiazole-oxadiazolone structure which function as inhibitors of MYC protein, and their use as therapeutics for the treatment of cancer and other diseases.

INTRODUCTION

MYC (v-myc myelocytomatosis viral oncogene homolog) is a nuclear DNA-binding transcription factor and seems to be at the crossroads of many important biological pathways underlying cell growth, cell-cycle progression, metabolism, and survival (see, e.g., McKeown, M. R.; Bradner, J. E. Therapeutic Strategies to Inhibit MYC. Cold Spring Harbor Perspectives in Medicine 2014, 4). MYC is documented to be involved broadly in many cancers, in which its expression is estimated to be elevated or deregulated in up to 70% of human cancers. It has been shown that down-regulation of MYC leads to cancer cell growth arrest, senescence, enhanced apoptosis, differentiation and/or tumor regression in mouse models of human cancer (see, e.g., Felsher, D. W. Genes & cancer 2010, 1, 597-604). Hence, MYC is one of the most important targets in the development of cancer treatment.

Members of the MYC oncoprotein family includes C-MYC, N-MYC, and L-MYC. Based on the analysis so far, as many as 20% of human cancers can be associated with the overexpression of C-MYC (see, e.g., Chen, B.-J.; et al., International Journal of Biological Sciences 2014, 10, 1084-1096), and is closely involved in cell cycle, differentiation, protein synthesis, and apoptosis in cells. Several groups have made efforts to develop small molecules that can induce and stabilize G-quadruplexes formed in C-MYC promoter sequences, leading to the inhibition of cancer cell proliferation (see, e.g., Halder, K.; et al., Biochemical and Biophysical Research Communications 2005, 327, 49-56; Nasiri, H. R.; et al., Chemical Communications 2014, 50, 1704-1707). G-quadruplexes have been shown to be a promising target for anti-cancer therapy, based on their functions in regulating C-MYC transcription and suppressing tumorigenicity. Several compounds targeting the C-MYC promoter G-quadruplexes such as (i) perylene compounds (see, e.g., Kerwin, S. M.; et al., Bioorganic & medicinal chemistry letters 2002, 12, 447-50; Li, Q.; et al., Current pharmaceutical design 2012, 18, 1973-83; Pivetta, C.; et al., Bioorganic & medicinal chemistry 2008, 16, 9331-9), (ii) cationic porphyrins (see, e.g., Sun, D.; et al., Nucleic Acids Research 2005, 33, 6070-6080; Verdun, R. E.; et al., Nature 2007, 447, 924-31), (iii) quindolines (see, e.g., Ou, T.-M.; et al., Journal of Medicinal Chemistry 2007, 50, 1465-1474; Ou, T.-M.; et al., Journal of Medicinal Chemistry 2011, 54, 5671-5679), (iv) Hoechst 33258 (see, e.g., Kerwin, S. M.; et al., Bioorganic & medicinal chemistry letters 2002, 12, 447-50), (v) alkaloids (see, e.g., Efferth, T.; et al., Current medicinal chemistry 2007, 14, 2024-32; Lee, H.-M.; et al., Chemical Communications 2010, 46, 4680-4682; Shin-ya, K.; et al., Journal of the American Chemical Society 2001, 123, 1262-1263), (vi) metal complexes (see, e.g., Zhang, J.; et al., Current medicinal chemistry 2012, 19, 2957-75; Wang, J.; et al., Chemical communications (Cambridge, England) 2013, 49, 4758-60), and (vii) carbamide and its analogues (see, e.g., Ma, D.-L.; et al., PLOS ONE 2012, 7, e43278) have been reported. Furthermore, C-MYC also functions through heterodimerization with another basic-helix-loop-helix leucine zipper transcription factor, MAX (see, e.g., Amati, B.; et al., Cell 1993, 72, 233-45). The interaction and heterodimerization between C-MYC and MAX are required in the regulation of all known functions of C-MYC, including regulation of cell proliferation, apoptosis, and target gene transcription (see, e.g., Lüscher, B.; et al., Gene 2012, 494, 145-160). Therefore, other way to down regulate C-MYC functions is interfering with the dimerization of C-MYC/Max. It has been reported that some small molecules can inhibit C-MYC/MAX dimerization such as peptide mimetic compound IIA6B17 (see, e.g., Berg, T.; et al., Proceedings of the National Academy of Sciences of the United States of America 2002, 99, 3830-5), NY2267 (see, e.g., Wang, H.; et al., Molecular cancer therapeutics 2007, 6, 2399-408), 10058-F4, 10074-G5 (see, e.g., Mo, H.; et al., Proceedings of the National Academy of Sciences of the United States of America 2006, 103, 6344-6349).

New compounds capable of inhibiting MYC activity are needed.

The present invention addresses this need.

SUMMARY OF THE INVENTION

The compounds described herein are based on small molecule compounds an oxadiazole-oxadiazolone structure (e.g., oxadiazole-phenyl-oxadiazolone compounds, oxadiazole-pyridine-oxadiazolone compounds, oxadiazole-indole-oxadiazolone compounds, oxadiazole-quinoline-oxadiazolone compounds, oxadiazole-pyrrole-oxadiazolone compounds, and oxadiazole-vinyl-oxadiazolone compounds). Experiments conducted during the course of developing embodiments determined that such compounds exhibit anti-proliferative effects and are useful as monotherapy and/or combination therapy in cancer treatment (e.g., ovarian cancer, pancreatic cancer). In particular, such experiments demonstrated that the small molecule compounds described herein (e.g., having an oxadiazole-oxadiazolone structure) are capable of inhibiting MYC protein activity and thereby inhibit cancer cell activity.

As such, the present invention provides a new class of small-molecules having an oxadiazole-oxadiazolone structure which function as inhibitors of MYC protein, and as therapeutics for the treatment of cancer (e.g., ovarian cancer, pancreatic cancer) and other diseases related to MYC activity.

Indeed, the present invention contemplates that exposure of animals (e.g., humans) suffering from cancer (e.g., ovarian cancer, pancreatic cancer) to therapeutically effective amounts of drug(s) having an oxadiazole-oxadiazolone structure will inhibit the growth of cancer cells and/or supporting cells outright and/or render such cells as a population more susceptible to the cell death-inducing activity of cancer therapeutic drugs or radiation therapies.

The present invention contemplates that inhibitors of MYC activity satisfy an unmet need for the treatment of multiple cancer types, either when administered as monotherapy to induce cell growth inhibition, apoptosis and/or cell cycle arrest in cancer cells, or when administered in a temporal relationship with additional agent(s), such as other cell death-inducing or cell cycle disrupting cancer therapeutic drugs or radiation therapies (combination therapies), so as to render a greater proportion of the cancer cells or supportive cells susceptible to executing the apoptosis program compared to the corresponding proportion of cells in an animal treated only with the cancer therapeutic drug or radiation therapy alone.

In certain embodiments of the invention, combination treatment of animals with a therapeutically effective amount of a compound of the present invention and a course of an anticancer agent produces a greater tumor response and clinical benefit in such animals compared to those treated with the compound or anticancer drugs/radiation alone. Since the doses for all approved anticancer drugs and radiation treatments are known, the present invention contemplates the various combinations of them with the present compounds.

The Applicants have found that certain oxadiazole-oxadiazolone compounds (e.g., oxadiazole-phenyl-oxadiazolone compounds, oxadiazole-pyridine-oxadiazolone compounds, oxadiazole-indole-oxadiazolone compounds, oxadiazole-quinoline-oxadiazolone compounds, oxadiazole-pyrrole-oxadiazolone compounds, and oxadiazole-vinyl-oxadiazolone compounds) function as inhibitors of MYC protein, and serve as therapeutics for the treatment of cancer and other diseases. Thus, the present invention relates to oxadiazole-oxadiazolone compounds useful for inhibiting MYC activity (e.g., thereby facilitating cell apoptosis), and increasing the sensitivity of cells to inducers of apoptosis and/or cell cycle arrest. Certain oxadiazole-oxadiazolone compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

Accordingly, in one aspect, the invention provides a compound of Formula I,

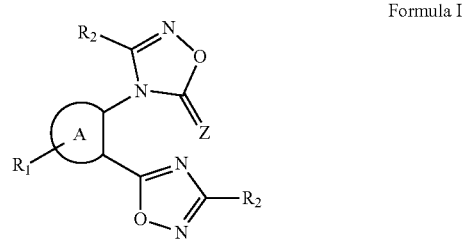

Formula I wherein Z is O, S, N atom; R1 is H, alkyl, or halogen; R2 is substituted aliphatic or aromatic ring; and A comprises a vinyl, ethyl, ethynyl, homocyclic or heterocyclic ring.

In another aspect, the invention provides a compound of Formula II,

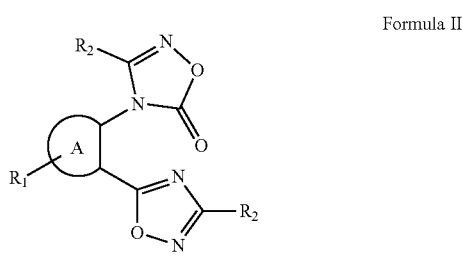

Formula II wherein R1 is H, alkyl, or halogen; R2 is aliphatic or substituted aromatic ring; and A comprises a vinyl, ethyl, ethynyl, homocyclic or heterocyclic ring. For example the alkyl may be methyl or ethyl, the halogen may be F or Cl, and aliphatic may be ethyl, isopropyl or cyclopentyl, substituted aromatic ring may be phenyl, naphthyl, pyrrolyl, pyridinyl, pyrazinyl, fluorophenyl, quinoxalinyl, or pyrroloquinoxalinyl, homocyclic ring may be phenyl, fluorophenyl, naphthyl or cyclopentyl, and heterocyclic ring may be pyrrolyl, pyridinyl, pyrazinyl, quinoxalinyl or pyrrolo-quinoxalinyl. More specifically, in one embodiment, R1 is H, R2 is methyl, A is phenyl; in another embodiment, R1 is H, R2 is ethyl, A is phenyl; in still another embodiment, R1 is H, R2 is isopropyl, A is phenyl; and in yet another embodiment, R1 is H, R2 is cyclopentyl, A is phenyl. Examples of such compounds includes KJA-01, KJA-21, KJA-22, KJA-23, KJA-24, KJA-25, KJA-26, KJA-27, KJA-28, KJA-31, KJA-32, KJA-33, and KJA-34.

| KJA-21 | 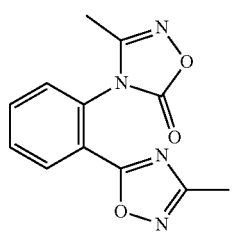 [SMILES: Cc1noc(-c2ccccc2-n2c(C)noc2=O)n1] | 3-methyl-4-(2-(3-methyl-1,2,4-oxadiazol-5-yl)phenyl)-1,2,4-oxadiazol-5(4H)-one |
|---|---|---|

-continued
| | | |
|---|---|---|
| KJA-22 | 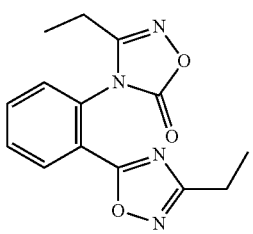 [SMILES: CCc1noc(-c2ccccc2-n2c(CC)noc2=O)n1] | 3-ethyl-4-(2-(3-ethyl-1,2,4-oxadiazol-5-yl)phenyl)-1,2,4-oxadiazol-5(4H)-one |
| KJA-23 | 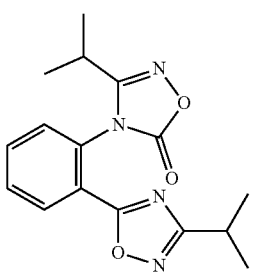 [SMILES: CC(C)c1noc(-c2ccccc2-n2c(C(C)C)noc2=O)n1] | 3-isopropyl-4-(2-(3-isopropyl-1,2,4-oxadiazol-5-yl)phenyl)-1,2,4-oxadiazol-5(4H)-one |
| KJA-24 | 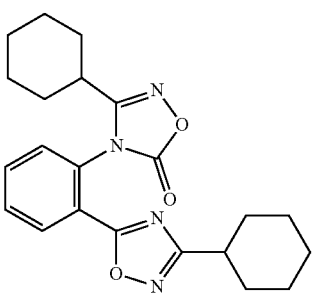 [SMILES: O=c1onc(C2CCCCC2)n1-c1ccccc1-c1nc(C2CCCCC2)no1] | 3-cyclohexyl-4-(2-(3-cyclohexyl-1,2,4-oxadiazol-5-yl)phenyl)-1,2,4-oxadiazol-5(4H)-one |
| KJA-25 | 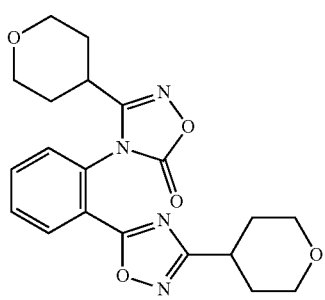 [SMILES: O=c1onc(C2CCOCC2)n1-c1ccccc1-c1nc(C2CCOCC2)no1] | 3-(tetrahydro-2H-pyran-4-yl)-4-(2-(3-(tetrahydro-2H-pyran-4-yl)-1,2,4-oxadiazol-5-yl)phenyl)-1,2,4-oxadiazol-5(4H)-one |
| KJA-26 | 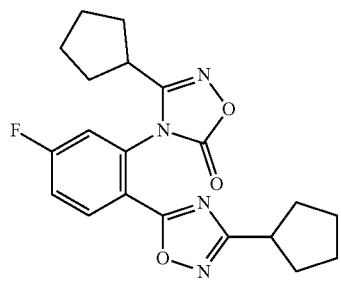 [SMILES: O=c1onc(C2CCCC2)n1-c1cc(F)ccc1-c1nc(C2CCCC2)no1] | 3-cyclopentyl-4-(2-(3-cyclopentyl-1,2,4-oxadiazol-5-yl)-5-fluorophenyl)-1,2,4-oxadiazol-5(4H)-one |

-continued
| | | |
|---|---|---|
| KJA-27 | 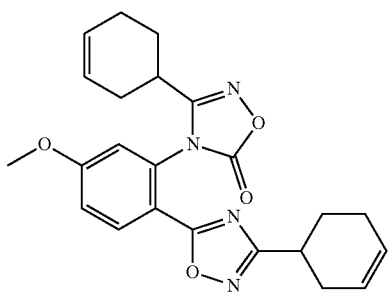 [SMILES: COc1ccc(-c2nc(C3CC=CCC3)no2)c(-n2c(C3CC=CCC3)noc2=O)c1] | 3-(cyclohex-3-en-1-yl)-4-(2-(3-(cyclohex-3-en-1-yl)-1,2,4-oxadiazol-5-yl)-5-methoxyphenyl)-1,2,4-oxadiazol-5(4H)-one |
| KJA-28 | 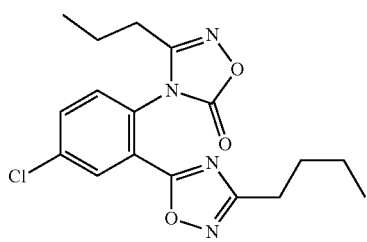 [SMILES: CCCCc1noc(-c2cc(Cl)ccc2-n2c(CCC)noc2=O)n1] | 4-(2-(5-butyl-1l3,2,4-chloraoxazol-3-yl)-4-chlorophenyl)-3-propyl-1,2,4-oxadiazol-5(4H)-one |
| KJA-01 | 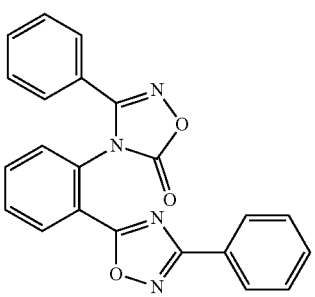 [SMILES: O=c1onc(-c2ccccc2)n1-c1ccccc1-c1nc(-c2ccccc2)no1] | 3-phenyl-4-(2-(5-phenyl-1l3,2,4-chloraoxazol-3-yl)phenyl)-1,2,4-oxadiazol-5(4H)-one |
| KJA-31 | 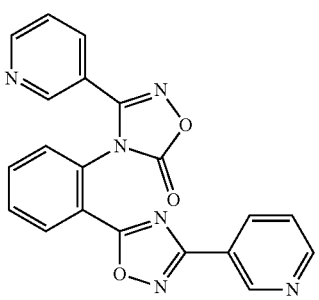 [SMILES: O=c1onc(-c2cccnc2)n1-c1ccccc1-c1nc(-c2cccnc2)no1] | 3-(pyridin-3-yl)-4-(2-(5-(pyridin-3-yl)-1l3,2,4-chloraoxazol-3-yl)phenyl)-1,2,4-oxadiazol-5(4H)-one |
| KJA-32 | 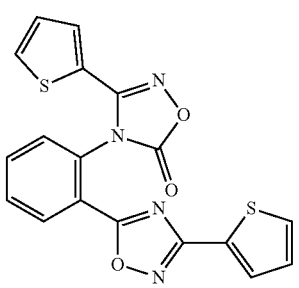 [SMILES: O=c1onc(-c2cccs2)n1-c1ccccc1-c1nc(-c2cccs2)no1] | 3-(thiophen-2-yl)-4-(2-(5-(thiophen-2-yl)-1l3,2,4-chloraoxazol-3-yl)phenyl)-1,2,4-oxadiazol-5(4H)-one |

-continued

| | | |
|---|---|---|
| KJA-33 | 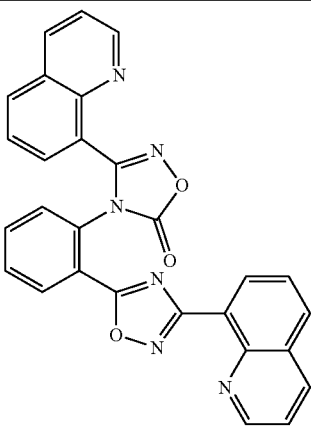 | 3-(quinolin-8-yl)-4-(2-(5-(quinolin-8-yl)-1l3,2,4-chloraoxazol-3-yl)phenyl)-1,2,4-oxadiazol-5(4H)-one |
| KJA-34 | 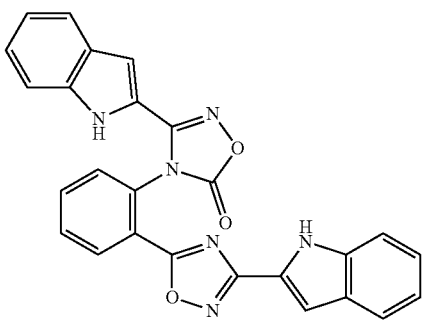 [SMILES: O=c1onc(-c2cc3ccccc3[nH]2)n1-c1ccccc1-c1nc(-c2cc3ccccc3[nH]2)no1] | 4-(2-(5-(1H-indol-2-yl)-1l3,2,4-chloraoxazol-3-yl)phenyl)-3-(1H-indol-2-yl)-1,2,4-oxadiazol-5(4H)-one |

In another aspect, the invention provides a compound of Formula III,

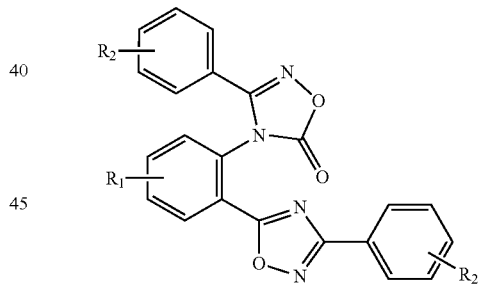

Formula III wherein R1=H, Cl, F, Me or OMe, R2=H, Cl, F, Me, OMe, ethyl or dimethylamino. Examples of such compounds include KJA-02, KJA-03, KJA-04, KJA-05, KJA-06, KJA-07, KJA-08, KJA-03, KJA-10, KJA-16 and KJA-17.

| | | |
|---|---|---|
| KJA-02 | 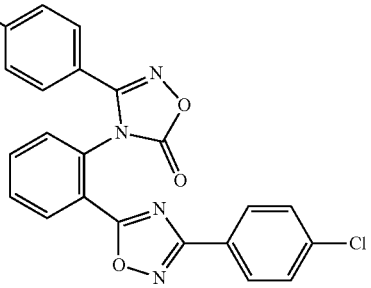 | 3-(4-chlorophenyl)-4-(2-(3-(4-chlorophenyl)-1,2,4-oxadiazol-5-yl)phenyl)-1,2,4-oxadiazol-5(4H)-one |

-continued
KJA-03 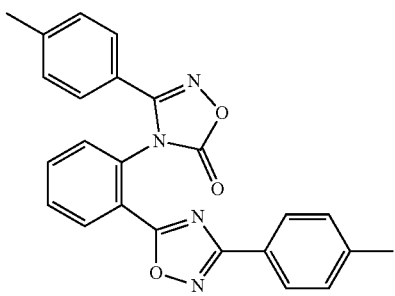 3-(p-tolyl)-4-(2-(3-(p-tolyl)-1,2,4-oxadiazol-5-yl)phenyl)-1,2,4-oxadiazol-5(4H)-one
KJA-04 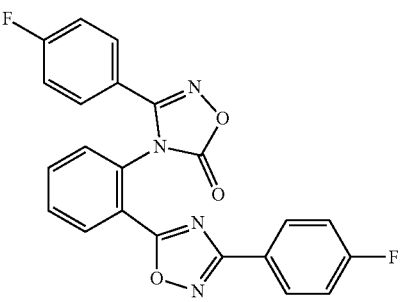 [SMILES: O=c1onc(-c2ccc(F)cc2)n1-c1ccccc1-c1nc(-c2ccc(F)cc2)no1] 3-(4-fluorophenyl)-4-(2-(3-(4-fluorophenyl)-1,2,4-oxadiazol-5-yl)phenyl)-1,2,4-oxadiazol-5(4H)-one
KJA-05 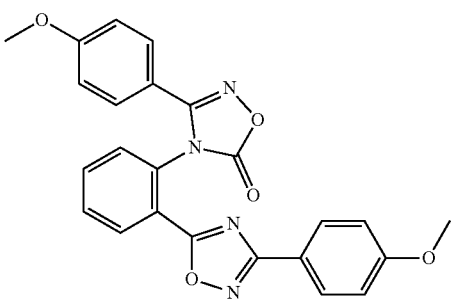 3-(4-methoxyphenyl)-4-(2-(3-(4-methoxyphenyl)-1,2,4-oxadiazol-5-yl)phenyl)-1,2,4-oxadiazol-5(4H)-one
KJA-07 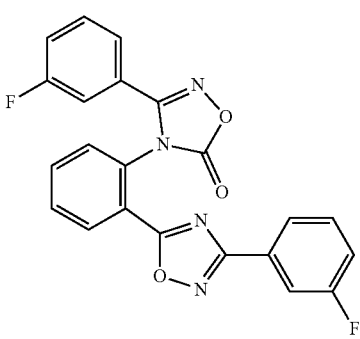 [SMILES: O=c1onc(-c2cccc(F)c2)n1-c1ccccc1-c1nc(-c2cccc(F)c2)no1] 3-(3-fluorophenyl)-4-(2-(3-(3-fluorophenyl)-1,2,4-oxadiazol-5-yl)phenyl)-1,2,4-oxadiazol-5(4H)-one
KJA-17 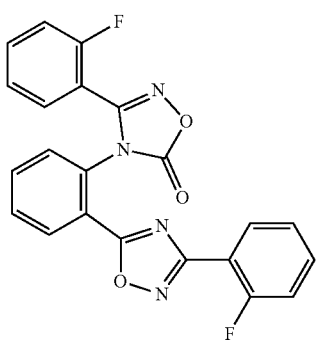 [SMILES: O=c1onc(-c2ccccc2F)n1-c1ccccc1-c1nc(-c2ccccc2F)no1] 3-(2-fluorophenyl)-4-(2-(3-(2-fluorophenyl)-1,2,4-oxadiazol-5-yl)phenyl)-1,2,4-oxadiazol-5(4H)-one

| | | |
|---|---|---|
| KJA-06 | 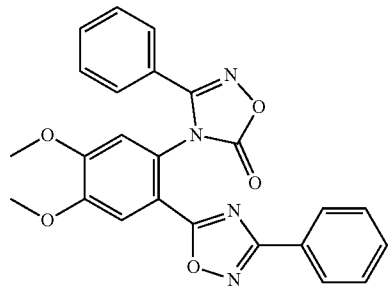 [SMILES: COc1cc(-c2nc(-c3ccccc3)no2)c(-n2c(-c3ccccc3)noc2=O)cc1OC] | 4-(4,5-dimethoxy-2-(3-phenyl-1,2,4-oxadiazol-5-yl)phenyl)-3-phenyl-1,2,4-oxadiazol-5(4H)-one |
| KJA-09 | 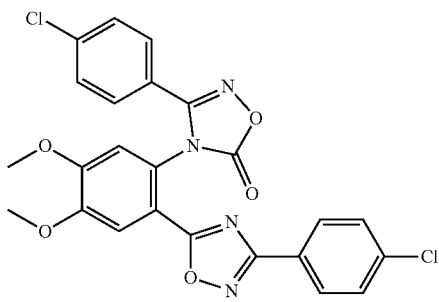 [SMILES: COc1cc(-c2nc(-c3ccc(Cl)cc3)no2)c(-n2c(-c3ccc(Cl)cc3)noc2=O)cc1OC] | 3-(4-chlorophenyl)-4-(2-(3-(4-chlorophenyl)-1,2,4-oxadiazol-5-yl)-4,5-dimethoxyphenyl)-1,2,4-oxadiazol-5(4H)-one |
| KJA-08 | 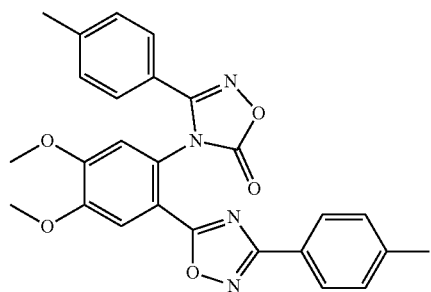 | 4-(4,5-dimethoxy-2-(3-(p-tolyl)-1,2,4-oxadiazol-5-yl)phenyl)-3-(p-tolyl)-1,2,4-oxadiazol-5(4H)-one |
| KJA-10 | 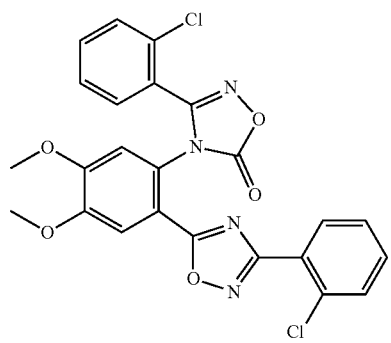 [SMILES: COc1cc(-c2nc(-c3ccccc3Cl)no2)c(-n2c(-c3ccccc3Cl)noc2=O)cc1OC] | 3-(2-chlorophenyl)-4-(2-(3-(2-chlorophenyl)-1,2,4-oxadiazol-5-yl)-4,5-dimethoxyphenyl)-1,2,4-oxadiazol-5(4H)-one |
| KJA-16 | 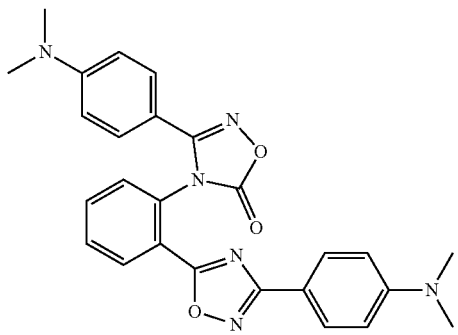 | 3-(4-(dimethylamino)phenyl)-4-(2-(3-(4-(dimethylamino)phenyl)-1,2,4-oxadiazol-5-yl)phenyl)-1,2,4-oxadiazol-5(4H)-one |

In another aspect, the invention provides a compound of Formula IV,

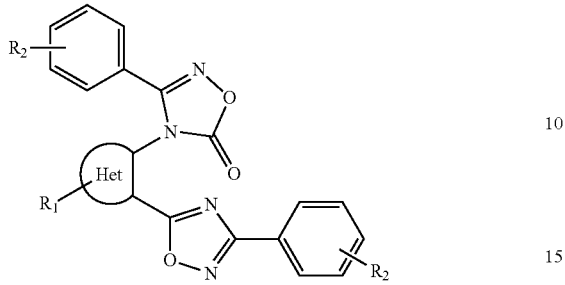

Formula IV wherein Het is pyridinyl, indolyl, quinolinyl or pyrazinyl; R1=H, Cl, F, Me or OMe, R2=H, Cl, F, Me, OMe, ethyl or dimethylamino. Examples of such compounds include KJA-43, KJA-44, KJA-45, KJA-46 and KJA-07.

KJA-43

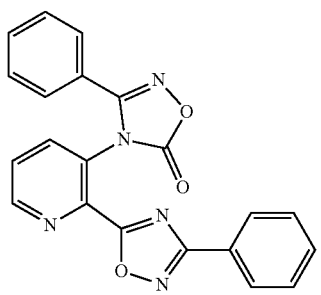

3-phenyl-4-(2-(3-phenyl-1,2,4-oxadiazol-5-yl)pyridin-3-yl)-1,2,4-oxadiazol-5(4H)-one

KJA-44

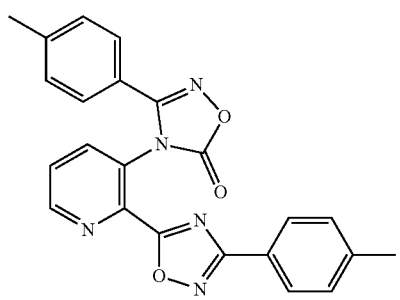

3-(p-tolyl)-4-(2-(3-(p-tolyl)-1,2,4-oxadiazol-5-yl)pyridin-3-yl)-1,2,4-oxadiazol-5(4H)-one

KJA-45

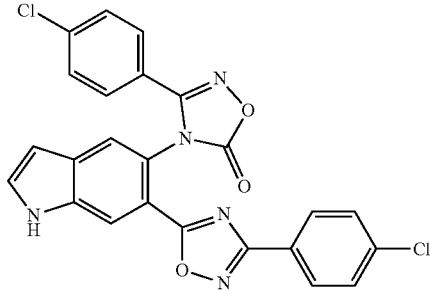 [SMILES: O=c1onc(-c2ccc(Cl)cc2)n1-c1cc2cc[nH]c2cc1-c1nc(-c2ccc(Cl)cc2)no1]

3-(4-chlorophenyl)-4-(6-(3-(4-chlorophenyl)-1,2,4-oxadiazol-5-yl)-1H-indol-5-yl)-1,2,4-oxadiazol-5(4H)-one

| | | |
|---|---|---|
| KJA-46 | 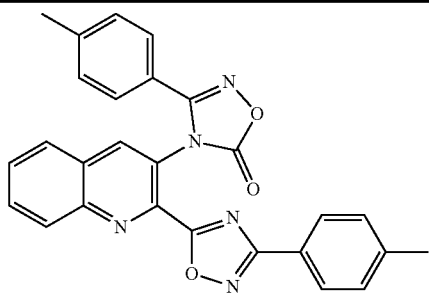 | 3-(p-tolyl)-4-(2-(3-(p-tolyl)-1,2,4-oxadiazol-5-yl)quinolin-3-yl)-1,2,4-oxadiazol-5(4H)-one |
| KJA-47 | 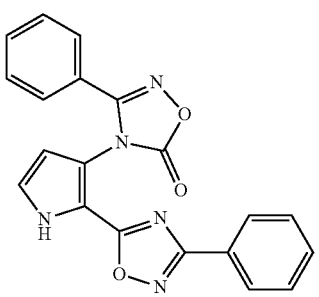 [SMILES: O=c1onc(-c2ccccc2)n1-c1cc[nH]c1-c1nc(-c2ccccc2)no1] | 3-phenyl-4-(2-(3-phenyl-1,2,4-oxadiazol-5-yl)-1H-pyrrol-3-yl)-1,2,4-oxadiazol-5(4H)-one |

In another aspect, the invention provides a compound of Formula V,

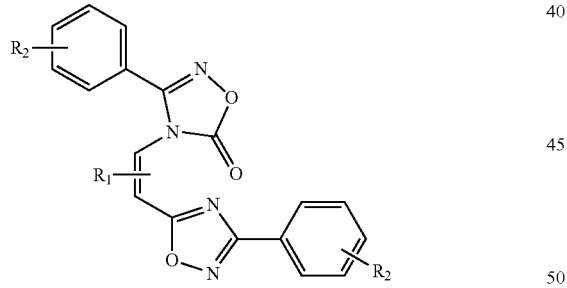

Formula IV wherein R1=H, methyl or ethyl; R2=H, Cl, F, Me, OMe, ethyl or dimethylamino. Examples of such compounds include KJA-62, KJA-63, KJA-64 and KJA-65.

| | | |
|---|---|---|
| KJA-62 | 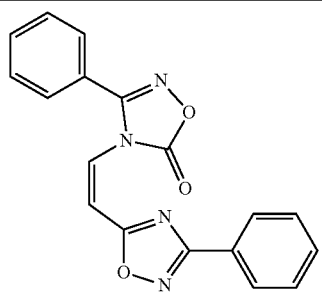 | (Z)-3-phenyl-4-(2-(3-phenyl-1,2,4-oxadiazol-5-yl)vinyl)-1,2,4-oxadiazol-5(4H)-one |

-continued

| | | |
|---|---|---|
| KJA-63 | 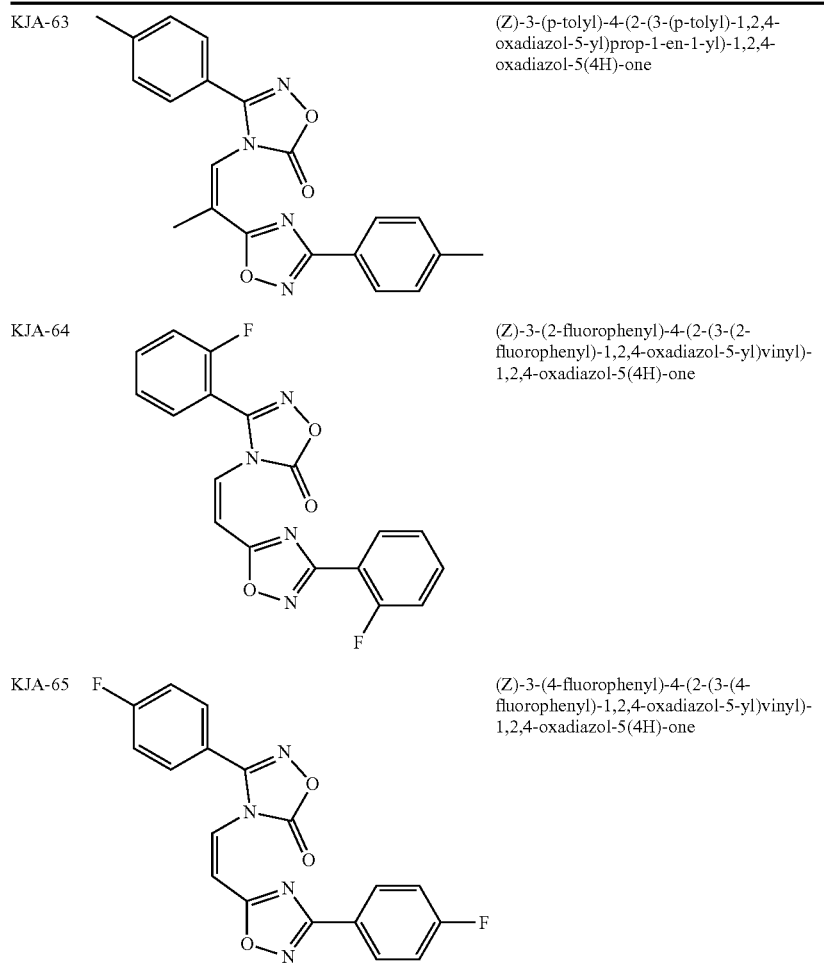 | (Z)-3-(p-tolyl)-4-(2-(3-(p-tolyl)-1,2,4-oxadiazol-5-yl)prop-1-en-1-yl)-1,2,4-oxadiazol-5(4H)-one |
| KJA-64 | | (Z)-3-(2-fluorophenyl)-4-(2-(3-(2-fluorophenyl)-1,2,4-oxadiazol-5-yl)vinyl)-1,2,4-oxadiazol-5(4H)-one |
| KJA-65 | | (Z)-3-(4-fluorophenyl)-4-(2-(3-(4-fluorophenyl)-1,2,4-oxadiazol-5-yl)vinyl)-1,2,4-oxadiazol-5(4H)-one |

In certain embodiments, the present invention provides methods of preparing the compounds of invention. For example, in some embodiments, compounds KJA-01, KJA-02, KJA-03, KJA-04, KJA-05, KJA-06, KJA-07, KJA-08, KJA-03, KJA-10, KJA-16 and KJA-17 can be prepared as follows: contact nitrile oxides of Formula VI with a compound (1a, 1b, 1c or 1d) of Formula VII, Formula VI

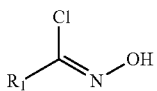

wherein R1 is substituted aliphatic or aromatic ring;

Formula VII

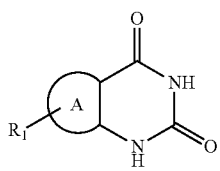

wherein R1 is H, alkyl, or halogen; and A comprises a vinyl, ethyl, ethynyl, homocyclic or heterocyclic ring.

The invention further provides processes for preparing any of the compounds of the present invention through following at least a portion of the techniques recited the Examples.

The invention also relates to the use of compounds for sensitizing cells to additional agent(s), such as inducers of apoptosis and/or cell cycle arrest, and chemoprotection of normal cells through the induction of cell cycle arrest prior to treatment with chemotherapeutic agents.

The compounds of the invention are useful for the treatment, amelioration, or prevention of disorders, such as those responsive to induction of apoptotic cell death, e.g., disorders characterized by dysregulation of apoptosis, including hyperproliferative diseases such as cancer (e.g., ovarian cancer, pancreatic cancer). In certain embodiments, the compounds can be used to treat, ameliorate, or prevent cancer (e.g., ovarian cancer, pancreatic cancer) that is characterized by resistance to cancer therapies (e.g., those cancer cells which are chemoresistant, radiation resistant, hormone resistant, and the like). Examples of cancer include leukemia, non-small cell lung cancer, colon cancer, CNS cancer, melanoma, ovarian cancer, breast cancer, renal cancer, and prostate cancer. In certain embodiments, the cancer is pancreatic cancer and/or ovarian cancer.

In certain embodiments, the present invention provides methods of monitoring a treatment of a subject by administering to a subject having cancer cells or cells associated with a MYC function disorder an oxadiazole-oxadiazolone compound as described herein and measuring the survival of the cells, the growth of the cells, or a combination thereof using PET imaging. The subject may be suffering from leukemia, non-small cell lung cancer, colon cancer, CNS cancer, melanoma, ovarian cancer, breast cancer, renal cancer, prostate cancer, age-related macular degeneration, macular dystrophy, or diabetes. The subject may be an animal, e.g., a mouse, and the cells may be xenografted human cells. In some embodiments, the subject is a human.

In certain embodiments, the present invention provides methods for profiling gene expression. For example, in some embodiments, such methods comprise contacting a test cell with an oxadiazole-oxadiazolone compound as described herein and profiling gene expression in the test cell. The test cell may be a cancer cell or a cell associated with an angiogenesis function disorder. More specifically, the test cell may be a leukemia cell, non-small cell lung cancer cell, colon cancer cell, CNS cancer cell, melanoma cell, ovarian cancer cell, breast cancer cell, renal cancer cell, prostate cancer cell; or a cell associated with age-related macular degeneration, macular dystrophy, or diabetes. The method may further comprise comparing gene expression in the test cell with that in a control cell, which may be contacted with another compound with known action or resistant to the compound used to contact the test cell.

The invention also provides pharmaceutical compositions comprising the compounds of the invention in a pharmaceutically acceptable carrier.

The invention also provides kits comprising a compound of the invention and instructions for administering the compound to an animal. The kits may optionally contain other therapeutic agents, e.g., anticancer agents or apoptosis-modulating agents. For example, in some embodiments, the present invention provides a kit comprising a packaged product comprising a container; an effective amount of a compound of Formula II wherein, R1 is H, alkyl, or halogen; R2 is substituted aliphatic, aromatic ring; and A comprises a vinyl, ethyl, ethynyl, homocyclic or heterocyclic ring; and an insert associated with the container, indicating administering the compound for treating cancer. In some embodiments, the present invention provides a packaged product comprising a container; an effective amount of a compound of the invention; and an insert associated with the container, indicating administering the compound for treating cancer or a disorder associated with angiogenesis function. Such kits may further comprise, for example, an effective amount of one or more other agents for treating cancer, e.g., taxol, doxorubicin, or 5-FU.

DEFINITIONS

Figure 1:
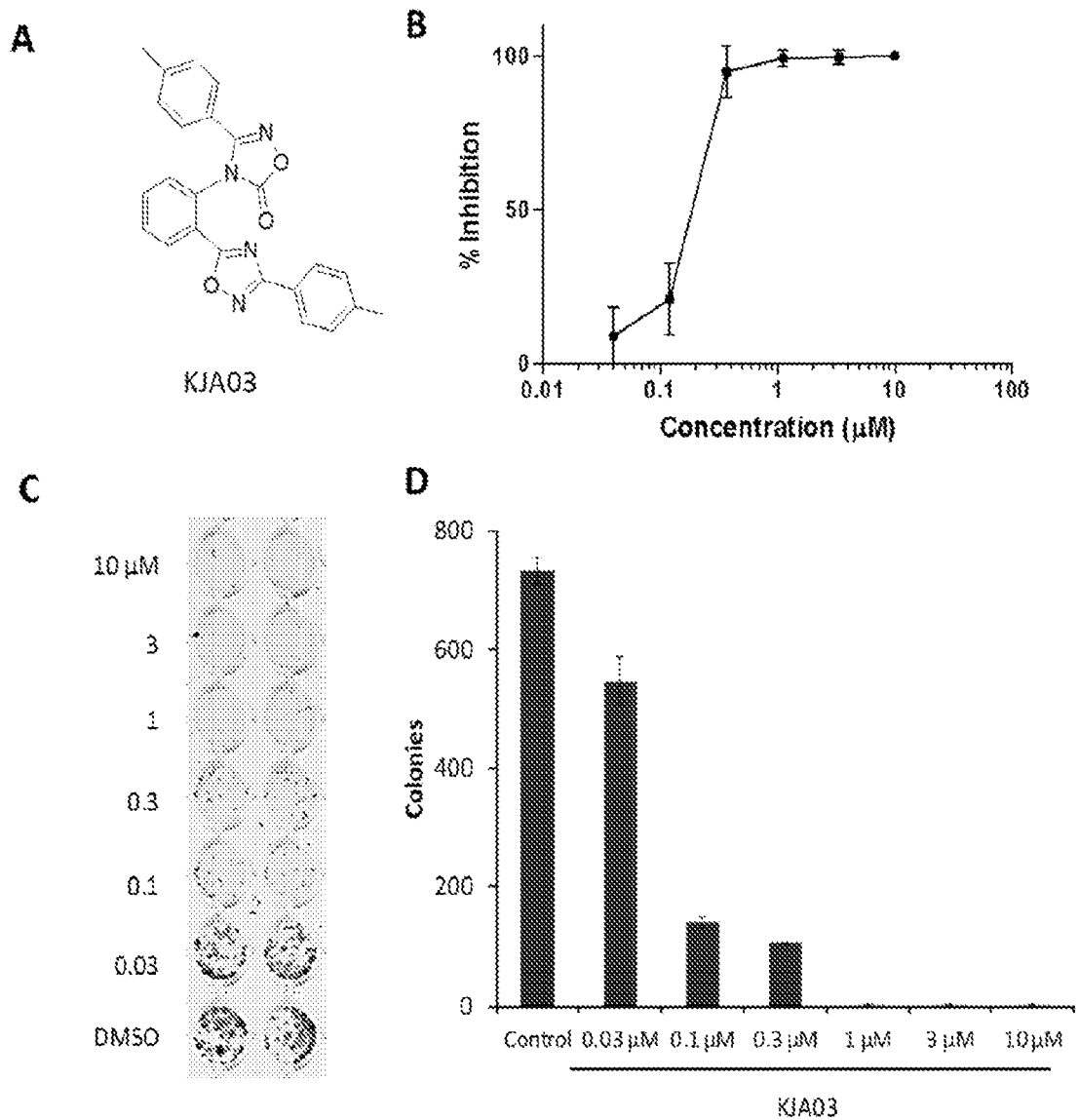
FIG. 1 A) Structures of KJA03; (B) KJA03 inhibited growth of NCI/ADR-RES as measured by MTT assay after 72 h treatment; (C) KJA03 inhibited colony formation in NCI/ADR-RES cells after 24 h treatment; (D) The histogram shows the mean number of colonies.

The term "anticancer agent" as used herein, refer to any therapeutic agents (e.g., chemotherapeutic compounds and/or molecular therapeutic compounds), antisense therapies, radiation therapies, or surgical interventions, used in the treatment of hyperproliferative diseases such as cancer (e.g., in mammals, e.g., in humans).

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate (see, e.g., US Patent Application Publication No. US 2007/0249564 A1; herein incorporated by reference in its entirety).

The term "pharmaceutically acceptable salt" as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "solvate" as used herein, refers to the physical association of a compound of the invention with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and isolable solvates. Exemplary solvates include hydrates, ethanolates, and methanolates.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that decreases the rate of tumor growth, decreases tumor mass, decreases the number of metastases, increases time to tumor progression, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent (e.g., a benzoic acid compound of the invention), an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least 300%, at least about 350%, at least about 400%, at least about 450%, or at least about 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, non-limiting examples of which include, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis.

The term "hyperproliferative disease," as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The term "neoplastic disease," as used herein, refers to any abnormal growth of cells being either benign (noncancerous) or malignant (cancerous).

The term "normal cell," as used herein, refers to a cell that is not undergoing abnormal growth or division. Normal cells are non-cancerous and are not part of any hyperproliferative disease or disorder.

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

DETAILED DESCRIPTION OF THE INVENTION

Experiments conducted during the course of developing embodiments for the present invention resulted in the designing and synthesis of oxadiazole-oxadiazolone compounds having remarkable cytotoxicity patterns against a panel of human cancer cell lines. Indeed, a series of oxadiazole-phenyl-oxadiazolone compounds (e.g., oxadiazole-phenyl-oxadiazolone compounds, oxadiazole-pyridine-oxadiazolone compounds, oxadiazole-indole-oxadiazolone compounds, oxadiazole-quinoline-oxadiazolone compounds, oxadiazole-pyrrole-oxadiazolone compounds, and oxadiazole-vinyl-oxadiazolone compounds) were tested against several drug-resistant cancer cell lines. KJA03 was selected as a lead molecule based on potency. KJA03 showed $IC_{50}$ values ranging from 0.13-0.31 μM against five cancer cell lines. Experiments were additionally conducted to perform next-generation sequencing to identify gene expression profile in response to drug treatment. KJA03 was shown to significantly reduce MYC protein levels at 0.1 (half IC50) and 0.2 ($IC_{50}$) μM at 24 and 48 h. Subsequently, experiments were conducted wherein a lead optimization campaign was performed to synthesize a series of novel analogs. Twenty novel analogs were synthesized and tested in three pancreatic cancer cell lines using MTT assay. KJA03 showed no symptoms of gross toxicity such as weakness, weight loss or lethargy. KJA03 treatment was shown to significantly increase the expression of LAMC2, TAGLN, CSRP1, SLC4A4, LAMB3, and LPP genes, thereby indicating activation of the stress response pathway. Considering the cytotoxicity profile displayed by this compound in a variety of in vitro models, the oxadiazole-oxadiazolone compounds described herein (e.g., KJA03) represent a novel candidates for the treatment of cancer and disorders associated with MYC function.

Accordingly, the present invention relates to a new class of small-molecules having an oxadiazole-oxadiazolone structure which function as inhibitors of MYC activity, and their use as therapeutics for the treatment of cancer and other diseases.

In a particular embodiment, oxadiazole-phenyl-oxadiazolone compounds encompassed within Formula VIII are provided:

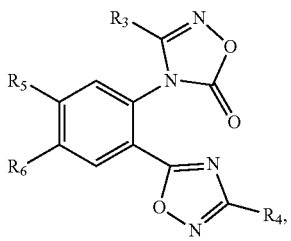

including pharmaceutically acceptable salts, solvates, and/or prodrugs thereof.

In a particular embodiment, oxadiazole-pyridine-oxadiazolone compounds encompassed within Formula IX are provided:

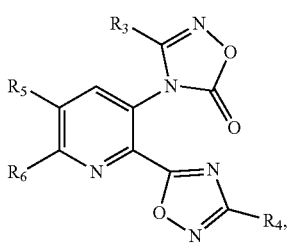

including pharmaceutically acceptable salts, solvates, and/or prodrugs thereof.

In a particular embodiment, oxadiazole-indole-oxadiazolone compounds encompassed within Formula X are provided: including

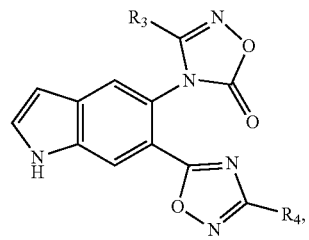

pharmaceutically acceptable salts, solvates, and/or prodrugs thereof.

In a particular embodiment, oxadiazole-quinoline-oxadiazolone compounds encompassed within Formula XI are provided:

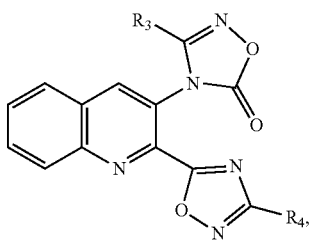

including pharmaceutically acceptable salts, solvates, and/or prodrugs thereof.

In a particular embodiment, oxadiazole-pyrrole-oxadiazolone compounds encompassed within Formula XII are provided:

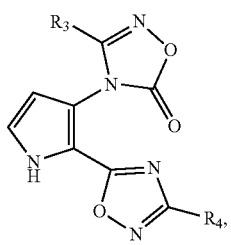

including pharmaceutically acceptable salts, solvates, and/or prodrugs thereof.

In a particular embodiment, oxadiazole-vinyl-oxadiazolone compounds encompassed within Formula XIII are provided:

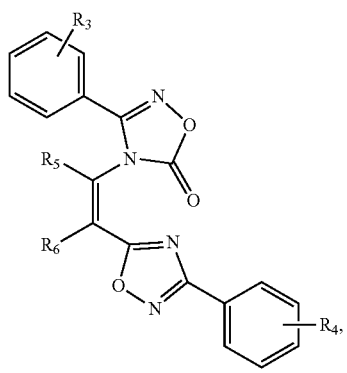

including pharmaceutically acceptable salts, solvates, and/or prodrugs thereof.

Formulas VIII, IX, X, XI, XII and XIII are not limited to a particular chemical moiety for $R_3$, $R_4$, $R_5$ and $R_6$.

In some embodiments, the particular chemical moiety for $R_3$, $R_4$, $R_5$ and $R_6$ independently include any chemical moiety that permits the resulting compound to inhibit MYC activity within cancer cells and/or cells having aberrant MYC activity.

In some embodiments, $R_3$ and $R_4$ are independently a chemical moiety selected from hydrogen, methyl,

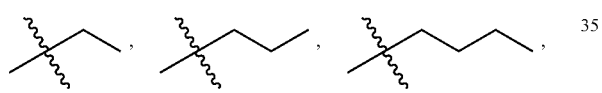

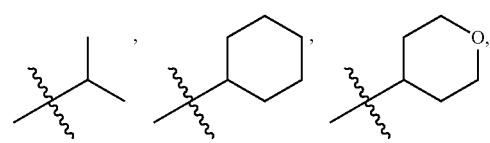

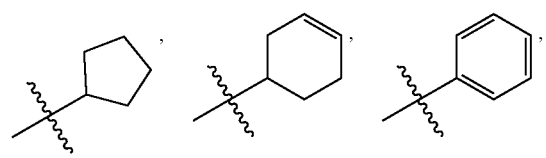

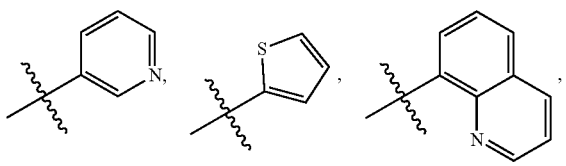

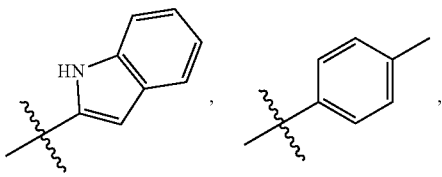

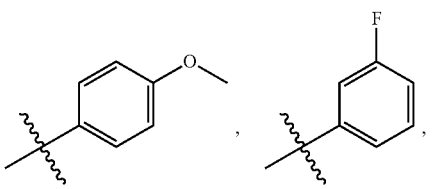

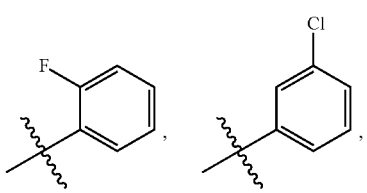

In some embodiments, the chemical moiety for $R_3$ and $R_4$ are identical. In some embodiments, the chemical moiety for $R_3$ and $R_4$ are not identical.

In some embodiments, $R_5$ and $R_6$ are independently a chemical moiety selected from hydrogen, fluorine, chlorine, and

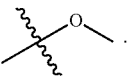 [SMILES: *OC ; "."]

In some embodiments, the chemical moiety for $R_5$ and $R_6$ are identical. In some embodiments, the chemical moiety for $R_5$ and $R_6$ are not identical.

In some embodiments, the following compounds are contemplated for Formula VIII:

| | | |
|---|---|---|
| KJA-21 | 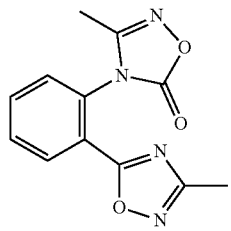 [SMILES: Cc1noc(-c2ccccc2-n2c(C)noc2=O)n1] | 3-methyl-4-(2-(3-methyl-1,2,4-oxadiazol-5-yl)phenyl)-1,2,4-oxadiazol-5(4H)-one |
| KJA-22 | 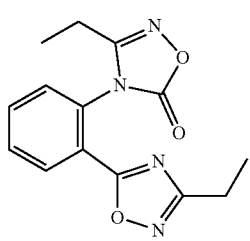 [SMILES: CCc1noc(-c2ccccc2-n2c(CC)noc2=O)n1] | 3-ethyl-4-(2-(3-ethyl-1,2,4-oxadiazol-5-yl)phenyl)-1,2,4-oxadiazol-5(4H)-one |
| KJA-23 | 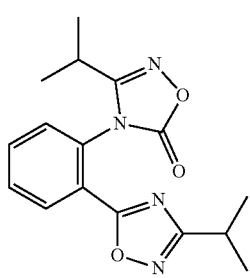 [SMILES: CC(C)c1noc(-c2ccccc2-n2c(C(C)C)noc2=O)n1] | 3-isopropyl-4-(2-(3-isopropyl-1,2,4-oxadiazol-5-yl)phenyl)-1,2,4-oxadiazol-5(4H)-one |
| KJA-24 | 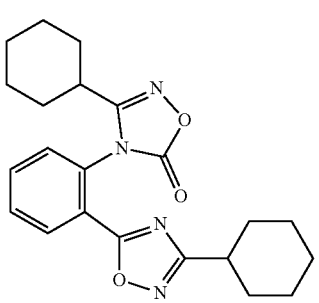 [SMILES: O=c1onc(C2CCCCC2)n1-c1ccccc1-c1nc(C2CCCCC2)no1] | 3-cyclohexyl-4-(2-(3-cyclohexyl-1,2,4-oxadiazol-5-yl)phenyl)-1,2,4-oxadiazol-5(4H)-one |
| KJA-25 | 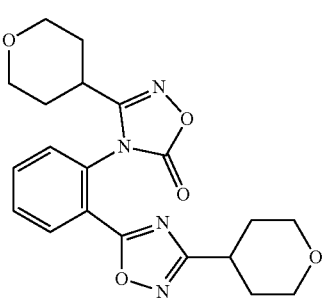 [SMILES: O=c1onc(C2CCOCC2)n1-c1ccccc1-c1nc(C2CCOCC2)no1] | 3-(tetrahydro-2H-pyran-4-yl)-4-(2-(3-(tetrahydro-2H-pyran-4-yl)-1,2,4-oxadiazol-5-yl)phenyl)-1,2,4-oxadiazol-5(4H)-one |

| | | |
|---|---|---|
| KJA-26 | 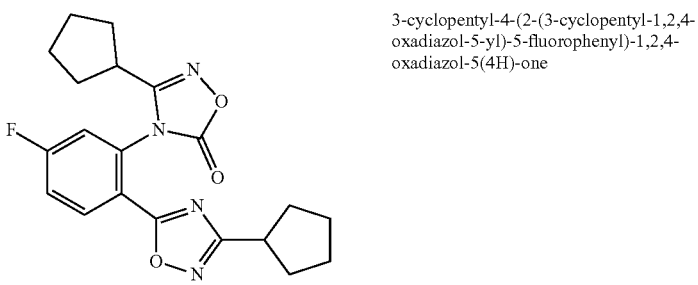 | 3-cyclopentyl-4-(2-(3-cyclopentyl-1,2,4-oxadiazol-5-yl)-5-fluorophenyl)-1,2,4-oxadiazol-5(4H)-one |
| KJA-27 | 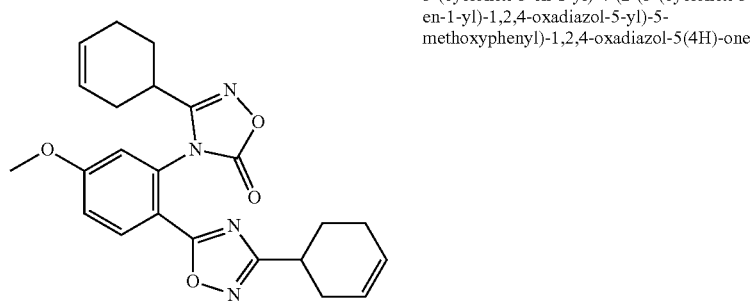 | 3-(cyclohex-3-en-1-yl)-4-(2-(3-(cyclohex-3-en-1-yl)-1,2,4-oxadiazol-5-yl)-5-methoxyphenyl)-1,2,4-oxadiazol-5(4H)-one |
| KJA-28 | 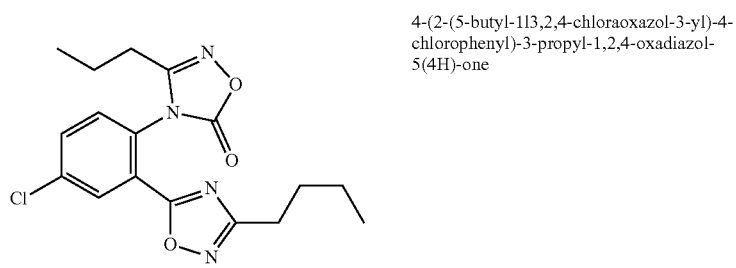 | 4-(2-(5-butyl-1l3,2,4-chloraoxazol-3-yl)-4-chlorophenyl)-3-propyl-1,2,4-oxadiazol-5(4H)-one |
| KJA-01 | 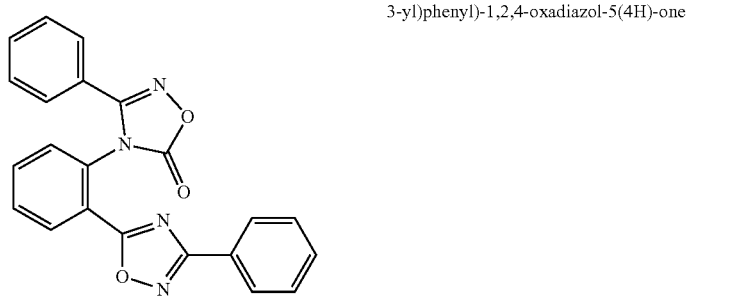 | 3-phenyl-4-(2-(5-phenyl-1l3,2,4-chloraoxazol-3-yl)phenyl)-1,2,4-oxadiazol-5(4H)-one |
| KJA-31 | 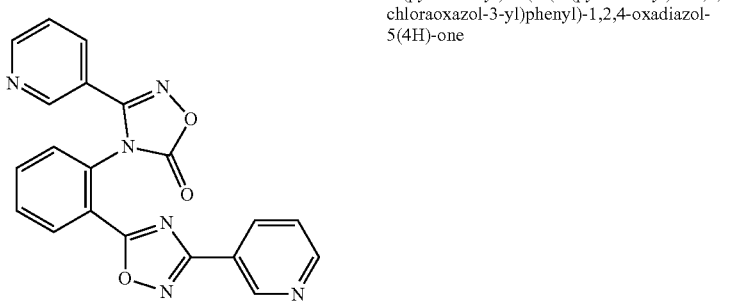 | 3-(pyridin-3-yl)-4-(2-(5-(pyridin-3-yl)-1l3,2,4-chloraoxazol-3-yl)phenyl)-1,2,4-oxadiazol-5(4H)-one |

-continued
| | | |
|---|---|---|
| KJA-32 | 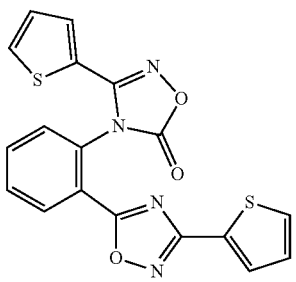 [SMILES: O=c1onc(-c2cccs2)n1-c1ccccc1-c1nc(-c2cccs2)no1] | 3-(thiophen-2-yl)-4-(2-(5-(thiophen-2-yl)-1l3,2,4-chloraoxazol-3-yl)phenyl)-1,2,4-oxadiazol-5(4H)-one |
| KJA-33 | 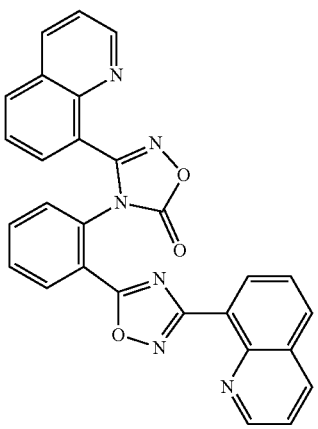 [SMILES: O=c1onc(-c2cccc3cccnc23)n1-c1ccccc1-c1nc(-c2cccc3cccnc23)no1] | 3-(quinolin-8-yl)-4-(2-(5-(quinolin-8-yl)-1l3,2,4-chloraoxazol-3-yl)phenyl)-1,2,4-oxadiazol-5(4H)-one |
| KJA-34 | 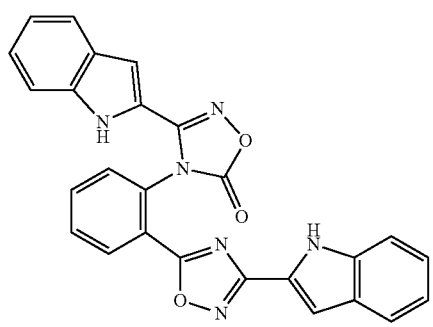 [SMILES: O=c1onc(-c2cc3ccccc3[nH]2)n1-c1ccccc1-c1nc(-c2cc3ccccc3[nH]2)no1] | 4-(2-(5-(1H-indol-2-yl)-1l3,2,4-chloraoxazol-3-yl)phenyl)-3-(1H-indol-2-yl)-1,2,4-oxadiazol-5(4H)-one |
| | | |
|---|---|---|
| KJA-02 | 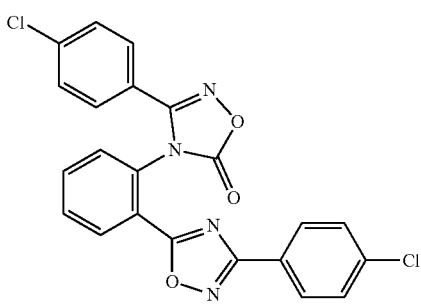 [SMILES: O=c1onc(-c2ccc(Cl)cc2)n1-c1ccccc1-c1nc(-c2ccc(Cl)cc2)no1] | 3-(4-chlorophenyl)-4-(2-(3-(4-chlorophenyl)-1,2,4-oxadiazol-5-yl)phenyl)-1,2,4-oxadiazol-5(4H)-one |

| | | |
|---|---|---|
| KJA-03 | | 3-(p-tolyl)-4-(2-(3-(p-tolyl)-1,2,4-oxadiazol-5-yl)phenyl)-1,2,4-oxadiazol-5(4H)-one |
| KJA-04 | | 3-(4-fluorophenyl)-4-(2-(3-(4-fluorophenyl)-1,2,4-oxadiazol-5-yl)phenyl)-1,2,4-oxadiazol-5(4H)-one |
| KJA-05 | | 3-(4-methoxyphenyl)-4-(2-(3-(4-methoxyphenyl)-1,2,4-oxadiazol-5-yl)phenyl)-1,2,4-oxadiazol-5(4H)-one |
| KJA-07 | | 3-(3-fluorophenyl)-4-(2-(3-(3-fluorophenyl)-1,2,4-oxadiazol-5-yl)phenyl)-1,2,4-oxadiazol-5(4H)-one |
| KJA-17 | | 3-(2-fluorophenyl)-4-(2-(3-(2-fluorophenyl)-1,2,4-oxadiazol-5-yl)phenyl)-1,2,4-oxadiazol-5(4H)-one |

-continued

KJA-06 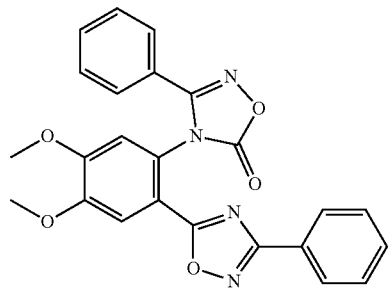 [SMILES: COc1cc(-c2nc(-c3ccccc3)no2)c(-n2c(-c3ccccc3)noc2=O)cc1OC] 4-(4,5-dimethoxy-2-(3-phenyl-1,2,4-oxadiazol-5-yl)phenyl)-3-phenyl-1,2,4-oxadiazol-5(4H)-one KJA-09 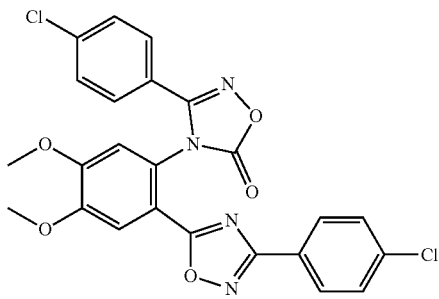 [SMILES: COc1cc(-c2nc(-c3ccc(Cl)cc3)no2)c(-n2c(-c3ccc(Cl)cc3)noc2=O)cc1OC] 3-(4-chlorophenyl)-4-(2-(3-(4-chlorophenyl)-1,2,4-oxadiazol-5-yl)-4,5-dimethoxyphenyl)-1,2,4-oxadiazol-5(4H)-one KJA-08 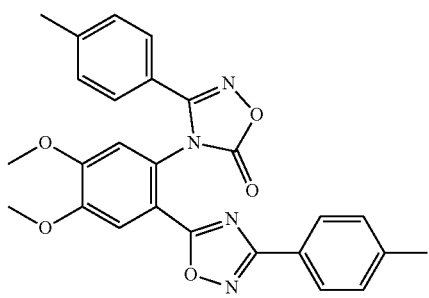 4-(4,5-dimethoxy-2-(3-(p-tolyl)-1,2,4-oxadiazol-5-yl)phenyl)-3-(p-tolyl)-1,2,4-oxadiazol-5(4H)-one KJA-10 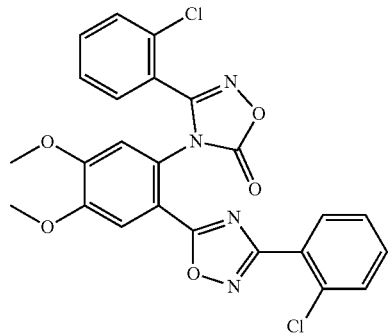 [SMILES: COc1cc(-c2nc(-c3ccccc3Cl)no2)c(-n2c(-c3ccccc3Cl)noc2=O)cc1OC] 3-(2-chlorophenyl)-4-(2-(3-(2-chlorophenyl)-1,2,4-oxadiazol-5-yl)-4,5-dimethoxyphenyl)-1,2,4-oxadiazol-5(4H)-one KJA-16 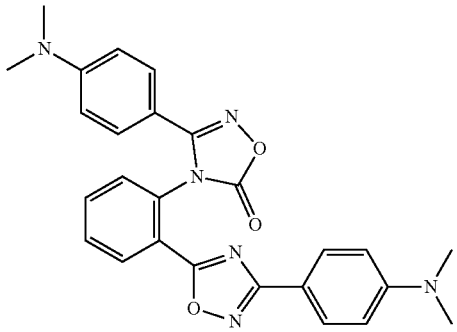 3-(4-(dimethylamino)phenyl)-4-(2-(3-(4-(dimethylamino)phenyl)-1,2,4-oxadiazol-5-yl)phenyl)-1,2,4-oxadiazol-5(4H)-one In some embodiments, the following compounds are contemplated for Formulas IX, X, XI and XII:

| | | |
|---|---|---|
| KJA-43 | 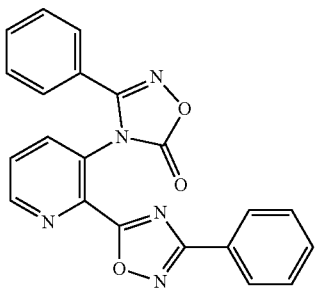 [SMILES: O=c1onc(-c2ccccc2)n1-c1cccnc1-c1nc(-c2ccccc2)no1] | 3-phenyl-4-(2-(3-phenyl-1,2,4-oxadiazol-5-yl)pyridin-3-yl)-1,2,4-oxadiazol-5(4H)-one |
| KJA-44 | 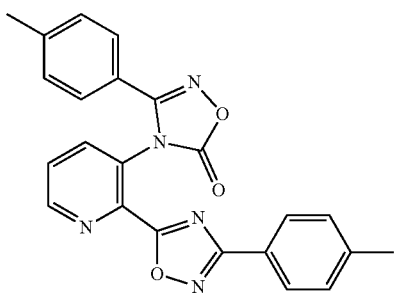 | 3-(p-tolyl)-4-(2-(3-(p-tolyl)-1,2,4-oxadiazol-5-yl)pyridin-3-yl)-1,2,4-oxadiazol-5(4H)-one |
| KJA-45 | 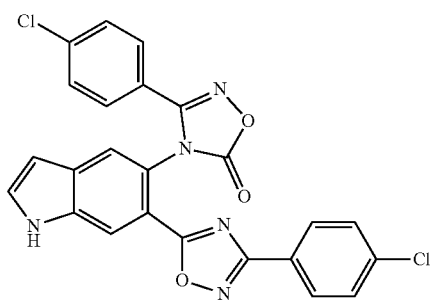 [SMILES: O=c1onc(-c2ccc(Cl)cc2)n1-c1cc2cc[nH]c2cc1-c1nc(-c2ccc(Cl)cc2)no1] | 3-(4-chlorophenyl)-4-(6-(3-(4-chlorophenyl)-1,2,4-oxadiazol-5-yl)-1H-indol-5-yl)-1,2,4-oxadiazol-5(4H)-one |
| KJA-46 | 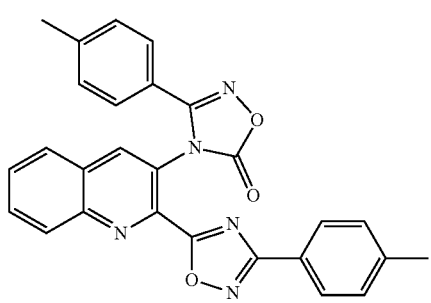 [SMILES: Cc1ccc(-c2noc(-c3nc4ccccc4cc3-n3c(-c4ccc(C)cc4)noc3=O)n2)cc1] | 3-(p-tolyl)-4-(2-(3-(p-tolyl)-1,2,4-oxadiazol-5-yl)quinolin-3-yl)-1,2,4-oxadiazol-5(4H)-one |
| KJA-47 | 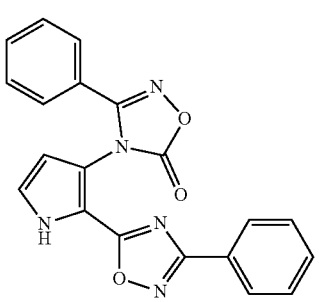 [SMILES: O=c1onc(-c2ccccc2)n1-c1cc[nH]c1-c1nc(-c2ccccc2)no1] | 3-phenyl-4-(2-(3-phenyl-1,2,4-oxadiazol-5-yl)-1H-pyrrol-3-yl)-1,2,4-oxadiazol-5(4H)-one |

In some embodiments, the following compounds are contemplated for Formula XIII:

KJA-62 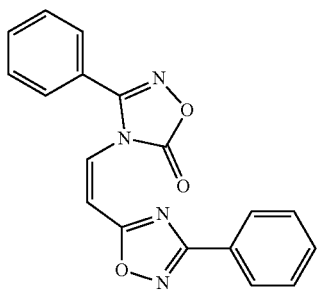 [SMILES: O=c1onc(-c2ccccc2)n1/C=C\c1nc(-c2ccccc2)no1] (Z)-3-phenyl-4-(2-(3-phenyl-1,2,4-oxadiazol-5-yl)vinyl)-1,2,4-oxadiazol-5(4H)-one KJA-63 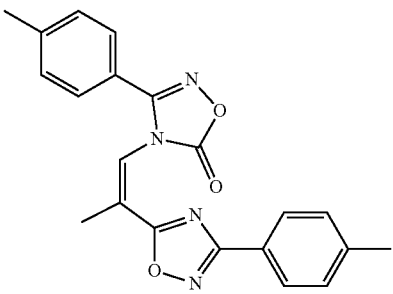 (Z)-3-(p-tolyl)-4-(2-(3-(p-tolyl)-1,2,4-oxadiazol-5-yl)prop-1-en-1-yl)-1,2,4-oxadiazol-5(4H)-one KJA-64 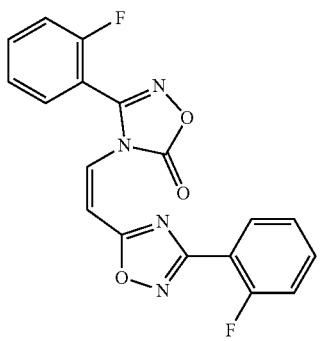 [SMILES: O=c1onc(-c2ccccc2F)n1/C=C\c1nc(-c2ccccc2F)no1] (Z)-3-(2-fluorophenyl)-4-(2-(3-(2-fluorophenyl)-1,2,4-oxadiazol-5-yl)vinyl)-1,2,4-oxadiazol-5(4H)-one KJA-65 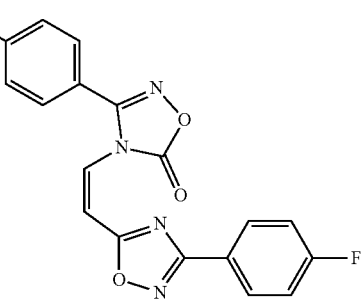 (Z)-3-(4-fluorophenyl)-4-(2-(3-(4-fluorophenyl)-1,2,4-oxadiazol-5-yl)vinyl)-1,2,4-oxadiazol-5(4H)-one A compound of the invention may include both substituted and unsubstituted moieties. The term "substituted" refers to moieties having one, two, three or more substituents, which may be the same or different, each replacing a hydrogen atom. Examples of substituents include, but are not limited to, alkyl, hydroxyl, protected hydroxyl, amino, protected amino, carboxy, protected carboxy, cyano, alkoxy, and nitro. The term "unsubstituted" refers to a moiety having each atom hydrogenated such that the valency of each atom is filled. A reactive moiety is "protected" when it is temporarily and chemically transformed such that it does not react under conditions where the non-protected moiety reacts. For example, trimethylsilylation is a typical transformation used to protect reactive functional groups such as hydroxyl or amino groups from their reaction with growing anionic species in anionic polymerization.

Protected forms of the compounds are included within the scope of the invention. In general, the species of protecting group is not critical, provided that it is stable to the conditions of any subsequent reactions on other positions of the compound and can be removed at the appropriate point without adversely affecting the remainder of the molecule. In addition, one protecting group may be substituted for another after substantive synthetic transformations are complete. Examples and conditions for the attachment and removal of various protecting groups are found in Greene, Protective Groups in Organic Chemistry, 1st ed., 1981, and 2nd ed., 1991. In addition, salts of the compounds are within the scope of the invention. For example, a salt can be formed between a positively charged amino substituent and a negatively charged counter-ion.

In some embodiments, the compositions and methods of the present invention are used to treat diseased cells, tissues, organs, or pathological conditions and/or disease states in an animal (e.g., a mammalian patient including, but not limited to, humans and veterinary animals). In some embodiments, the compositions and methods of the present invention are used to treat diseased cells, tissues, organs, or pathological conditions and/or disease states in an animal (e.g., a mammalian patient including, but not limited to, humans and veterinary animals) related to/associated with MCL activity.

In this regard, various diseases and pathologies are amenable to treatment or prophylaxis using the present methods and compositions. A non-limiting exemplary list of these diseases and conditions includes, but is not limited to, pancreatic cancer, ovarian cancer, and other types of cancer (e.g., breast cancer, prostate cancer, lymphoma, skin cancer, colon cancer, melanoma, malignant melanoma, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma). In some embodiments, the cancer cells being treated are metastatic. In other embodiments, the cancer cells being treated are resistant to anticancer agents.

Some embodiments of the present invention provide methods for administering an effective amount of a compound of the invention and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies). In a particular embodiment, the additional therapeutic agent(s) is an anticancer agent.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); antiandrogens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of the invention and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N'',N'',-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile,a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl)ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2-chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |

TABLE 1-continued

| | | |
|---|---|---|
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin in PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |

TABLE 1-continued

| | | |
|---|---|---|
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl) oxy]-7,8,9,10-tetrahydro-6,9,11-trihydroxyhydrochloride,(7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4':6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((-)-(S)-2,3,5,6-tetrahydro-6-phenylimidazo [2,1-b]thiazole monohydrochloride $C_{11}H_{12}N_2S \bullet HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Mechlorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |

TABLE 1-continued

| Drug | Brand | Company |
|---|---|---|
| Melphalan, L-PAM (4-[bis(2-chloroethyl)amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl)ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel ($5\beta$,20-Epoxy-1,2a,4,7$\beta$,10$\beta$,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-$\mu$-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH_2)$) | Sclerosol | Bryan, Corp., Woburn, MA |

TABLE 1-continued

| | | |
|---|---|---|
| Tamoxifen<br>((Z)2-[4-(1,2-diphenyl-1-butenyl) phenoxy]-<br>N,N-dimethylethanamine 2-hydroxy-1,2,3-<br>propanetricarboxylate (1:1)) | Nolvadex | AstraZeneca Pharmaceuticals |
| Temozolomide<br>(3,4-dihydro-3-methyl-4-oxoimidazo[5,1-d]-<br>as-tetrazine-8-carboxamide) | Temodar | Schering |
| teniposide, VM-26<br>(4'-demethylepipodophyllotoxin 9-[4,6-0-(R)-<br>2-thenylidene-(beta)-D-glucopyranoside]) | Vumon | Bristol-Myers Squibb |
| Testolactone<br>(13-hydroxy-3-oxo-13,17-secoandrosta-1,4-<br>dien-17-oic acid[dgr]-lactone) | Teslac | Bristol-Myers Squibb |
| Thioguanine, 6-TG<br>(2-amino-1,7-dihydro-6H-purine-6-thione) | Thioguanine | GlaxoSmithKline |
| Thiotepa<br>(Aziridine, 1,1',1''-phosphinothioylidynetris-,<br>or Tris (1-aziridinyl) phosphine sulfide) | Thioplex | Immunex Corporation |
| Topotecan HCl<br>((S)-10-[(dimethylamino)<br>methyl]-4-ethyl-4,9-dihydroxy-1H-<br>pyrano[3',4': 6,7]indolizino<br>[1,2-b]quinoline-3,14-(4H,12H)-dione<br>monohydrochloride) | Hycamtin | GlaxoSmithKline |
| Toremifene<br>(2-(p-[(Z)-4-chloro-1,2-diphenyl-1-butenyl]-<br>phenoxy)-N,N-dimethylethylamine citrate<br>(1:1)) | Fareston | Roberts Pharmaceutical Corp.,<br>Eatontown, NJ |
| Tositumomab, I 131 Tositumomab<br>(recombinant murine immunotherapeutic<br>monoclonal IgG$_{2a}$ lambda anti-CD20 antibody<br>(I 131 is a radioimmunotherapeutic antibody)) | Bexxar | Corixa Corp., Seattle, WA |
| Trastuzumab<br>(recombinant monoclonal IgG$_1$ kappa anti-<br>HER2 antibody) | Herceptin | Genentech, Inc |
| Tretinoin, ATRA<br>(all-trans retinoic acid) | Vesanoid | Roche |
| Uracil Mustard | Uracil<br>Mustard<br>Capsules | Roberts Labs |
| Valrubicin, N-trifluoroacetyladriamycin-14-<br>valerate<br>((2S-cis)-2-[1,2,3,4,6,11-hexahydro-2,5,12-<br>trihydroxy-7 methoxy-6,11-dioxo-[[4 2,3,6-<br>trideoxy-3-[(trifluoroacetyl)-amino-α-L-lyxo-<br>hexopyranosyl]oxyl]-2-naphthacenyl]-2-<br>oxoethyl pentanoate) | Valstar | Anthra → Medeva |
| Vinblastine, Leurocristine<br>($C_{46}H_{56}N_4O_{10}\cdot H_2SO_4$) | Velban | Eli Lilly |
| Vincristine<br>($C_{46}H_{56}N_4O_{10}\cdot H_2SO_4$) | Oncovin | Eli Lilly |
| Vinorelbine<br>(3',4'-didehydro-4'-deoxy-C'-<br>norvincaleukoblastine [R-(R*,R*)-<br>2,3-dihydroxybutanedioate<br>(1:2)(salt)]) | Navelbine | GlaxoSmithKline |
| Zoledronate, Zoledronic acid<br>((1-Hydroxy-2-imidazol-1-yl-phosphonoethyl)<br>phosphonic acid monohydrate) | Zometa | Novartis |

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724, 714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of the invention with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, a compound of the invention and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

The present invention provides methods and techniques associated with measuring/determining gene expression patterns. Indeed, gene expression patterns in response to drug treatment are strong indications of the mechanism of action, mechanism of resistance and cellular pathways for the drug. Profiling of gene expression, e.g., by means of RNA-seq technology, is useful for identifying and validating drug targets, and for monitoring drug treatment.

Accordingly, the invention provides a method of profiling gene expression by contacting a test cell with a compound described above and profiling gene expression in the test cell. In particular, the test cell may be a cancer cell. Gene expression in the test cell may be compared with that in a control cell, e.g., a cell not contacted with the compound, a cell contacted with another compound with known action, or a cell resistant to the compound. Such comparison provides useful information for understanding the action of the compound.

Gene expression can be determined at mRNA and protein levels. The presence, level, or absence of a protein or nucleic acid in a biological sample can be evaluated by obtaining a biological sample from a test subject and contacting the biological sample with an agent capable of detecting the protein or nucleic acid (e.g., mRNA, genomic DNA) that encodes the protein such that the presence of the protein or nucleic acid is detected in the biological sample. The term "biological sample" includes tissues, cells and biological fluids isolated from a subject, as well as tissues, cells and fluids present within a subject. The level of expression of a gene can be measured in a number of ways, including, but not limited to: measuring the mRNA transcribed from the gene, measuring the amount of protein encoded by the gene, or measuring the activity of the protein encoded by the gene.

The level of mRNA transcribed from the gene in a cell can be determined both by in situ and by in vitro formats. The isolated mRNA can be used in hybridization or amplification assays that include, but are not limited to, Southern or Northern analyses, polymerase chain reaction analyses and probe arrays. One preferred diagnostic method for detection of the mRNA level involves contacting the isolated mRNA with a nucleic acid molecule (probe) that can hybridize to the mRNA transcribed from the gene being detected. The probe can be disposed on an address of an array.

The level of mRNA in a sample can be evaluated with nucleic acid amplification, e.g., by RT-PCR (U.S. Pat. No. 4,683,202), ligase chain reaction (Barany (1991) Proc. Natl. Acad. Sci. USA 88:189-193), self sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA transcribed from the gene being analyzed.

A variety of methods can be used to determine the level of protein encoded by the gene. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')2) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance.

The detection methods can be used to detect a protein in a biological sample in vitro as well as in vivo. In vitro techniques for detection of a protein include enzyme linked immunosorbent assays (ELISAs), immunoprecipitations, immunofluorescence, enzyme immunoassay (EIA), radioimmunoassay (RIA), and Western blot analysis. In vivo techniques for detection of a protein include introducing into a subject a labeled antibody. For example, the antibody can be labeled with a radioactive marker whose presence and location in a subject can be detected by standard imaging techniques. In another embodiment, the sample is labeled, e.g., biotinylated and then contacted to the antibody, e.g., an antibody positioned on an antibody array. The sample can be detected, e.g., with avidin coupled to a fluorescent label.

It is now well established that RNA-Seq technology allows simultaneous quantification of the expression of thousands of genes. This methodology is now robust, reproducible, and highly efficient. It can be used to evaluate cellular pathways and validate drug targets.

Clustering of compounds into presumed mechanistic groupings based on the similarity in their growth inhibition profiles across the NCI 60 human cancer cell-lines was first realized by Paull et al. ((1989) J. Natl. Cancer Inst. 81:1088-1092). They developed a computer program called "COMPARE" which is based on a pattern recognition algorithm that assesses the degree of similarity of compounds based on their cytotoxicity profiles. Some of the compounds were classified according to their published and widely accepted molecular targets. Previously, Dr. John Weinstein and his colleagues at NCI have created a software package called "DISCOVERY" to compare the gene expression analysis of 60 cell lines using a cDNA chip containing 1,200 genes (Weinstein et al. (1997) Science 275:343-349). A correlation between gene expression patterns and the cytotoxic profiles against 60 cell lines in response to a particular compound could be determined (Scherf et al. (2000) Nat. Genet. 24:236-244). Using this methodology, it is possible to identify targets or pathways for these compounds. DISCOVERY then allows the identification of genes common to the pathways by correlative gene expression. This publicly available software allows comparison of compounds against a database of 5000 compounds in the NCI 60 human cancer cell-lines (see the NCI web site at discover.nci.nih.gov).

Genes identified through profiling as responsive to the treatment of a compound may be used as therapeutic markers. These markers can in turn be used to monitor treatment of a subject with the compound.

Another aspect of the invention pertains to methods of modulating gene expression or activity for therapeutic purposes. Accordingly, the modulatory method of the invention involves contacting a cell with a compound described above that modulates expression of one or more of the genes associated with the cell.

These modulatory methods can be performed in vitro, e.g., by culturing the cell with the compound. For example, the cell may be a cancer cell (e.g., a leukemia cell, non-small cell lung cancer cell, colon cancer cell, CNS cancer cell, melanoma cell, ovarian cancer cell, breast cancer cell, renal cancer cell, prostate cancer cell) or a cell associated with an angiogenesis function disorder (e.g., a cell associated with age-related macular degeneration, macular dystrophy, or diabetes). Alternatively, the modulatory methods can be performed in vivo, e.g., by administering the compound to a subject such as a subject suffering from or at risk for developing cancer or a disorder associated with angiogenesis function. As such, the present invention provides methods of treating a subject afflicted with a disease or disorder characterized by aberrant or unwanted expression of one or more of the genes. Stimulation of gene expression is desirable in situations in which the gene is abnormally down-regulated and/or in which increased gene expression is likely to have a beneficial effect. Likewise, inhibition of gene expression is desirable in situations in which gene expression is abnormally upregulated and/or in which decreased gene expression is likely to have a beneficial effect.

The following examples are intended to illustrate, but not to limit, the scope of the invention. While such examples are typical of those that might be used, other procedures known to those skilled in the art may alternatively be utilized.

Indeed, those of ordinary skill in the art can readily envision and produce further embodiments, based on the teachings herein, without undue experimentation.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

General Experimental Methods

All compounds were fully characterized by infrared (IR), NMR, and high-resolution mass spectrometry (HRMS). NMR spectra were recorded on a Bruker DRX400 (1H: 400 MHz, 13C: 100 MHz) or Bruker DRX500 (1H: 500 MHz, 13C: 125 MHz) using deuterated CDCl3 and DMSO-d6 as solvents. Chemical shifts (δ) are expressed in parts per million, and J values given in hertz. IR spectra were recorded on a Fourier transform infrared (FT-IR) Thermo Nicolet Avatar 360 using a KBr pellet. Reactions were monitored by thin layer chromatography (TLC) using silica gel GF254. The melting points were determined using a XT-4A melting point apparatus and were uncorrected. HRMS was performed on an Agilent liquid chromatography/mass selective detector time-of-flight instrument. All chemicals and solvents were used as received without further purification, unless otherwise stated. Column chromatography was performed on silica gel (200-300 mesh). All commercially available reagents were purchased from Adamas-Beta Corporation Limited and used without further purification unless otherwise stated.

General Procedure for the Synthesis of Intermediate Benzaldehyde Oxime.

Substituted benzaldehyde (50 mmol), hydroxylamine hydrochloride (50 mmol) and $K_2CO_3$ (50 mmol) were dissolved in 50 mL methanol into a 125 mL round-bottom flask. The mixture was stirred at room temperature for 3 h and monitored by TLC. After the reaction was completed, solvent was removed with a rotary evaporator and then water was added to the residue, extracted with ethyl acetate. The organic phase was dried over anhydrous sodium sulfate, concentrated by rotary evaporator to yield intermediate benzaldoxime (90 to 96% yield).

General Procedure for the Synthesis of Hydroxybenzimidoyl Chloride.

Benzaldoxime (50 mmol) and N-chiorosuccinimide (50 mmol) were dissolved in 40 mL DMF and placed into a 125 mL round-bottom flask and the mixture was stirred at room temperature for 2-4 h. Completion of the reaction was monitored by TLC. Water was added, the mixture was extracted with ethyl acetate, dried over $Na_2SO_4$, concentrated and purified by flash column chromatography to yield intermediate 1a-o (92 to 95% yield).

General Procedure for the Synthesis of KJA Compounds

Hydroxybenzimidoyl chloride 1a-o (22 mmol), substituted quinizol-2,4-dione (10 mmol) and Cs$_2$CO$_3$ (30 mmol) were dissolved in 25 mL of mixed solvent (MeOH:DMSO=1:2), the mixture was stirred at room temperature for 3 h. Progress of the reaction was monitored by TLC. The mixture was evaporated by rotary evaporator, extracted with ethyl acetate, dried over Na$_2$SO$_4$, concentrated and purified by flash column chromatography (PE/EA=7:1) to yield compound 3a-q (71 to 91% yield). The products were further characterized by FTIR, NMR and HRMS, and were in good agreement with the target structures.

3-Phenyl-4-(2-(3-phenyl-1,2,4-oxadiazol-5-yl)phenyl)-1,2,4-oxadiazol-5(4H)-one (KJA-01)

Milk white solid, m.p. 181.3~182.4° C.; IR (KBr): 3414, 3068, 2917, 2850, 1779, 1671, 1607, 1561, 1526, 1501, 1444, 1415, 1358, 1331, 1310, 1289, 1177, 1148, 1109, 1073, 1027, 971, 883, 751, 692 cm$^{-1}$; $^1$H NMR (400 MHz, DMSO-d$_6$): δ=8.32 (d, J=6.8 Hz, 1H, ArH), 8.05~8.04 (m, 3H, ArH), 7.98~7.94 (m, 1H, ArH), 7.88~7.84 (m, 1H, ArH), 7.66~7.63 (m, 3H, ArH), 7.48 (t, J=7.6 Hz, 1H, ArH), 7.36 (d, J=8.0 Hz, 2H, ArH), 7.28 (d, J=7.2 Hz, 2H, ArH); $^{13}$C NMR (100 MHz, DMSO-d$_6$): δ=172.5, 168.6, 158.5, 158.1, 135.3, 132.5, 132.4, 132.1, 131.1, 130.6, 129.9, 129.7, 129.5, 129.0, 128.3, 127.4, 126.0, 123.1, 121.8. HRMS (TOP ES$^+$): m/z calculated for C$_{22}$H$_{14}$N$_4$O$_3$Na [M+Na]$^+$, 405.0958; found, 405.0962.

3-(4-Chlorophenyl)-4-(2-(3-(4-chlorophenyl)-1,2,4-oxadiazol-5-yl)phenyl)-1,2,4-oxadiazol-5(4H)-one (KJA-02)

Milk white solid, m.p. 201.2~203.0° C.; IR (KBr): 3552, 3479, 3413, 3235, 1782, 1638, 1616, 1559, 1427, 1360, 1175, 1093, 1014, 839, 757, 623, 479 cm$^{-1}$; $^1$H NMR (400 MHZ, DMSO-d$_6$): δ=8.36~8.34 (m, 1H, ArH), 8.06~7.96 (m, 4H, ArH), 7.90~7.86 (m, 1H, ArH), 7.35 (d, J=8.4 HZ, 2H, ArH), 7.47 (d, J=8.4 Hz, 2H, ArH), 7.33 (d, J=8.4 Hz, 2H, ArH); $^{13}$C NMR (100 MHz, DMSO-d$_6$): δ=172.7, 167.8, 158.0, 157.8, 137.3, 135.5, 132.3, 132.1, 131.3, 130.4, 130.2, 130.1, 129.9, 129.1, 129.0, 128.5, 124.9, 121.9, 121.6. HRMS (TOP ES$^+$): m/z calculated for C$_{22}$H$_{12}$N$_4$Cl$_2$O$_3$Na [M+Na]$^+$, 473.0179; found, 473.0089.

3-(P-tolyl)-4-(2-(3-(p-tolyl)-1,2,4-oxadiazol-5-yl)phenyl)-1,2,4-oxadiazol-5(4H)-one (KJA-03)

White solid, m.p. 225.0~226.0° C.; IR (KBr): 2918, 2850, 1784, 1610, 1592, 1537, 1517, 1502, 1444, 1421, 1357, 1330, 1179, 1109, 754, 739, 636 cm$^{-1}$; $^1$H NMR (400 MHz, CDCl$_3$): δ=8.26 (d, J=7.6 Hz, 1H, ArH), 7.98 (d, J=8.0 Hz, 2H, ArH), 7.78~7.76 (m, 1H, ArH), 7.72~7.65 (m, 2H, ArH), 7.18 (d, J=8.0 Hz, 2H, ArH), 7.11 (d, J=8.0 Hz, 2H, ArH), 7.01 (d, J=8.0 Hz, 2H, ArH), 2.43 (s, 3H, CH$_3$), 2.25 (s, 3H, CH$_3$); $^{13}$C NMR (100 MHz, CDCl$_3$): δ=171.4, 169.0, 158.5, 158.0, 142.4, 142.0, 134.0, 131.1, 130.9, 130.7, 129.8, 129.6, 127.6, 127.5, 123.4, 122.6, 120.2, 21.6, 21.4. HRMS (TOP ES$^+$): m/z calculated for C$_{24}$H$_{18}$H$_4$O$_3$Na [M+Na]$^+$, 433.1271; found, 433.1276.

3-(4-Fluorophenyl)-4-(2-(3-(4-fluorophenyl)-1,2,4-oxadiazol-5-yl)phenyl)-1,2,4-oxadiazol-5(4H)-one (KJA-04)

White solid, m.p. 160.0~161.0° C.; IR (KBr): 3553, 3481, 3413, 3234, 1784, 1638, 1614, 1516, 1447, 1240, 1154, 845, 755, 613 cm$^{-1}$; $^1$H NMR (400 MHz, CDCl$_3$): δ=8.32~8.29 (m, 1H, ArH), 8.10~8.07 (m, 2H, ArH), 7.84~7.74 (m, 2H, ArH), 7.68~7.66 (m, 1H, ArH), 7.27~7.19 (m, 2H, ArH), 6.94 (d, J=8.8 Hz, 2H, ArH); $^{13}$C NMR (100 MHz, CDCl$_3$): δ=171.6, 168.1, 166.1, 165.8, 163.6, 158.2, 157.2, 134.3, 131.4, 131.1, 130.9, 130.7, 130.1, 130.0, 129.8, 129.7, 122.4, 122.3, 122.2, 119.3, 119.2, 116.6, 116.4, 116.2. HRMS (TOP ES$^+$): m/z calculated for C$_{22}$H$_{12}$F$_2$N$_4$O$_3$Na [M+Na]$^+$, 441.0770; found, 441.0772.

3-(4-Methoxyphenyl)-4-(2-(3-(4-methoxyphenyl)-1,2,4-oxadiazol-5-yl)phenyl)-1,2,4-oxadiazol-5(4H)-one (KJA-05)

White solid, m.p. 187.5~188.9° C.; IR (KBr): 3075, 2974, 2942, 2884, 2571, 1786, 1606, 1560, 1457, 1434, 1395, 1340, 1271, 1144, 1065, 1015, 883, 818, 758, 635 cm$^{-1}$; $^1$H NMR (400 MHz, CDCl$_3$): δ=8.19 (dd, J$_1$=1.6 Hz, J$_2$=8.0 Hz, 1H), 7.74~7.70 (m, 1H, ArH), 7.69~7.56 (m, 4H, ArH), 7.34~7.30 (m, 1H, ArH), 7.05~6.98 (m, 2H, ArH), 6.82~6.79 (m, 1H, ArH), 6.70~6.66 (m, 2H, ArH), 3.85 (s, 3H, OCH$_3$), 3.49 (s, 3H, OCH$_3$); $^{13}$C NMR (100 MHz, CDCl$_3$): δ=171.4, 168.9, 160.0, 159.6, 158.5, 158.0, 134.1, 131.3, 131.2, 130.9, 130.7, 130.2, 130.0, 127.2, 124.1, 122.4, 119.8, 118.7, 118.1, 112.7, 111.7, 55.5, 55.1. HRMS (TOP ES$^+$): m/z calculated for C$_{24}$H$_{18}$H$_4$O$_5$Na [M+Na]$^+$, 465.1168; found, 465.1172.

3-(4-Bromophenyl)-4-(2-(3-(4-bromophenyl)-1,2,4-oxadiazol-5-yl)phenyl)-1,2,4-oxadiazol-5(4H)-one (KJA-11)

Light yellow solid, m.p. 209.1~210.4° C.; IR (KBr): 3408, 1782, 1635, 1613, 1556, 1500, 1444, 1425, 1405, 1359, 1146, 1107, 1012, 837, 757, 625 cm$^{-1}$; $^1$H NMR (400 MHz, CDCl$_3$): δ=8.32 (d, J=8.0 Hz, 1H, ArH), 7.94 (d, J=8.0 Hz, 2H, ArH), 7.83 (t, J=7.6 Hz, 1H, ArH), 7.76 (t, J=7.6 Hz, 1H, ArH), 7.67 (d, J=8.0 Hz, 3H, ArH), 7.39 (d, J=8.0 Hz, 2H, ArH), 7.11 (d, J=8.0 Hz, 2H, ArH); $^{13}$C NMR (100 MHz, CDCl$_3$): δ=171.7, 168.3, 158.1, 157.2, 134.3, 132.5, 132.4, 131.5, 131.2, 131.0, 130.6, 129.0, 128.9, 126.9, 126.4, 124.9, 122.3, 122.0. HRMS (TOP ES$^+$): m/z calculated for C$_{22}$H$_{12}$Br$_2$N$_4$O$_3$Na [M+Na]$^+$, 560.9618; found, 560.9170.

3-(3-Fluorophenyl)-4-(2-(3-(3-fluorophenyl)-1,2,4-oxadiazol-5-yl)phenyl)-1,2,4-oxadiazol-5(4H)-one (KJA-07)

Light yellow solid, m.p. 163.1~164.4° C.; IR (KBr): 3563, 3472, 3400, 1784, 1640, 1593, 1502, 1447, 1410, 1226, 1113, 1096 1012, 837, 755, 603 cm$^{-1}$; $^1$H NMR (400 MHz, CDCl$_3$): δ=8.32 (d, J=7.6 Hz, 1H, ArH), 7.88~7.75 (m, 4H, ArH), 7.67 (dd, J$_1$=0.8 Hz, J$_2$=7.6 Hz, 1H, ArH), 7.51 (dd, J$_1$=8.0 Hz, J$_2$=13.6 Hz, 1H, ArH), 7.27~7.21 (m, 2H, ArH), 7.12~6.98 (m, 3H, ArH); $^{13}$C NMR (100 MHz, CDCl$_3$): δ=171.8, 168.2, 168.1, 164.1, 161.6, 161.1, 158.1, 156.8, 134.4, 131.5, 131.1, 131.0, 130.9, 130.7, 128.1, 128.0, 125.0, 124.9, 123.5, 123.4, 123.3, 123.2, 122.3, 119.3, 119.1, 118.9, 118.6, 114.0, 114.8, 114.3. HRMS (TOP ES$^+$): m/z calculated for C$_{22}$H$_{12}$F$_2$N$_4$O$_3$Na [M+Na]$^+$, 441.0770; found, 441.0769.

3-(2-Fluorophenyl)-4-(2-(3-(2-fluorophenyl)-1,2,4-oxadiazol-5-yl)phenyl)-1,2,4-oxadiazol-5(4H)-one (KJA-17)

Light yellow solid, m.p. 141.1~143.0° C.; IR (KBr): 3082, 1782, 1610, 1593, 1522, 1503, 1483, 1447, 1349, 1333, 1228, 1182, 1105, 1094, 910, 784, 766, 727 cm$^{-1}$; $^1$H NMR (400 MHz, CDCl$_3$): δ=8.26~8.24 (m, 1H, ArH), 8.15 (d, J=3.2 Hz, 1H, ArH), 7.76~7.73 (m, 1H, ArH), 7.67 (S, 2H, ArH), 7.55 (d, J=3.2 Hz, 1H, ArH), 7.42~7.36 (m, 2H, ArH), 7.31~7.24 (m, 2H, ArH), 7.07~7.04 (m, 1H, ArH), 7.00~6.95 (m, 1H, ArH); $^{13}$C NMR (100 MHz, CDCl$_3$): δ=171.3, 165.9, 165.8, 162.1, 160.8, 159.6, 158.3, 158.0, 155.4, 134.4, 134.3, 133.9, 133.3, 133.2, 131.2, 131.0, 130.9, 130.5, 130.2, 124.9, 122.0, 116.8, 116.6, 116.4, 116.2, 114.5, 114.4, 111.5, 111.3. HRMS (TOP ES$^+$): m/z calculated for C$_{22}$H$_{12}$F$_2$N$_4$O$_3$Na [M+Na]$^+$, 441.0770; found, 441.0770.

4-(4,5-Dimethoxy-2-(3-phenyl-1,2,4-oxadiazol-5-yl)phenyl)-3-phenyl-1,2,4-oxadiazol-5(4H)-one (KJA-06)

White solid, m.p. 210.7~211.2° C.; IR (KBr): 3389, 3070, 2936, 2850, 1783, 1607, 1552, 1520, 1445, 1357, 1275, 1229, 1165, 1016, 887, 798, 776, 753, 706 cm$^{-1}$; $^1$H NMR (400 MHz, CDCl$_3$): δ=8.03~8.01 (m, 2H, ArH), 7.81 (s, 1H, ArH), 7.68~7.63 (m, 4H, ArH), 7.47 (dd, J$_1$=6.4 Hz, J$_2$=9.6 Hz, 1H, ArH), 7.40~7.36 (m, 4H, ArH), 3.94 (s, 3H, OCH$_3$), 3.92 (s, 3H, OCH$_3$); $^{13}$C NMR (100 MHz, CDCl$_3$): δ=172.5, 168.5, 158.8, 153.5, 150.5, 132.5, 129.9, 129.5, 128.2, 127.4, 126.2, 123.3, 115.1, 114.0, 111.8, 57.1, 56.6. HRMS (TOP ES$^+$): m/z calculated for C$_{24}$H$_{18}$H$_4$O$_5$Na [M+Na]$^+$, 465.1169; found, 465.1173.

3-(4-Chlorophenyl)-4-(2-(3-(4-chlorophenyl)-1,2,4-oxadiazol-5-yl)-4,5-dimethoxyphenyl)-1,2,4-oxadiazol-5(4H)-one (KJA-09)

White solid, m.p. 246.4 246.7° C.; IR (KBr): 3444, 3348, 3068, 2942, 1796, 1603, 1553, 1509, 1431, 1408, 1368, 1349, 1226, 1090, 1013, 766, 756, 599 cm$^{-1}$; $^1$H NMR (400 MHz, CDCl$_3$): δ=7.99 (s, 2H, ArH), 7.66 (s, 1H, ArH), 7.49 (s, 2H, ArH), 7.23 (s, 4H, ArH), 7.09 (s, 1H, V), 4.02 (s, 6H, OCH$_3$); $^{13}$C NMR (100 MHz, CDCl$_3$): δ=171.7, 168.1, 158.4, 157.3, 153.5, 150.8, 138.4, 137.8, 129.4, 128.8, 128.7, 124.6, 124.4, 121.7, 114.8, 113.0, 111.5, 56.8, 56.6. HRMS (TOP ES$^+$): m/z calculated for C$_{24}$H$_{16}$N$_4$Cl$_2$O$_5$Na [M+Na]$^+$, 533.0390; found, 533.0387.

4-(4,5-Dimethoxy-2-(3-(p-tolyl)-1,2,4-oxadiazol-5-yl)phenyl)-3-(p-tolyl)-1,2,4-oxadiazol-5(4H)-one (KJA-08)

White solid, m.p. 185.6~186.7° C.; IR (KBr): 3008, 2928, 2852, 1780, 1604, 1569, 1523, 1453, 1431, 1414, 1376, 1259, 1223, 1021, 897, 849, 763, 755, 728 cm$^{-1}$; $^1$H NMR (400 MHz, CDCl$_3$): δ=7.97 (s, 2H, ArH), 7.64 (s, 1H, ArH), 7.32~7.03 (m, 7H, ArH), 4.02 (s, 6H, OCH$_3$), 2.42 (s, 3H, CH$_3$), 2.26 (s, 3H, CH$_3$); $^{13}$C NMR (100 MHz, CDCl$_3$): δ=171.4, 168.9, 158.7, 158.1, 153.1, 150.5, 142.4, 141.8, 129.7, 129.6, 127.5, 124.7, 123.5, 120.4, 115.2, 113.1, 111.5, 56.7, 56.5, 21.6, 21.4. HRMS (TOP ES$^+$): m/z calculated for C$_{26}$H$_{22}$N$_4$O$_5$Na [M+Na]$^+$, 493.1482; found, 493.1483.

3-(2-Chlorophenyl)-4-(2-(3-(2-chlorophenyl)-1,2,4-oxadiazol-5-yl)-4,5-dimethoxyphenyl)-1,2,4-oxadiazol-5(4H)-one (KJA-10)

White solid, m.p. 219.1 219.7° C.; IR (KBr): 3550, 3414, 3070, 2918, 2849, 1787, 1735, 1608, 1582, 1525, 1440, 1370, 1257, 1218, 1153, 1063, 996, 870, 756, 734 cm$^{-1}$; $^1$H NMR (400 MHz, CDCl$_3$): δ=8.31 (s, 1H, ArH), 8.10~7.95 (m, 2H, ArH), 7.79 (d, J=20.8 Hz, 2H, ArH), 7.67 (s, 1H, ArH), 7.27 (s, 1H, ArH), 7.08 (d, J=7.6 Hz, 2H, ArH), 6.74 (s, 1H, ArH), 3.98 (s, 3H, OCH$_3$), 3.82 (s, 3H, OCH$_3$); $^{13}$C NMR (100 MHz, CDCl$_3$): δ=171.5, 167.8, 158.3, 157.7, 157.6, 156.7, 134.2, 131.4, 131.1, 130.1, 130.7, 129.4, 129.2, 127.6, 127.5, 123.4, 122.5, 119.3, 115.9, 114.5, 112.2, 112.0, 56.3, 56.2. HRMS (TOP ES$^+$): m/z calculated for C$_{24}$H$_{16}$N$_4$Cl$_2$O$_5$Na [M+Na]$^+$, 533.0390; found, 533.0303.

Example II

MTT Assay

The evaluation of cytotoxicity was based on the reduction of MTT dye by viable cells to give purple formazan products, which can be measured spectrophotometrically at 540 nm. One hundred eighty microliters of cancer cells were seeded into 96-well plates at 3,500-4,000 cells/well and incubated at 37° C. overnight before the indicated treatments. After 72 h, 20 μl of MTT solution (3 mg/ml) was added and incubated again for 3 h. After removal of media and solubilization of formazan crystals in 150 μL of DMSO, the absorbance was measured at 570 nm. Percentage of cell growth inhibition was expressed as 1-[(A−B)/(C−B)]×100% (A, B and C were the absorbance values from experimental, blank and control cells, respectively).

Colony formation assay. Colony formation assay is an in vitro cell survival assay based on the ability of a single cell to grow into a colony. This technique was also performed to confirm the activity. Briefly, cells were plated in 96-well plates at a density of 300 cells/well and allowed to attach overnight. The next day, the corresponding compounds were added and allowed to incubate for 24 h. After exposure, cells were changed the new media and cultured until colonies were formed (7-10 days). Cells were subsequently washed and stained with a solution of crystal violet for 30 min. After staining, cells were thoroughly washed with water. Colonies were imaged on the inverted fluorescence microscope and were counted using ImageJ software.

KJA derivatives were tested by the MTT assay against five human cancer cell lines including ovarian cancer cell lines (OVCAR-8, NCI/ADR-RES and SKOV3) and pancreatic cancer cell lines (MIA PaCa-2 and Pac-1). According to Table 2, many of these compounds exhibited cytotoxicity with IC$_{50}$ values below 10 μM, whereas the most potent compound was KJA03 with IC$_{50}$ ranging about 0.13-0.31 μM against five cancer cell lines. It is important to note that the NCI/ADR-RES cell line shares a large number of karyotypic abnormalities with OVCAR-8 but expresses high levels of MDR1 (multidrug resistance protein 1)/P-glycoprotein (see, e.g., Xu, S.; et al., Proceedings of the National Academy of Sciences 2012, 109, 16348-16353), resulting in resistance to multiple anticancer drugs in clinical use, including paclitaxel and doxorubicin. In addition, KJA03 also significantly inhibited colony formation in NCI/ADR-RES at low concentration (FIG. 1C-D). These results suggested that KJA03 has potential ability to overcome drug resistant cancer cells.

TABLE 2

Cytotoxicity of KJA compounds in a panel of human cancer cell lines

| Compound | IC$_{50}$ (μM)* | | | | |
|---|---|---|---|---|---|
| | OVCAR8 | NCI/ADR-RES | SKOV3 | MIA PaCa-2 | Panc1 |
| KJA01 | 4.65 ± 2.05 | 4.31 ± 0.55 | 5.82 | 2.49 | 2.16 |
| KJA02 | 1.96 ± 0.42 | 4.16 ± 2.61 | 11.24 ± 7.01 | 1.12 | 1.51 |
| KJA03 | 0.14 ± 0.05 | 0.20 ± 0.06 | 0.31 ± 0.16 | 0.13 ± 0.01 | 0.17 |
| KJA04 | 7.21 ± 1.55 | 7.63 ± 3.01 | 20.95 ± 9.69 | 5.17 | 3.22 |
| KJA06 | >30 | >30 | >30 | >30 | >30 |
| KJA09 | >30 | >30 | >30 | >30 | >30 |
| KJA10 | 0.71 ± 0.08 | 2.00 ± 0.76 | 3.23 ± 0.37 | 0.71 | 1.08 |
| KJA12 | 24.01 ± 5.44 | 21.27 ± 7.38 | 7.64 | 5.95 | 4.15 |
| KJA14 | 1.28 ± 0.36 | 3.44 ± 2.29 | 6.09 ± 2.40 | 0.92 | 0.88 |
| KJA17 | 9.12 ± 0.88 | 9.42 ± 1.61 | 25.55 | 1.43 | 3.17 |
| Paclitaxel | <0.04 | >30 | NT | <0.04 | <0.04 |

NT, not tested
*IC$_{50}$ is defined as the drug concentration causing a 50% decrease in cell population.

Example III

Western Blotting

Cells (5×10$^5$) were cultured in 6-well plate and treated with KJA03 at designated concentrations. After treatment, cells were lysed with cell lysis buffer on ice at 4° C., sonicated for 3 min, centrifuged (12,000 rpm, 10 min, 4° C.) and then, the supernatant was collected. Protein concentrations of supernatants were evaluated with BCA assay. Proteins were resolved in 10% SDS/PAGE and electrotransferred to Immun-Blot PVDF membrane (Bio-Rad). After blocking with 5% milk in TBST (Tris-buffered saline with 0.1% Tween 20), membranes were probed with primary antibodies (anti-PARP, anti-caspase 3 and anti-GAPDH) 1:1000 dilutions overnight at 4° C. Membranes were then washed with TBST (5 min×3), incubated with Dylight 800-conjugated secondary antibodies 1:7500 dilutions in 5% milk for 1 h at room temperature, and washed with TBST (5 min×3). Fluorescent signal was then scanned by Odyssey Imaging Systems (LI-COR Biosciences).

Figure 2:
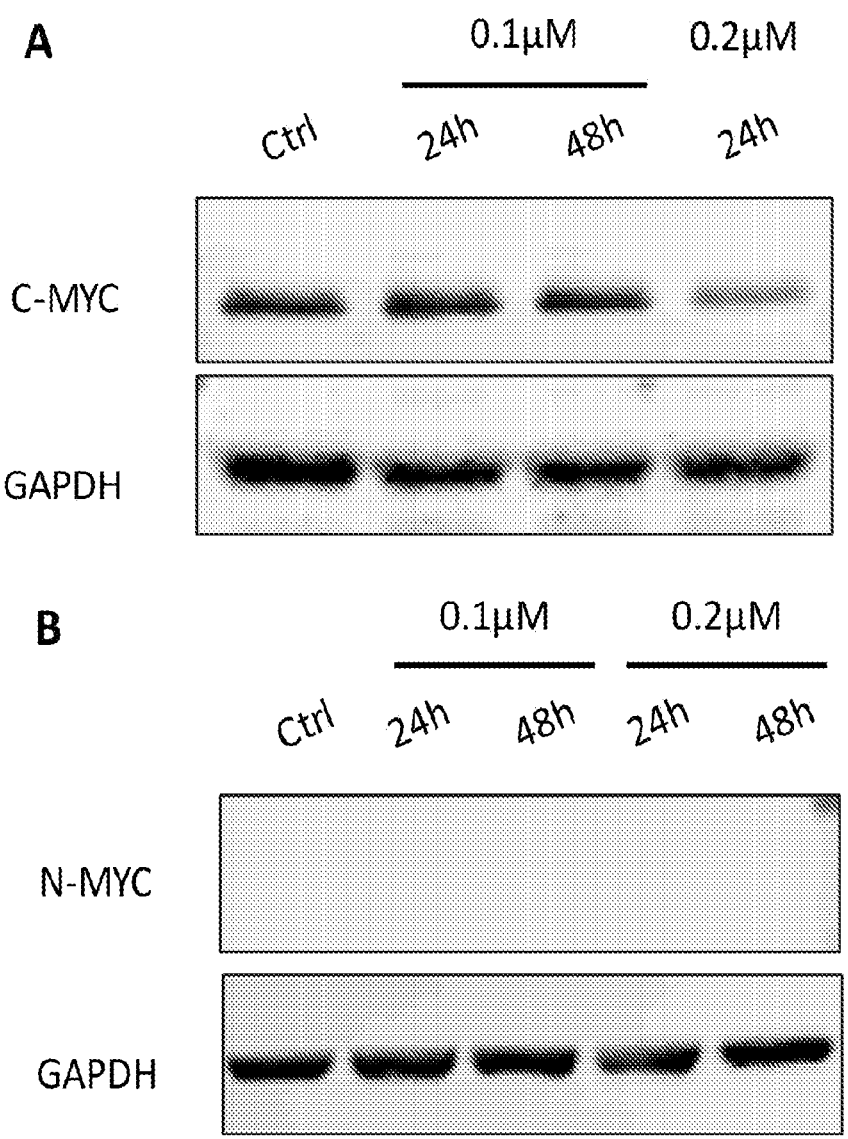
FIG. 2 The expression of (A) C-MYC and (B) N-MYC in NCI/ADR-RES cells treated with KJA03 at concentration of 0.1 and 0.2 μM for 24 and 48 h.

The effect of KJA03 on the MYC protein levels, including C-MYC and N-MYC, NCI/ADR-RES cells were treated with KJA03 at concentration of 0.1 (half IC$_{50}$) and 0.2 (IC$_{50}$) μM for 24 and 48 h. Interestingly, reduced C-MYC levels were observed within 24 h of treatment at concentration of 0.2 μM, while the levels of N-MYC protein cannot be detected as shown in FIG. 2. It has previously been reported that JQ1 treatment leads to down-regulation of c-MYC protein levels in osteosarcoma, leukemia and lymphoma cells (see, e.g., Mertz, J. A.; et al., Proceedings of the National Academy of Sciences 2011, 108, 16669-16674).

Figure 3:
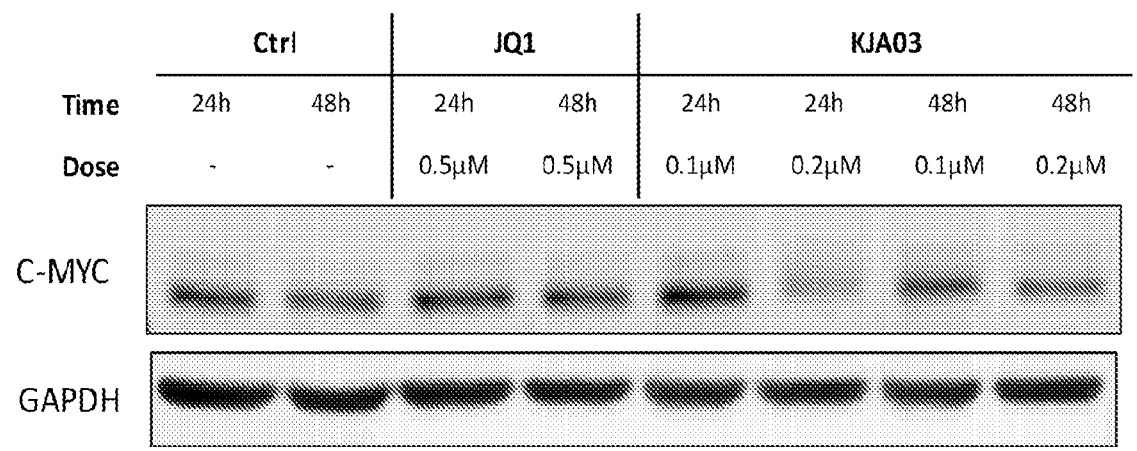
FIG. 3 The expression of C-MYC in NCI/ADR-RES cells treated with KJA03 at concentration of 0.1 and 0.2 μM for 24 and 48 h, using JQ1 as a positive control.

Experiments were conducted to further repeat the experiment and JQ1 was chosen as a positive control. As expected, expression of C-MYC was reduced by KJA03 at 24 h of treatment, correlated with previous experiment (FIG. 3). However, JQ1 did not inhibit C-MYC expression of NCI/ADR-RES cells at concentrations of 0.5 μM, consistent with previous studies. It was noted that JQ1 inhibits MYC expression in many cancer cells tested but does not inhibit MYC expression in some other cancer cell lines (see, e.g., Fowler, T.; et al., PLOS ONE 2014, 9, e87003). In summary, treatment with KJA03 at 0.2 μM for 24 h was able to efficiently decrease the C-MYC protein levels.

Figure 4:
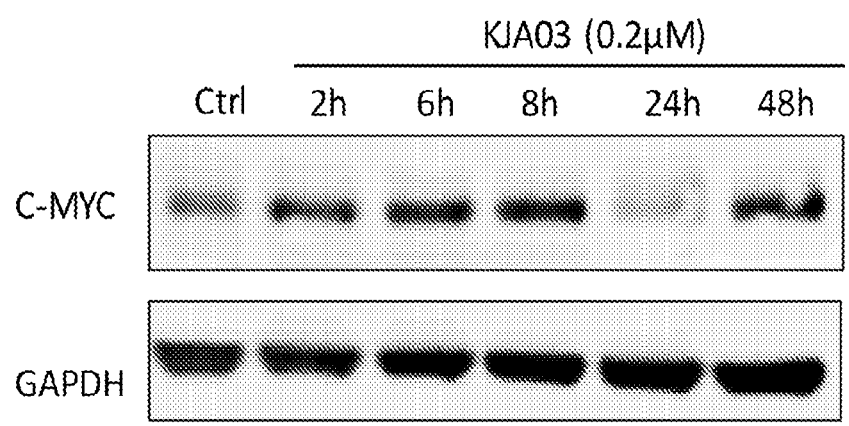
FIG. 4 The expression of C-MYC in NCI/ADR-RES cells treated with KJA03 at concentration of 0.2 μM at different time points.
Figure 5:
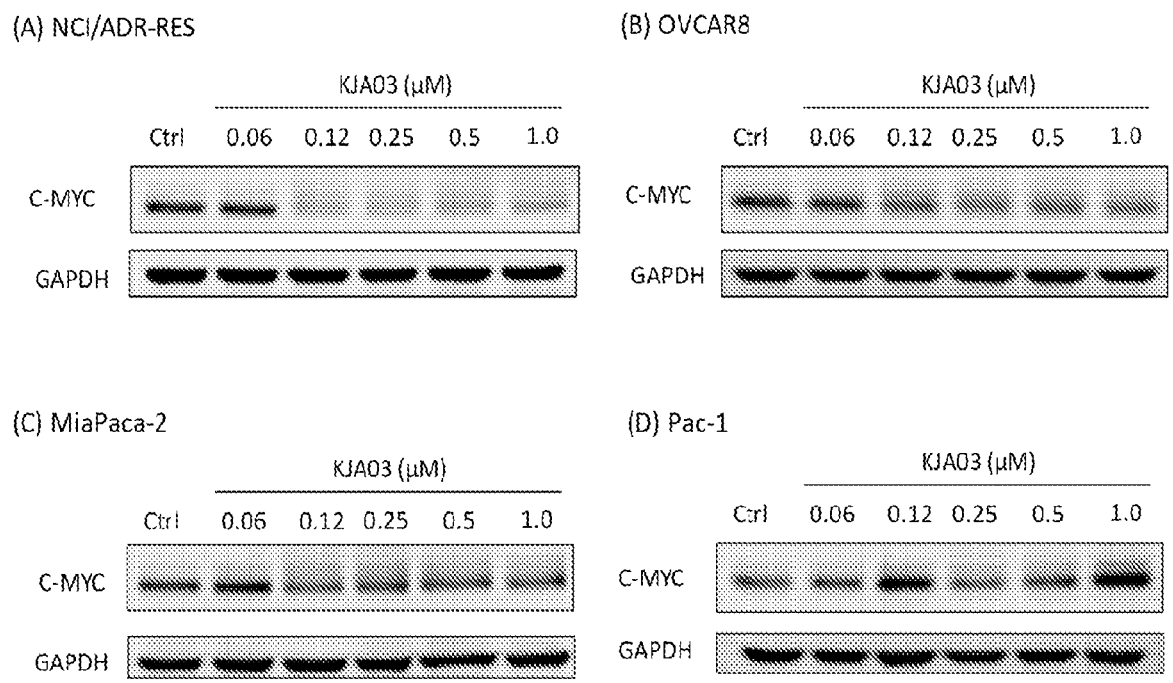
FIG. 5 C-MYC protein levels were down-regulated dose-dependently by KJA03 treatment in (A) NCI/ADR-RES, (B) OVCAR8, (C) MiaPaca-2 and (D) Pac-1.

Experiments were conducted that further performed a time-course experiment to evaluate C-MYC suppression including 2, 6, 8 24 and 48 h at concentration of 0.2 μM. Surprisingly, C-MYC was significantly suppressed only at 24 h of treatment with KJA03 as shown in FIG. 4. To define the specificity of MYC suppression in further detail, we treated cells with a range of compound concentrations at 24 h. The results in FIG. 5A showed that KJA03 decreased levels of C-MYC in a dose-dependent manner. To determine whether KJA03 can suppress C-MYC in different cell lines, we next investigated the level of C-MYC in response to treatment with KJA03 at 0.2 μM using other three different OVCAR8, MIA PaCa-2 and Panc-1 cell lines. We observed that KJA03 suppresses MYC strongly in ovarian cancer cells (OVCAR8 and NCI/ADR-RES) rather than pancreatic cancer cells as shown in FIG. 5A-5D.

Figure 6:
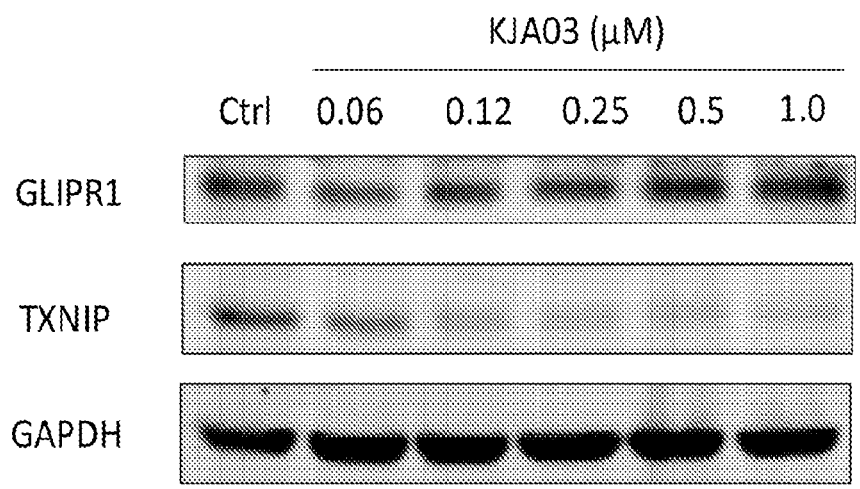
FIG. 6 GLIPR1 protein levels were up-regulated and TXNIP protein levels were down-regulated dose-dependently by KJA03 treatment in NCI/ADR-RES.
Figure 7:
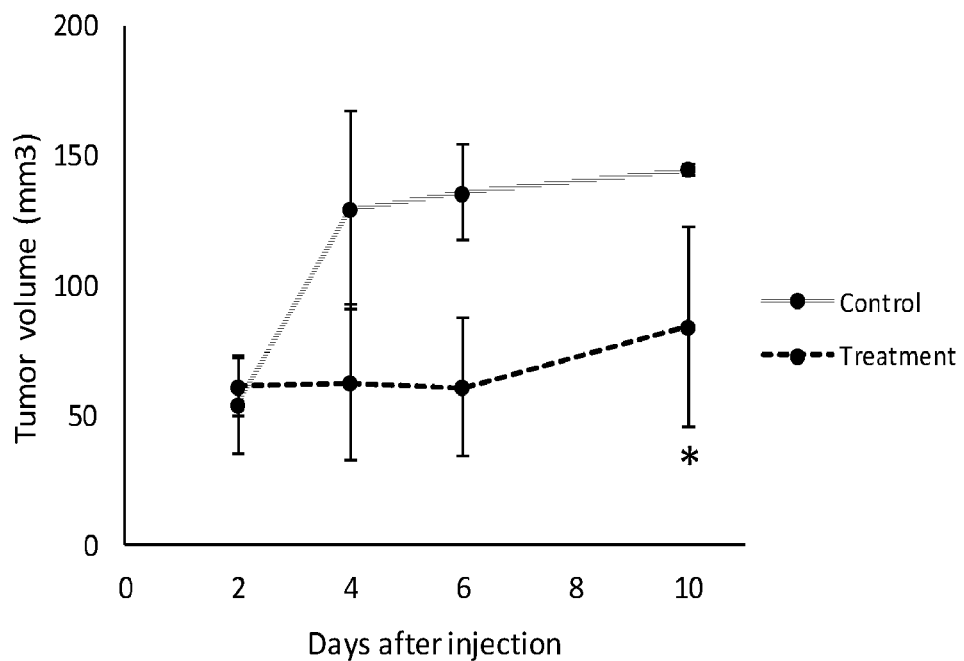
FIG. 7 (A) tumor sizes were reduced in mice treated with KJA03 (B) The body weight of mice treated with 10 mg/kg of KJA03, Statistical significance was calculated using t-test. Error bars indicate Mean±SEM. and *p<0.05.
Figure 7:
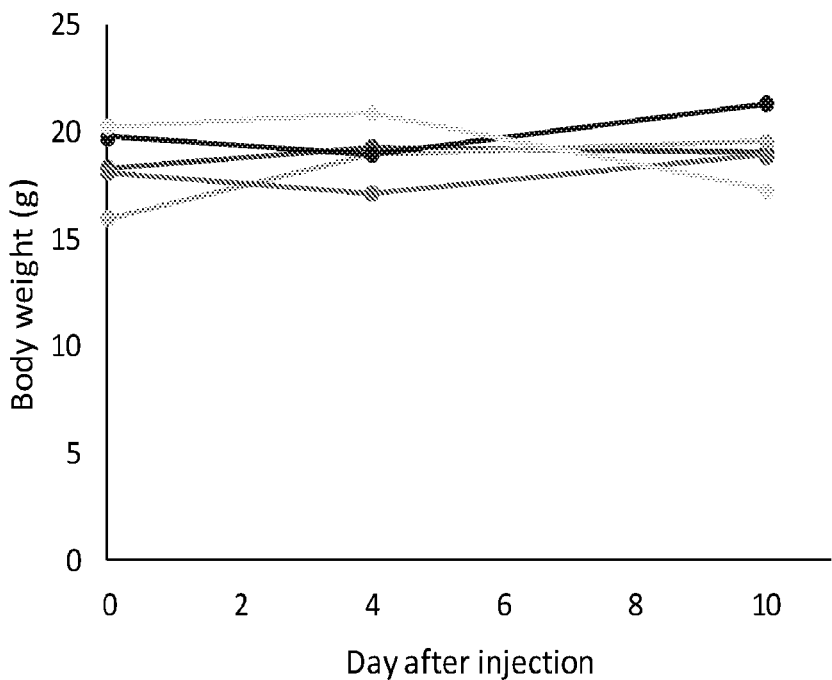

Furthermore, to better understand the potential mechanism of KJA03, we performed Bru-seq to examine the global changes in transcription in NCI/ADR-RES cells. According to the Western blot results (FIG. 6), we found that the expression levels of the GLIPR1 were gradually upregulated after KJA03 treatment. In contrast, TXNIP was down-regulated consistent with the findings from Bru-seq results.

Example IV

TABLE 3

Upregulated genes in NCI/ADR-RES cell line treated with KJA03 (0.4 uM for 4 hours; fold-change > 2.0).

| Gene Name | Fold-Change | Comment |
|---|---|---|
| LAMC2 | 3.217 | Laminin, gamma 2. Involved in the attachment, migration and organization of cells into tissues during embryonic development. |
| INGX | 3.089 | Inhibitor of growth family, X-linked (pseudogene). Involved in cell cycle regulation, DNA repair, apoptosis, senescence, chromatin remodeling, and transcriptional regulation. |
| TMEM133 | 2.846 | Transmembrane protein 133. Intronless gene. Gene function is unknown. |
| BHLHE40 | 2.683 | Basic helix-loop-helix family member e40. Involved in the control of circadian rhythm and cell differentiation. |
| TAGLN | 2.648 | Transgelin. Transformation and shape-change sensitive actin cross-linking/gelling protein found in fibroblasts and smooth muscle. |
| GLIPR1 | 2.574 | Glioma pathogenesis-related 1. Encodes protein with similarity to both the pathogenesis-related protein (PR) superfamily and the cysteine-rich secretory protein (CRISP) family. |
| ILE | 2.485 | Interleukin 6. Cytokine with a wide variety of biological functions. It is a potent inducer of the acute phase response. |

TABLE 3-continued

Upregulated genes in NCI/ADR-RES cell line treated with KJA03 (0.4 uM for 4 hours; fold-change > 2.0).

| Gene Name | Fold-Change | Comment |
| --- | --- | --- |
| CSRP1 | 2.335 | Cysteine and Glycine-Rich Protein 1. May be involved in regulatory processes important for development and cellular differentiation. |
| LSMD1 | 2.261 | N(Alpha)-Acetyltransferase 38, NatC Auxiliary Subunit. NatC complex which catalyzes acetylation of N-terminal methionine residues. |
| ACTC1 | 2.238 | Actin, alpha, cardiac muscle 1. Found in muscle tissues; major constituent of the contractile apparatus. |
| TNFAIP3 | 2.192 | Tumor necrosis factor, alpha-induced protein 3. Encodes zinc finger protein and ubiqitin-editing enzyme, shown to inhibit NF-kappa B activation as well as TNF-mediated apoptosis. |
| SLC4A4 | 2.18 | Solute carrier family 4 (sodium bicarbonate cotransporter), member 4. Involved in the regulation of bicarbonate secretion and absorption and intracellular pH. |
| LINC00312 | 2.165 | Long Intergenic Non-Protein Coding RNA 312. Estrogen receptor repressor. |
| RPL23AP32 | 2.141 | Ribosomal Protein L23a Pseudogene 32. Transcribed pseudogene of ribosomal protein L23a. |
| MYADM | 2.114 | Myeloid-associated differentiation marker. Expressed in multipotent progenitor cells. |
| LAMB3 | 2.089 | Laminin subunit beta 3. Serves as the beta chain in laminin-5. |
| LPP | 2.032 | LIM domain-Containing preferred translocation partner In lipoma. Localizes to the cell periphery in focal adhesions; may be involved in cell-cell adhesion and cell motility; may function as a transcriptional co-activator. |

TABLE 4

Downregulated genes in NCI/ADR-RES cell line treated with KJA03 (0.4 uM for 4 hours; fold-change < 0.5).

| Gene Name | Fold-Change | Comment |
| --- | --- | --- |
| SDPR | 0.497 | Serum deprivation-response protein. Calcium-independent phospholipid-binding protein whose expression increases in serum-starved cells; substrate for protein kinase C (PKC) phosphorylation. |
| ATP5I | 0.496 | ATP synthase subunit e, mitochondrial. Catalyzes ATP synthesis. |
| SCARNA17 | 0.496 | Small cajal body-specific RNA 17. Proposed to guide the modification of RNA polymerase II transcribed spliceosomal RNAs U1, U2, U4, U5 and U12. |
| HIST1H3G | 0.496 | Histone cluster 1 H3 family member G |
| MRPL41 | 0.496 | Mitochondrial ribosomal protein L41. Involved in mitochondrial translation and organelle biogenesis and maintenance. |
| LOC100630918 | 0.494 | *Homo sapiens* uncharacterized LOC100630918, long non-coding RNA. Promoter of MAT2A-antisense radiation induced circulating lncRNA (PARTICLE). |
| EXOSC4 | 0.493 | Exosome component 4. Non-catalytic component of the RNA exosome complex which has 3→5 exoribonuclease activity and participates in a multitude of cellular RNA processing and degradation events. |
| HOXA1 | 0.491 | Homeobox A1. Sequence-specific transcription factor, part of a developmental regulatory system. |
| RPS19BP1 | 0.49 | Ribosomal protein S19 binding protein I. Involved in cellular responses to heat stress and cellular senescence. |
| SCARNA10 | 0.487 | Small cajal body-specific RNA 10. Contains both C/D and H/ACA boxes and participates in both 2-prime-O-methylation and pseudouridylation of U5 snRNA. |
| HIST4H4 | 0.483 | Histone cluster 4 H4 |
| HIST1H2A1 | 0.483 | Histone cluster 1 H2A family member 1 |
| HOXC | 0.477 | Homeobox C. The homeobox genes encode a highly conserved family of transcription factors that play an important role in morphogenesis in all multicellular organisms. |
| HIST1H2AE | 0.471 | Histone cluster 1 H2A family member E |
| FJX1 | 0.469 | Four jointed box 1. Human ortholog of mouse and *Drosophila* four-jointed gene product; exact function of this gene in humans is not known. |
| SNRNP25 | 0.463 | Small nuclear ribonucleoprotein U11/U12 subunit 25. Encodes a 25K protein that is a component of the U12-type spliceosome. |
| PA2G4P4 | 0.463 | Proliferation-associated 2G4 pseudogene 4 |
| TUBB2B | 0.461 | Tubulin beta 2B class IIb. Major constituent of microtubules; plays critical role in proper axon guidance in both central and peripheral axon tracts. |

TABLE 4-continued

Downregulated genes in NCI/ADR-RES cell line treated with KJA03 (0.4 uM for 4 hours; fold-change < 0.5).

| Gene Name | Fold-Change | Comment |
| --- | --- | --- |
| TCEAL1 | 0.455 | Transcription elongation factor A like 1. May function as nuclear phosphoproteins that modulate transcription in a promoter context-dependent manner. |
| LINC00493 | 0.452 | Long intergenic non-protein coding RNA 493. Also known as small integral membrane protein 26 (SMIM26). |
| HIST1H2AG | 0.45 | Histone cluster 1 H2A family member G |
| HIST3H2BB | 0.446 | Histone cluster 3 H2B family member B |
| HIST1H2BL | 0.441 | Histone cluster 1 H2B family member L |
| HIST1H3B | 0.432 | Histone cluster 1 H3 family member B |
| MRPS26 | 0.432 | Mitochondrial ribosomal protein S26. Involved in mitochondrial translation and organelle biogenesis and maintenance. |
| ARMCX1 | 0.417 | Armadillo repeat containing, X-linked 1. Encodes a member of the ALEX family of proteins and may play a role in tumor suppression. |
| MRPL34 | 0.416 | Mitochondrial ribosomal protein L34. Involved in mitochondrial translation and viral mRNA translation. |
| HIST1H4L | 0.416 | Histone cluster 1 H4 family member L |
| HSD17B10 | 0.415 | Hydroxysteroid 17-beta dehydrogenase 10. Encodes 3-hydroxyacyl-CoA dehydrogenase type II, a member of the short-chain dehydrogenase/reductase superfamily. |
| AURKAIP1 | 0.413 | Aurora kinase A interacting protein 1. Involved in mitochondrial translation and organelle biogenesis and maintenance; negative regulator of Aurora-A kinase, by down-regulation through proteasome-dependent degradation. |
| SCARNA2 | 0.401 | Small cajal body-specific RNA 2. Predicted to guide specific 2'-O-methylation of U2 snRNA |
| HOXC4 | 0.4 | Homeobox C4. Transcription factor; plays an important role in morphogenesis in all multicellular organisms. |
| CNO | 0.395 | Protein cappuccino homolog. Intronless gene encodes a protein that may play a role in organelle biogenesis associated with melanosomes, platelet dense granules, and lysosomes. |
| SFTA1P | 0.387 | Surfactant associated 1, pseudogene. Long non-coding RNA. |
| SSSCA1 | 0.386 | Sjogren syndrome/scleroderma autoantigen 1. Might play a role in mitosis; antigenic molecule; could be a centromere-associated protein; may induce anti-centromere antibodies. |
| HIST1H2BN | 0.378 | Histone cluster 1 H2B family member N |
| C19orf33 | 0.378 | Chromosome 19 open reading frame 33; also known as hepatocyte growth factor activator inhibitor type 2-related small protein. Encoded protein is found primarily in the nucleus. |
| TPBG | 0.374 | Trophoblast glycoprotein. Encodes a leucine-rich transmembrane glycoprotein that may be involved in cell adhesion. |
| HIST1H2AB | 0.362 | Histone cluster 1 H2A family member B |
| GALNT4 | 0.356 | Polypeptide N-acetylgalactosaminyltransferase 4. Encodes a member of the UDP-N-acetyl-alpha-D-galactosamine: polypeptide N-acetylgalactosaminyltransferase (GalNAc-T) family of enzymes. GalNAc-Ts initiate mucin-type O-linked glycosylation in the Golgi apparatus. |
| HIST1H4C | 0.338 | Histone cluster 1 H4 family member C |
| HIST1H4H | 0.324 | Histone cluster 1 H4 family member H |
| HIST1H3F | 0.322 | Histone cluster 1 H3 family member F |
| TWIST1 | 0.319 | Twist family BHLH transcription factor 1. bHLH transcription factor implicated in cell lineage determination and differentiation. |
| APOBEC3 | 0.309 | Apolipoprotein B mRNA editing enzyme, catalytic polypeptide-like 3. Also known as mitochondrial small ribosomal subunit protein mS38. |
| HIST2H2AC | 0.29 | Histone cluster 2 H2A family member C |
| TXNIP | 0.281 | Thioredoxin-interacting protein. Thiol-oxidoreductase that is a major regulator of cellular redox signaling which protects cells from oxidative stress. |
| EGR1 | 0.198 | Early growth response 1. Nuclear protein; functions as a transcriptional regulator. |
| HIST1H2BM | 0.193 | Histone cluster 1 H2B family member M |
| HIST1H3H | 0.136 | Histone cluster 1 H3 family member H |

TABLE 5

DAVID analysis output of the 25 most upregulated KEGG pathways in NCI/ADR-RES cell line treated with KJA03 (0.4 uM; 4 hours).

| Term | P-Value | FDR |
| --- | --- | --- |
| hsa05200: Pathways in cancer | 9.73E−14 | 1.10E−10 |
| hsa05146: Amoebiasis | 4.97E−13 | 5.63E−10 |
| hsa04510: Focal adhesion | 6.91E−11 | 7.84E−08 |
| hsa01100: Metabolic pathways | 2.14E−10 | 2.43E−07 |

TABLE 5-continued

DAVID analysis output of the 25 most upregulated KEGG pathways in NCI/ADR-RES cell line treated with KJA03 (0.4 uM; 4 hours).

| Term | P-Value | FDR |
| --- | --- | --- |
| hsa05166: HTLV-I infection | 5.20E−10 | 5.90E−07 |
| hsa04668: TNF signaling pathway | 1.66E−09 | 1.88E−06 |
| hsa05410: Hypertrophic cardiomyopathy (HCM) | 6.30E−08 | 7.14E−05 |
| hsa04060: Cytokine-cytokine receptor interaction | 1.32E−07 | 1.50E−04 |
| hsa05145: Toxoplasmosis | 3.66E−07 | 4.15E−04 |
| hsa05222: Small cell lung cancer | 5.02E−07 | 5.69E−04 |
| hsa04610: Complement and coagulation cascades | 1.29E−06 | 1.46E−03 |
| hsa04068: FoxO signaling pathway | 1.75E−06 | 1.99E−03 |
| hsa04640: Hematopoietic cell lineage | 4.73E−06 | 5.36E−03 |
| hsa04151: PI3K-Akt signaling pathway | 8.29E−06 | 9.39E−03 |
| hsa00330: Arginine and proline metabolism | 9.02E−06 | 1.02E−02 |
| hsa05414: Dilated cardiomyopathy | 1.80E−05 | 2.04E−02 |
| hsa05323: Rheumatoid arthritis | 1.98E−05 | 2.25E−02 |
| hsa04621: NOD-like receptor signaling pathway | 2.37E−05 | 2.68E−02 |
| hsa04512: ECM-receptor interaction | 2.37E−05 | 2.68E−02 |
| hsa05142: Chagas disease (*American trypanosomiasis*) | 7.72E−05 | 8.74E−02 |
| hsa04350: TGF-beta signaling pathway | 9.63E−05 | 1.09E−01 |
| hsa04520: Adherens junction | 9.63E−05 | 1.09E−01 |
| hsa05152: Tuberculosis | 1.77E−04 | 2.00E−01 |
| hsa05161: Hepatitis B | 2.42E−04 | 2.74E−01 |
| hsa05168: Herpes simplex infection | 3.62E−04 | 4.10E−01 |

*FDR = False Discovery Rate.

TABLE 6

DAVID analysis output of the 25 most downregulated KEGG pathways in NCI/ADR-RES cell line treated with KJA03 (0.4 uM; 4 hours).

| Term | P-Value | FDR |
| --- | --- | --- |
| hsa05322: Systemic lupus erythematosus | 5.27E−63 | 5.68E−60 |
| hsa05034: Alcoholism | 7.55E−59 | 8.14E−56 |
| hsa03010: Ribosome | 2.51E−27 | 2.70E−24 |
| hsa05203: Viral carcinogenesis | 2.44E−20 | 2.64E−17 |
| hsa05202: Transcriptional misregulation in cancer | 3.64E−20 | 3.93E−17 |
| hsa01100: Metabolic pathways | 5.10E−20 | 5.50E−17 |
| hsa00190: Oxidative phosphorylation | 7.63E−09 | 8.22E−06 |
| hsa05010: Alzheimer's disease | 1.56E−08 | 1.68E−05 |
| hsa04742: Taste transduction | 4.15E−08 | 4.48E−05 |
| hsa04932: Non-alcoholic fatty liver disease (NAFLD) | 8.20E−07 | 8.85E−04 |
| hsa05016: Huntington's disease | 2.54E−06 | 2.73E−03 |
| hsa03008: Ribosome biogenesis in eukaryotes | 1.27E−05 | 1.37E−02 |
| hsa04145: Phagosome | 1.34E−05 | 1.44E−02 |
| hsa05012: Parkinson's disease | 4.17E−05 | 4.49E−02 |
| hsa04260: Cardiac muscle contraction | 2.00E−04 | 2.16E−01 |
| hsa05130: Pathogenic *Escherichia coli* infection | 2.76E−04 | 2.97E−01 |
| hsa04540: Gap junction | 2.76E−04 | 2.97E−01 |
| hsa00230: Purine metabolism | 1.88E−03 | 2.01E+00 |
| hsa03013: RNA transport | 3.89E−03 | 4.11E+00 |
| hsa00630: Glyoxylate and dicarboxylate metabolism | 1.20E−02 | 1.22E+01 |
| hsa03410: Base excision repair | 1.62E−02 | 1.62E+01 |
| hsa04612: Antigen processing and presentation | 1.69E−02 | 1.68E+01 |
| hsa05134: Legionellosis | 1.76E−02 | 1.74E+01 |
| hsa03050: Proteasome | 2.66E−02 | 2.53E+01 |
| hsa00970: Aminoacyl-tRNA biosynthesis | 2.73E−02 | 2.58E+01 |

*FDR = False Discovery Rate.

TABLE 7

GSEA output of the 25 most unregulated hallmark pathways in NCI/ADR-RES cell line treated with KJA03 (0.4 uM; 4 hours).

| Pathway | NES | FDR q-val | FWER p-val |
| --- | --- | --- | --- |
| HALLMARK_EPITHELIAL_MESENCHYMAL_TRANSITION | 2.77 | 0.00 | 0.00 |
| HALLMARK_APICAL_JUNCTION | 2.24 | 0.00 | 0.00 |
| HALLMARK_TNFA_SIGNALING_VIA_NFKB | 2.22 | 0.00 | 0.00 |
| HALLMARK_INFLAMMATORY_RESPONSE | 2.14 | 0.00 | 0.00 |
| HALLMARK_UV_RESPONSE_DN | 2.09 | 0.00 | 0.00 |
| HALLMARK_COMPLEMENT | 2.07 | 0.00 | 0.00 |
| HALLMARK_ANDROGEN_RESPONSE | 2.05 | 0.00 | 0.00 |
| HALLMARK_MYOGENESIS | 1.98 | 0.00 | 0.00 |
| HALLMARK_HYPOXIA | 1.84 | 0.00 | 0.01 |
| HALLMARK_COAGULATION | 1.77 | 0.00 | 0.02 |
| HALLMARK_MITOTIC_SPINDLE | 1.76 | 0.00 | 0.02 |
| HALLMARK_ALLOGRAFT_REJECTION | 1.75 | 0.00 | 0.03 |
| HALLMARK_KRAS_SIGNALING_UP | 1.71 | 0.01 | 0.04 |
| HALLMARK_IL2_STAT5_SIGNALING | 1.64 | 0.01 | 0.07 |
| HALLMARK_TGF_BETA_SIGNALING | 1.63 | 0.01 | 0.08 |
| HALLMARK_CHOLESTEROL_HOMEOSTASIS | 1.52 | 0.03 | 0.18 |
| HALLMARK_KRAS_SIGNALING_DN | 1.49 | 0.03 | 0.22 |
| HALLMARK_HEME_METABOLISM | 1.47 | 0.04 | 0.26 |
| HALLMARK_ESTROGEN_RESPONSE_EARLY | 1.46 | 0.04 | 0.28 |
| HALLMARK_IL6_JAK_STAT3_SIGNALING | 1.43 | 0.05 | 0.34 |
| HALLMARK_ESTROGEN_RESPONSE_LATE | 1.38 | 0.06 | 0.44 |
| HALLMARK_INTERFERON_GAMMA_RESPONSE | 1.35 | 0.07 | 0.53 |
| HALLMARK_PEROXISOME | 1.24 | 0.15 | 0.80 |
| HALLMARK_BILE_ACID_METABOLISM | 1.20 | 0.18 | 0.87 |
| HALLMARK_PROTEIN_SECRETION | 1.08 | 0.35 | 0.99 |

*NES = Normalized Enrichment Score; FDR = False Discovery Rate; FWER = Family-Wise Error Rate.

TABLE 8

GSEA output of the most downregulated hallmark pathways in NCI/ADR-RES cell line treated with KJA03 (0.4 uM; 4 hours).

| Pathway | NES | FDR q-val | FWER p-val |
| --- | --- | --- | --- |
| HALLMARK_OXIDATIVE_PHOSPHORYLATION | −1.90 | 0.00 | 0.01 |
| HALLMARK_MYC_TARGETS_V2 | −1.81 | 0.00 | 0.02 |
| HALLMARK_MYC_TARGETS_V1 | −1.77 | 0.01 | 0.03 |
| HALLMARK_INTERFERON_ALPHA_RESPONSE | −1.55 | 0.06 | 0.35 |
| HALLMARK_DNA_REPAIR | −1.47 | 0.08 | 0.52 |
| HALLMARK_P53_PATHWAY | −1.41 | 0.11 | 0.72 |
| HALLMARK_NOTCH_SIGNALING | −1.32 | 0.19 | 0.93 |
| HALLMARK_E2F_TARGETS | −1.28 | 0.22 | 0.97 |
| HALLMARK_UNFOLDED_PROTEIN_RESPONSE | −1.18 | 0.38 | 1.00 |
| HALLMARK_REACTIVE_OXIGEN_SPECIES_PATHWAY | −1.14 | 0.43 | 1.00 |
| HALLMARK_ADIPOGENESIS | −1.11 | 0.44 | 1.00 |
| HALLMARK_GLYCOLYSIS | −0.96 | 0.77 | 1.00 |
| HALLMARK_APOPTOSIS | −0.91 | 0.82 | 1.00 |
| HALLMARK_UV_RESPONSE_UP | −0.91 | 0.77 | 1.00 |
| HALLMARK_FATTY_ACID_METABOLISM | −0.88 | 0.77 | 1.00 |
| HALLMARK_PI3K_AKT_MTOR_SIGNALING | −0.87 | 0.74 | 1.00 |
| HALLMARK_G2M_CHECKPOINT | −0.84 | 0.75 | 1.00 |

*NES = Normalized Enrichment Score; FDR = False Discovery Rate; FWER = Family-Wise Error Rate.

TABLE 9

GSEA showing top 25 gene sets sharing similarities with transcriptionally induced genes in NCI/ADR-RES cell line treated with KJA03 (0.4 uM; 4 hours).

| Gene Set | NES | FDR q-val | FWER p-val |
| --- | --- | --- | --- |
| ZWANG_CLASS_3_TRANSIENTLY_INDUCED_BY_EGF | 2.78 | 0.00 | 0.00 |
| ZHANG_RESPONSE_TO_IKK_INHIBITOR_AND_TNF_UP | 2.64 | 0.00 | 0.00 |
| GSE2706_UNSTIM_VS_2H_LPS_AND_R848_DC_DN | 2.62 | 0.00 | 0.00 |
| GSE26495_NAIVE_VS_PD1HIGH_CD8_TCELL_DN | 2.58 | 0.00 | 0.00 |
| GSE2706_UNSTIM_VS_2H_LPS_DC_DN | 2.54 | 0.00 | 0.00 |
| GSE2706_UNSTIM_VS_8H_LPS_DC_DN | 2.53 | 0.00 | 0.00 |
| KIM_WT1_TARGETS_UP | 2.44 | 0.00 | 0.00 |
| GSE26495_NAIVE_VS_PD1LOW_CD8_TCELL_DN | 2.42 | 0.00 | 0.00 |
| ZHOU_INFLAMMATORY_RESPONSE_LIVE_UP | 2.41 | 0.00 | 0.00 |
| SWEET_KRAS_TARGETS_UP | 2.39 | 0.00 | 0.00 |
| CHARAFE_BREAST_CANCER_LUMINAL_VS_MESENCHYMAL_DN | 2.38 | 0.00 | 0.00 |
| GSE2706_UNSTIM_VS_8H_R848_DC_DN | 2.36 | 0.00 | 0.00 |
| LIM_MAMMARY_STEM_CELL_UP | 2.36 | 0.00 | 0.00 |
| GSE2706_UNSTIM_VS_2H_R848_DC_DN | 2.35 | 0.00 | 0.00 |
| GSE360_L_DONOVANI_VS_B_MALAYI_LOW_DOSE_DC_UP | 2.34 | 0.00 | 0.00 |
| MODULE_5 | 2.34 | 0.00 | 0.00 |
| VART_KSHV_INFECTION_ANGIOGENIC_MARKERS_UP | 2.34 | 0.00 | 0.00 |
| RASHI_RESPONSE_TO_IONIZING_RADIATION_2 | 2.34 | 0.00 | 0.00 |
| MODULE_524 | 2.34 | 0.00 | 0.00 |
| PHONG_TNF_RESPONSE_VIA_P38_PARTIAL | 2.33 | 0.00 | 0.00 |
| FOSTER_TOLERANT_MACROPHAGE_DN | 2.32 | 0.00 | 0.00 |
| ZHOU_INFLAMMATORY_RESPONSE_FIMA_UP | 2.32 | 0.00 | 0.00 |
| PHONG_TNF_RESPONSE_NOT_VIA_P38 | 2.31 | 8.75E−05 | 1.00E−03 |
| GSE360_L_MAJOR_VS_B_MALAYI_HIGH_DOSE_MAC_UP | 2.31 | 8.38E−05 | 1.00E−03 |
| ZWANG_CLASS_1_TRANSIENTLY_INDUCED_BY_EGF | 2.30 | 8.05E−05 | 1.00E−03 |

*NES = Normalized Enrichment Score; FDR = False Discovery Rate; FWER = Family-Wise Error Rate.

TABLE 10

GSEA showing top 25 gene sets sharing similarities with transcriptionally induced genes in NCI/ADR-RES cell line treated with KJA03 (0.4 uM; 4 hours).

| Gene Set | NES | FDR q-val | FWER p-val |
| --- | --- | --- | --- |
| KEGG_RIBOSOME | −2.83 | 0.00 | 0.00 |
| REACTOME_PEPTIDE_CHAIN_ELONGATION | −2.81 | 0.00 | 0.00 |
| REACTOME_INFLUENZA_VIRAL_RNA_TRANSCRIPTION_AND_REPLICATION | −2.76 | 0.00 | 0.00 |
| STRUCTURAL_CONSTITUENT_OF_RIBOSOME | −2.75 | 0.00 | 0.00 |
| REACTOME_3_UTR_MEDIATED_TRANSLATIONAL_REGULATION | −2.73 | 0.00 | 0.00 |
| REACTOME_NONSENSE_MEDIATED_DECAY_ENHANCED_BY_THE_EXON_JUNCTION_COMPLEX | −2.70 | 0.00 | 0.00 |

TABLE 10-continued

GSEA showing top 25 gene sets sharing similarities with transcriptionally induced genes in NCI/ADR-RES cell line treated with KJA03 (0.4 uM; 4 hours).

| Gene Set | NES | FDR q-val | FWER p-val |
|---|---|---|---|
| REACTOME_SRP_DEPENDENT_COTRANSLATIONAL_PROTEIN_TARGETING_TO_MEMBRANE | −2.69 | 0.00 | 0.00 |
| GNF2_EIF3S6 | −2.62 | 0.00 | 0.00 |
| REACTOME_TRANSLATION | −2.61 | 0.00 | 0.00 |
| MARTENS_TRETINOIN_RESPONSE_DN | −2.60 | 0.00 | 0.00 |
| MORF_TPT1 | −2.59 | 0.00 | 0.00 |
| REACTOME_INFLUENZA_LIFE_CYCLE | −2.57 | 0.00 | 0.00 |
| GCM_TPT1 | −2.52 | 0.00 | 0.00 |
| MODULE_114 | −2.50 | 4.05E−05 | 1.00E−03 |
| MODULE_151 | −2.50 | 3.78E−05 | 1.00E−03 |
| GNF2_TPT1 | −2.48 | 3.54E−05 | 1.00E−03 |
| MORF_ACTG1 | −2.48 | 3.33E−05 | 1.00E−03 |
| GNF2_FBL | −2.47 | 3.15E−05 | 1.00E−03 |
| MORF_NME2 | −2.47 | 2.98E−05 | 1.00E−03 |
| MODULE_83 | −2.46 | 2.83E−05 | 1.00E−03 |
| BILANGES_SERUM_AND_RAPAMYCIN_SENSITIVE_GENES | −2.44 | 2.70E−05 | 1.00E−03 |
| MORF_NPM1 | −2.41 | 2.57E−05 | 1.00E−03 |
| GCM_NPM1 | −2.40 | 2.46E−05 | 1.00E−03 |
| REACTOME_METABOLISM_OF_MRNA | −2.38 | 2.36E−05 | 1.00E−03 |
| GNF2_DAP3 | −2.38 | 2.27E−05 | 1.00E−03 |

*NES = Normalized Enrichment Score; FDR = False Discovery Rate; FWER = Family-Wise Error Rate.

TABLE 11

CMAP results showing top 20 bioactive small molecules that share similar transcriptional expression pattern with NCI/ADR-RES cell line treated with 0.4 uM KJA03 for 4 hours.

| Rank | CMAP Name | Mean | n | Enrichment | p-value | Specificity | Percent Non-null |
|---|---|---|---|---|---|---|---|
| 1 | Rotenone | 0.75 | 4 | 0.95 | 0.00 | 0.00 | 100 |
| 2 | Mebendazole | 0.68 | 5 | 0.93 | 2.00E−05 | 0.00 | 100 |
| 3 | Fenbufen | −0.40 | 6 | −0.78 | 1.80E−04 | 0.00 | 66 |
| 4 | Diloxanide | −0.51 | 4 | −0.89 | 2.60E−04 | 0.00 | 100 |
| 5 | Spiradoline | −0.63 | 4 | −0.87 | 5.80E−04 | 0.00 | 100 |
| 6 | Butirosin | −0.52 | 4 | −0.85 | 8.20E−04 | 0.00 | 100 |
| 7 | Clofilium tosylate | 0.67 | 3 | 0.91 | 1.52E−03 | 5.60E−03 | 100 |
| 8 | Betulin | −0.52 | 3 | −0.90 | 1.90E−03 | 1.30E−02 | 100 |
| 9 | Benzydamine | 0.54 | 4 | 0.82 | 2.19E−03 | 1.33E−02 | 100 |
| 10 | Miconazole | 0.53 | 5 | 0.75 | 2.36E−03 | 0.00 | 80 |
| 11 | Puromycin | 0.71 | 4 | 0.81 | 2.37E−03 | 1.35E−01 | 100 |
| 12 | Fenbendazole | 0.76 | 4 | 0.81 | 2.65E−03 | 0.00 | 100 |
| 13 | Sulfaphenazole | −0.28 | 4 | −0.81 | 2.82E−03 | 5.00E−03 | 50 |
| 14 | Ciclopirox | 0.55 | 4 | 0.80 | 3.12E−03 | 4.83E−03 | 100 |
| 15 | CP-320650-01 | −0.30 | 8 | −0.59 | 3.79E−03 | 7.91E−02 | 75 |
| 16 | Betahistine | 0.54 | 4 | 0.79 | 3.94E−03 | 1.46E−02 | 100 |
| 17 | AG-013608 | −0.29 | 8 | −0.58 | 4.63E−03 | 0.00 | 62 |
| 18 | STOCK1N-35215 | 0.64 | 3 | 0.86 | 4.81E−03 | 5.60E−03 | 100 |
| 19 | (+)-Chelidonine | 0.52 | 4 | 0.77 | 4.95E−03 | 0.00 | 100 |
| 20 | Benzbromarone | −0.50 | 3 | −0.85 | 6.71E−03 | 6.30E−03 | 100 |

*Fold-change > 2.0

TABLE 12

MAP results showing top 20 bioactive small molecules that share similar transcriptional expression pattern with NCI/ADR-RES cell line treated with 0.4 uM KJA03 for 4 hours.

| Rank | CMAP Name | Mean | n | Enrichment | p-value | Specificity | Percent Non-null |
|---|---|---|---|---|---|---|---|
| 1 | Mebendazole | 0.68 | 5 | 0.96 | 0.00 | 0.00 | 100 |
| 2 | Trichostatin A | 0.43 | 182 | 0.53 | 0.00 | 2.42E−01 | 80 |
| 3 | LY-294002 | 0.23 | 61 | 0.29 | 0.00 | 3.69E−01 | 62 |
| 4 | Guaifenesin | −0.49 | 6 | −0.83 | 6.00E−05 | 0.00 | 83 |
| 5 | Withaferin A | 0.51 | 4 | 0.91 | 8.00E−05 | 5.79E−02 | 100 |
| 6 | Thioridazine | 0.38 | 20 | 0.50 | 8.00E−05 | 2.60E−01 | 70 |
| 7 | MG-262 | 0.64 | 3 | 0.96 | 1.00E−04 | 7.57E−02 | 100 |
| 8 | Puromycin | 0.71 | 4 | 0.90 | 1.00E−04 | 7.30E−02 | 100 |

TABLE 12-continued

MAP results showing top 20 bioactive small molecules that share similar transcriptional expression pattern with NCI/ADR-RES cell line treated with 0.4 uM KJA03 for 4 hours.

| Rank | CMAP Name | Mean | n | Enrichment | p-value | Specificity | Percent Non-null |
|------|-----------|------|---|------------|---------|-------------|------------------|
| 9 | Ciclopirox | 0.51 | 4 | 0.90 | 1.00E−04 | 2.90E−02 | 100 |
| 10 | Fluphenazine | 0.21 | 18 | 0.50 | 1.00E−04 | 8.29E−02 | 50 |
| 11 | Trifluoperazine | 0.38 | 16 | 0.51 | 1.80E−04 | 1.83E−01 | 75 |
| 12 | Bepridil | 0.50 | 4 | 0.88 | 2.00E−04 | 0.00 | 100 |
| 13 | Fenbendazole | 0.65 | 4 | 0.88 | 2.40E−04 | 0.00 | 100 |
| 14 | Niclosamide | 0.61 | 5 | 0.84 | 2.40E−04 | 1.05E−02 | 100 |
| 15 | Pyrvinium | 0.54 | 6 | 0.78 | 2.80E−04 | 5.58E−02 | 100 |
| 16 | Nocodazole | 0.50 | 6 | 0.76 | 4.80E−04 | 5.30E−03 | 83 |
| 17 | Betulin | −0.53 | 3 | −0.93 | 5.00E−04 | 0.00 | 100 |
| 18 | Gossypol | 0.45 | 6 | 0.75 | 5.40E−04 | 1.67E−02 | 100 |
| 19 | Solanine | 0.56 | 4 | 0.85 | 6.20E−04 | 0.00 | 100 |
| 20 | Sirolimus | 0.23 | 44 | 0.30 | 7.20E−04 | 3.37E−01 | 59 |

*Fold-change >1.5

Example V

Figure 8C:
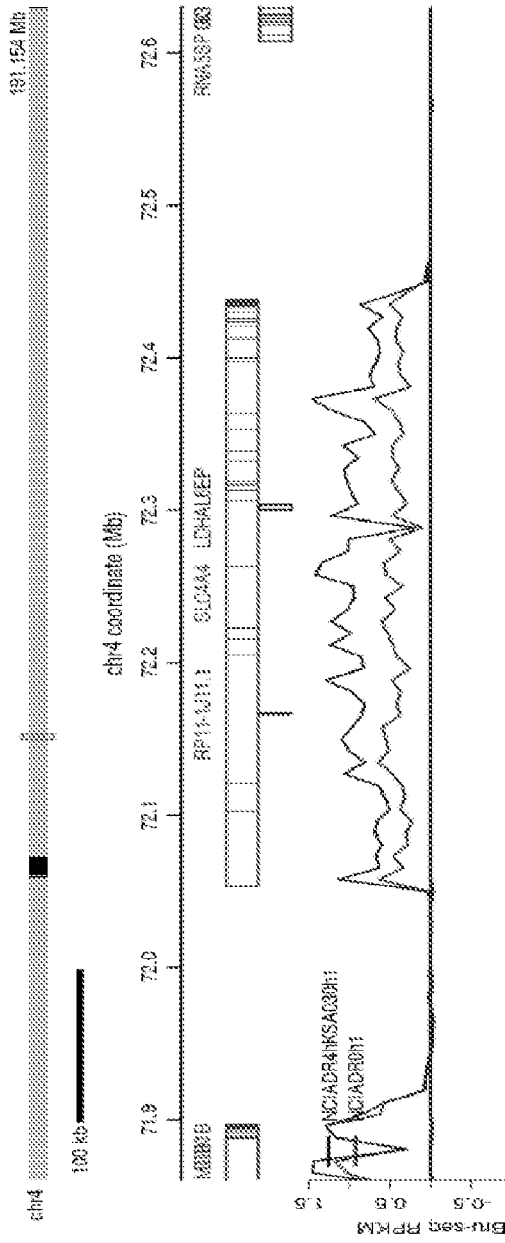
FIG. 8. Genes transcriptionally induced by KJA03 treatment (0.4 uM; 4 hours). (A) The synthesis of the LAMC2 gene is induced 3.217-fold following KJA03 treatment. (B) The synthesis of the CSRP1 gene is induced 3.335-fold following KJA03 treatment. (C) The synthesis of the SLC4A4 gene is induced 2.18-fold following KJA03 treatment. (D) The synthesis of the LAMB3 gene is induced 2.089-fold following KJA03 treatment. (E) The synthesis of the LPP gene is induced 2.032-fold following KJA03 treatment.
Figure 8D:
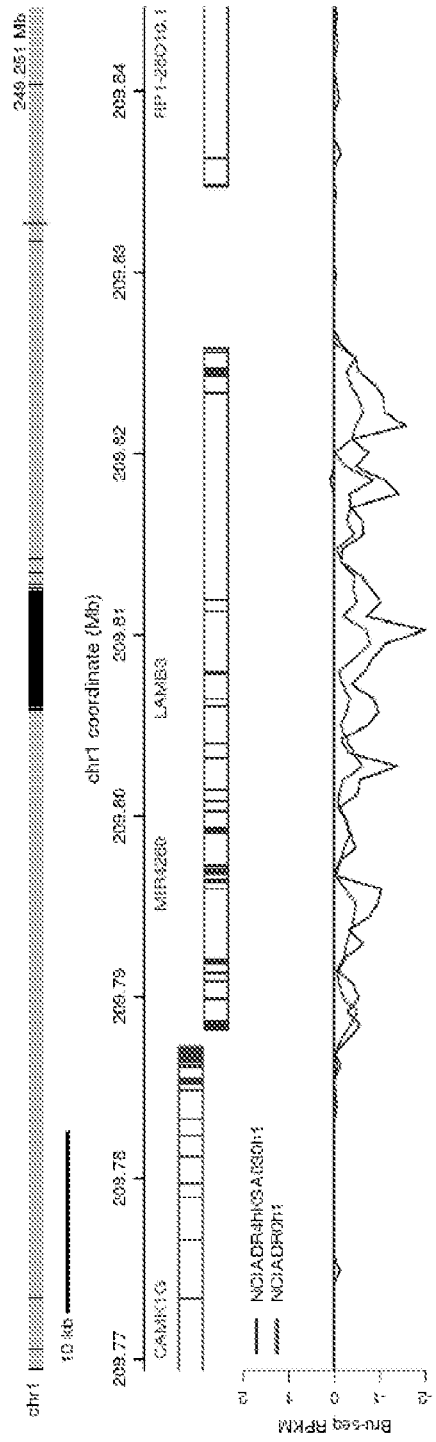
Figure 8E:
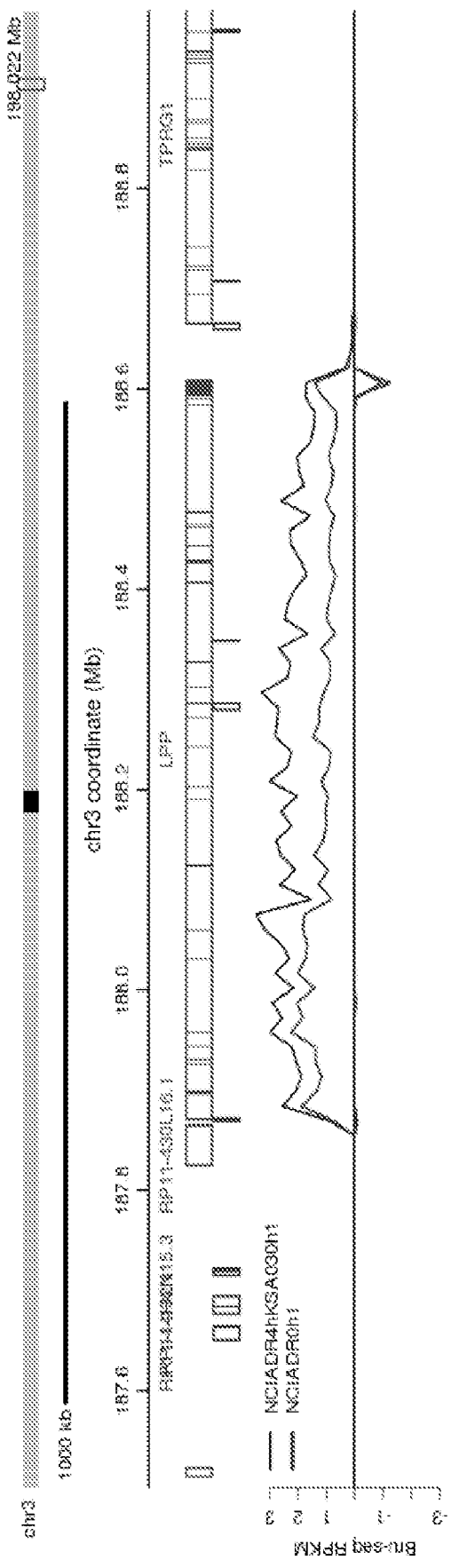

FIG. 8. Genes transcriptionally induced by KJA03 treatment (0.4 uM; 4 hours). (A) The synthesis of the LAMC2 gene is induced 3.217-fold following KJA03 treatment. (B) The synthesis of the CSRP1 gene is induced 3.335-fold following KJA03 treatment. (C) The synthesis of the SLC4A4 gene is induced 2.18-fold following KJA03 treatment. (D) The synthesis of the LAMB3 gene is induced 2.089-fold following KJA03 treatment. (E) The synthesis of the LPP gene is induced 2.032-fold following KJA03 treatment.

Figure 9A:
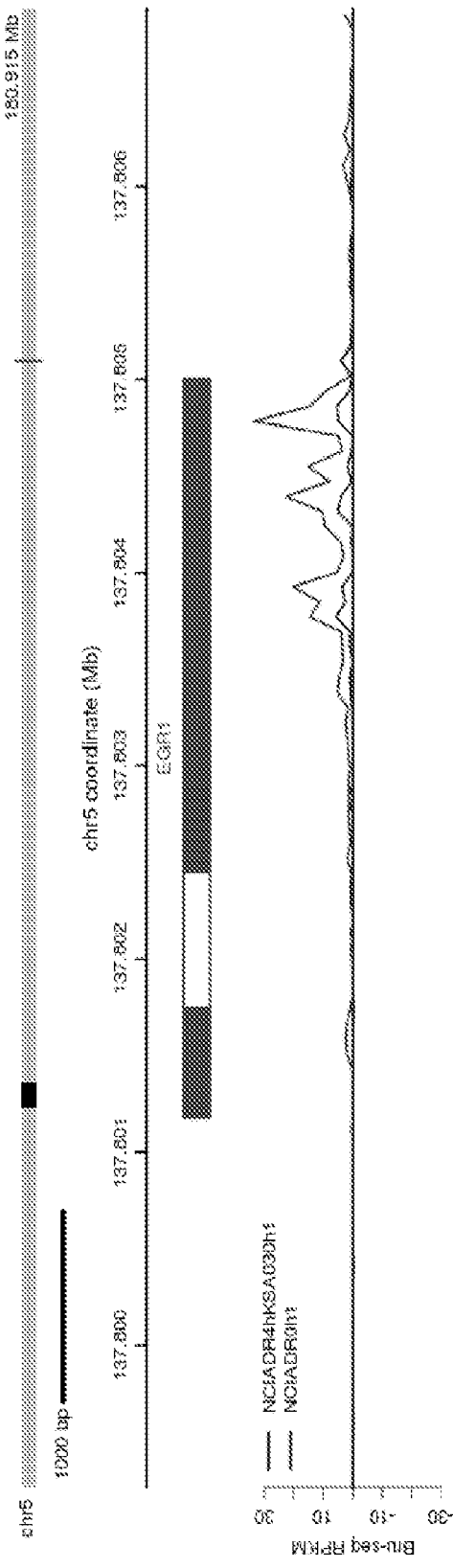
FIG. 9. Genes transcriptionally repressed by KJA03 treatment (0.4 uM; 4 hours). (A) The synthesis of the EGR1 gene is repressed 0.198-fold following KJA03 treatment. (B) The synthesis of the TXNIP gene is repressed 0.281-fold following KJA03 treatment. (C) The synthesis of the SFTA1P gene is repressed 0.387-fold following KJA03 treatment.
Figure 9B:
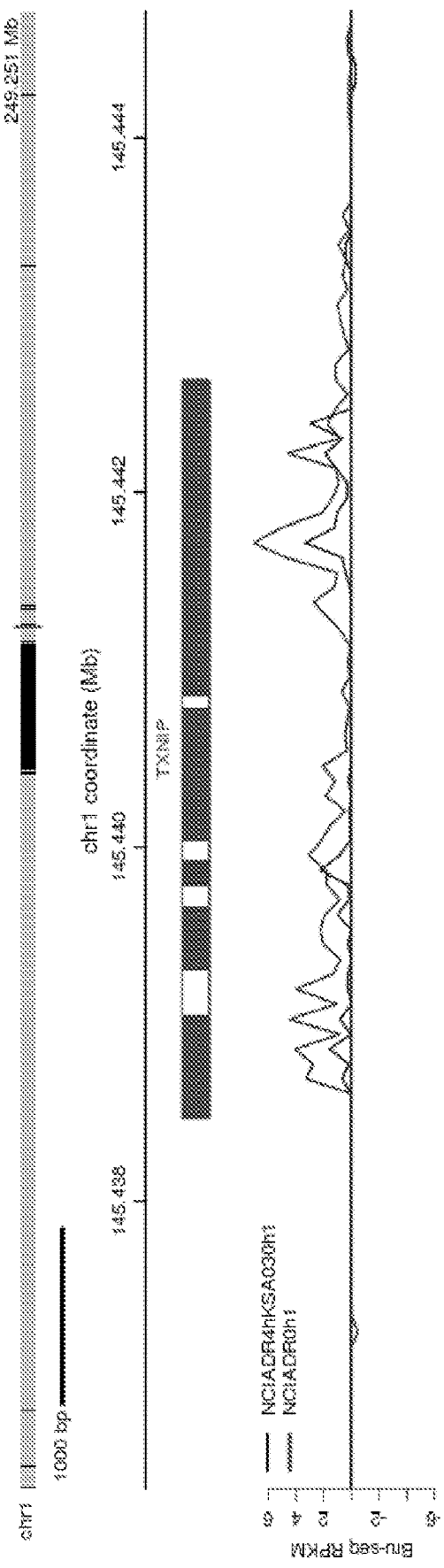
Figure 9C:
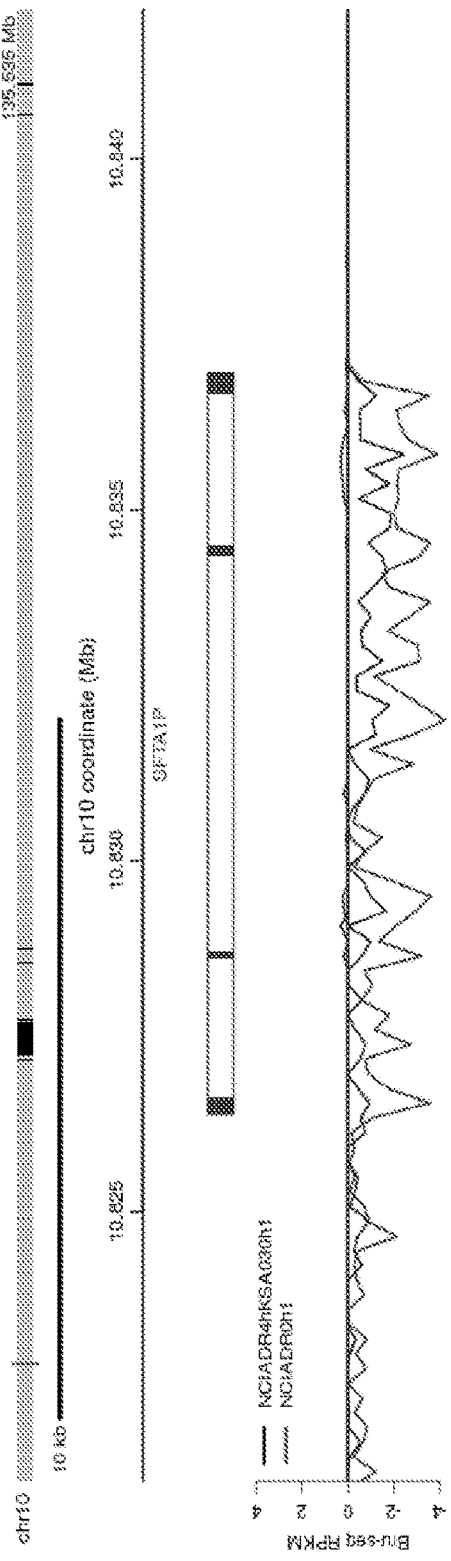
Figure 10A:
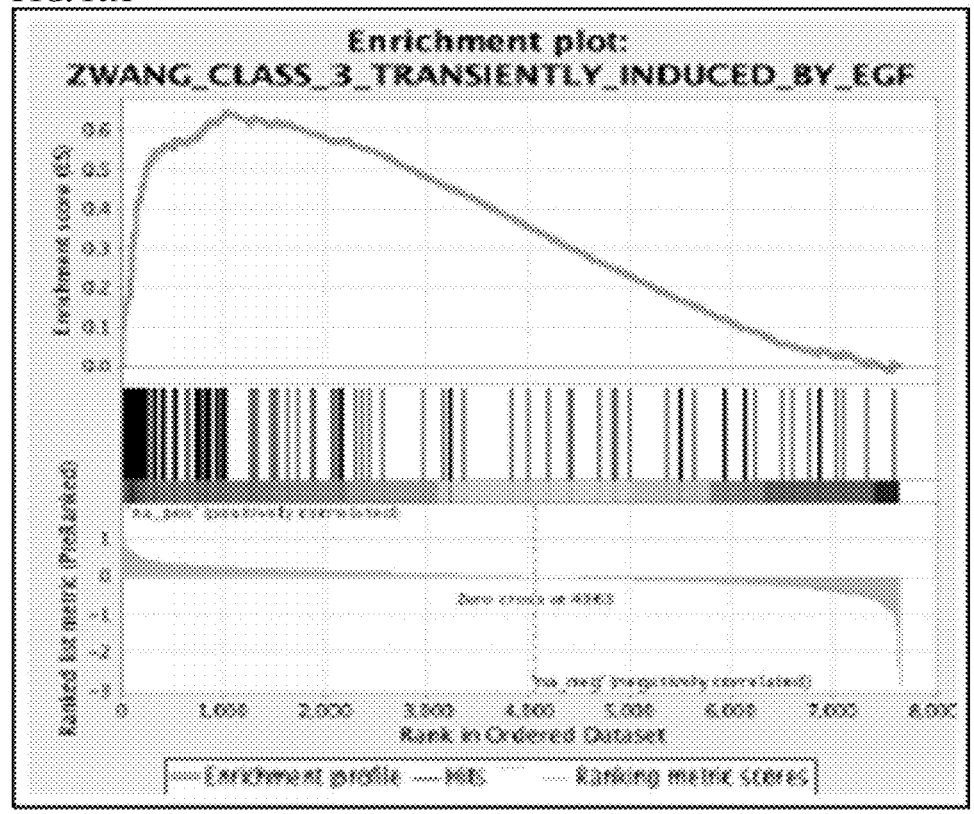
FIG. 10. GSEA plots of gene sets showing similarities with transcriptionally induced genes in NCI/ADR-RES cell line treated with KJA03 (0.4 uM; 4 hours). (A) ZWANG_CLASS_3_TRANSIENTLY_INDUCED_BY_EGF: Class III of genes transiently induced by EGF 184A1 cells (mammary epithelium). (B) ZHANG_RESPONSE_TO_IKK_INHIBITOR_AND_TNF_UP: Genes up-regulated in BxPC3 cells (pancreatic cancer) after treatment with TNF or IKI-1, an inhibitor of IkappaB kinase (IKK). (C) GSE2706_UNSTIM_VS_2H_LPS_AND_R848_DC_DN: Genes down-regulated in comparison of unstimulated dendritic cells (DC) at 0 h versus DCs stimulated with LPS (TLR4 agonist) and R848 for 2 h. (D) GSE26495_NAIVE_VS_PD1HIGH_CD8_TCELL_DN: Genes down-regulated in comparison of naive CD8 T cells versus PD-1 high CD8 T cells. (E) GSE2706_UNSTIM_VS_2H_LPS_DC_DN: Genes down-regulated in comparison of unstimulated dendritic cells (DC) at 0 h versus DCs stimulated with LPS (TLR4 agonist) for 2 h. (F) GSE2706_UNSTIM_VS_8H_LPS_DC_DN: Genes down-regulated in comparison of unstimulated dendritic cells (DC) at 0 h versus DCs stimulated with LPS (TLR4 agonist) for 8 h. (G) KIM_WT1_TARGETS_UP: Genes up-regulated in UB27 cells (osteosarcoma) at any time point after inducing the expression of a mutant form of WT1. (H) GSE26495_NAIVE_VS_PD1LOW_CD8_TCELL_DN: Genes down-regulated in comparison of naive CD8 T cells versus PD-1 low CD8 T cells. (I) ZHOU_INFLAMMATORY_RESPONSE_LIVE_UP: Genes up-regulated in macrophage by live P. gingivalis. (J) CHARAFE_BREAST_CANCER_LUMINAL_VS_MESENCHYMAL_DN: Genes down-regulated in luminal-like breast cancer cell lines compared to the mesenchymal-like ones. (K) GSE2706_UNSTIM_VS_8H_R848_DC_DN: Genes down-regulated in comparison of unstimulated dendritic cells (DC) at 0 h versus DCs stimulated with R848 for 8 h. (L) LIM_MAMMARY_STEM_CELL_UP: Genes consistently up-regulated in mammary stem cells both in mouse and human species. (M) GSE2706_UNSTIM_VS_2H_R848_DC_DN: Genes down-regulated in comparison of unstimulated dendritic cells (DC) at 0 h versus DCs stimulated with R848 for 2 h. (N) GSE360_L_DONOVANI_VS_B_MALAYI_LOW_DOSE_DC_UP: Genes up-regulated in comparison of dendritic cells (DC) exposed to L. donovani versus DCs exposed to 5 worm/well B. malayi. (O) RASHI_RESPONSE_TO_IONIZING_RADIATION_2: Cluster 2: late ATM dependent genes induced by ionizing radiation treatment. (P) PHONG_TNF_RESPONSE_VIA_P38_PARTIAL: Genes whose expression changes in Calu-6 cells (lung cancer) by TNF were blocked partially by p38 inhibitor LY479754.
Figure 10B:
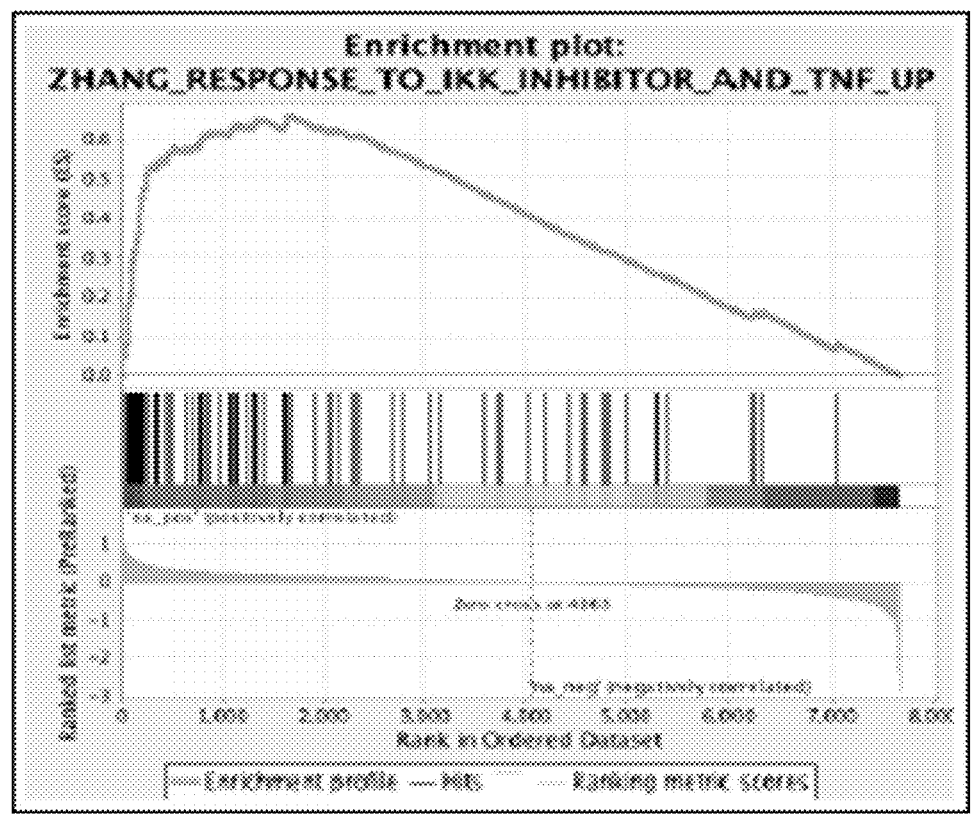
Figure 10C:
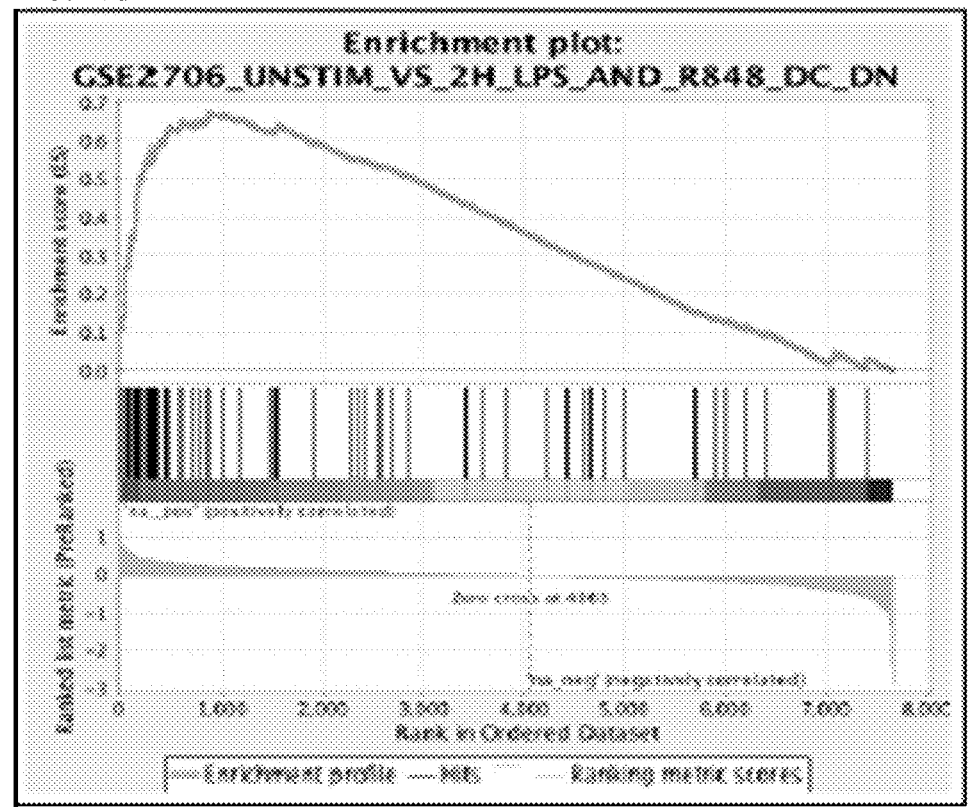
Figure 10D:
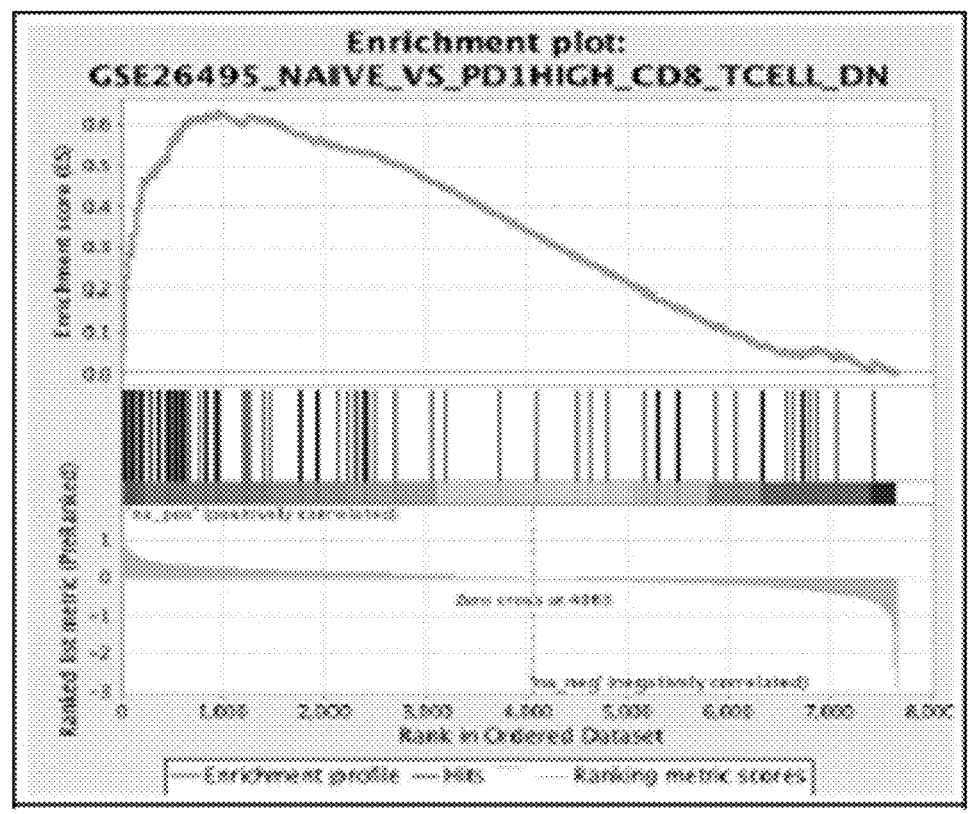
Figure 10E:
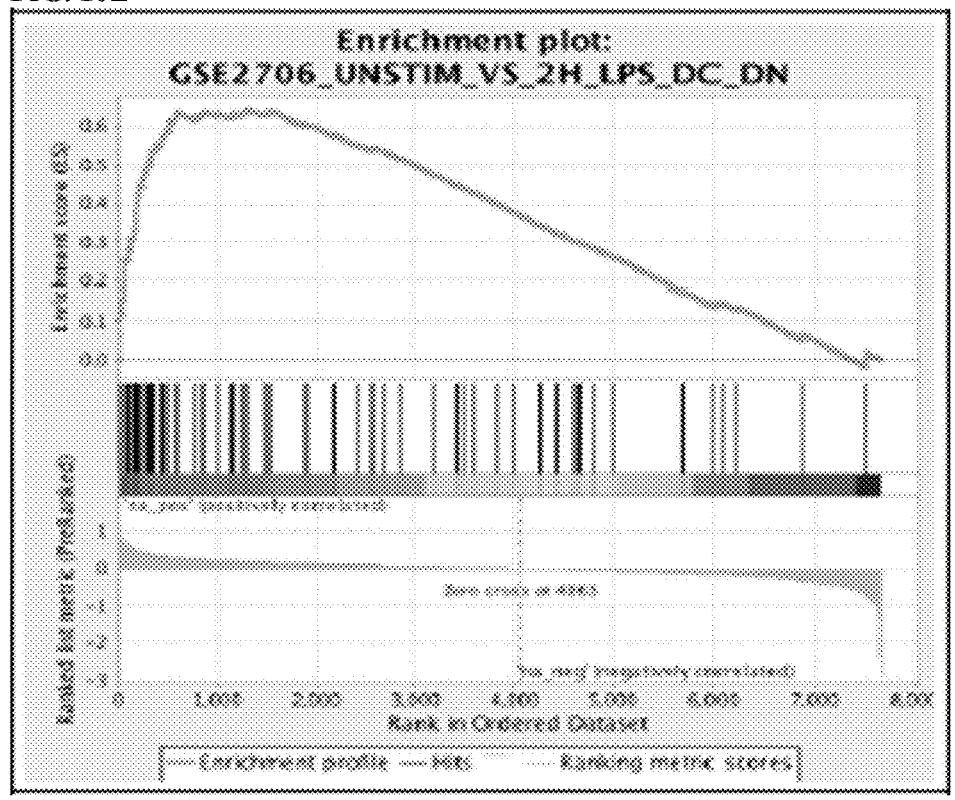
Figure 10F:
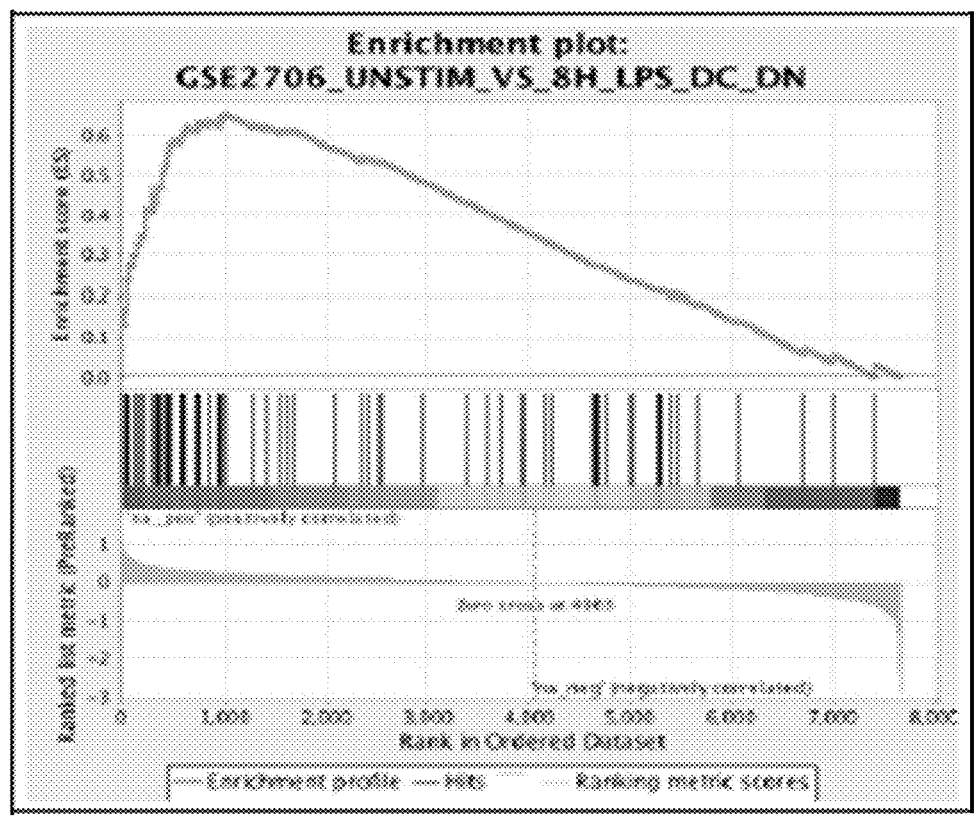
Figure 10G:
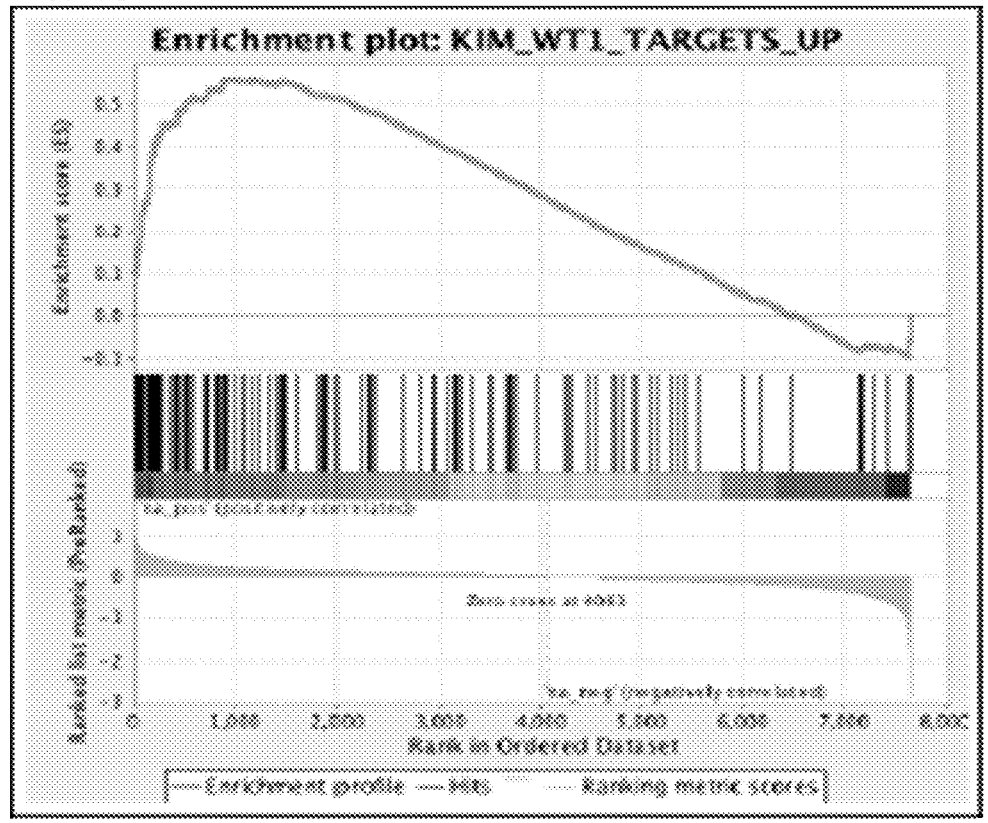
Figure 10H:
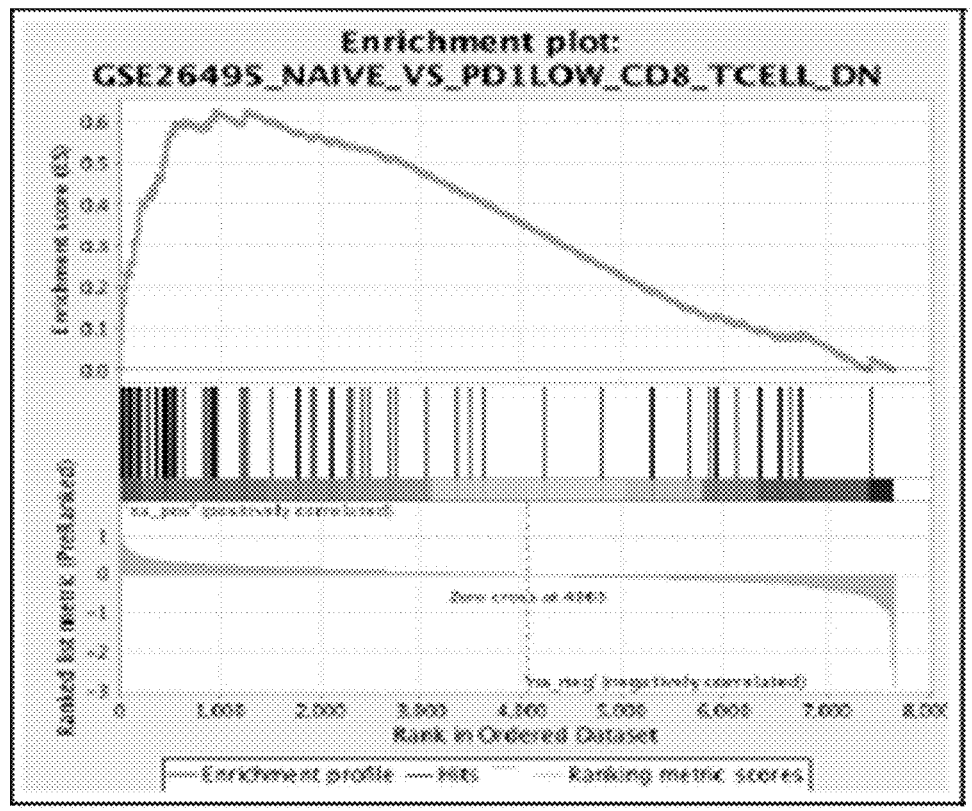
Figure 10I:
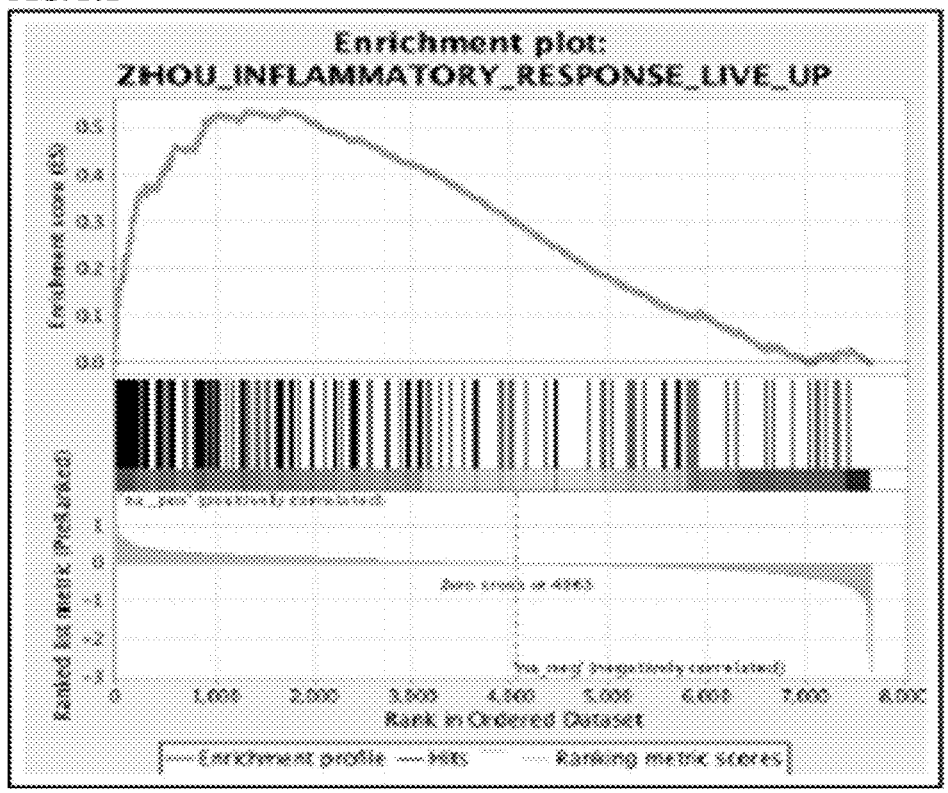
Figure 10J:
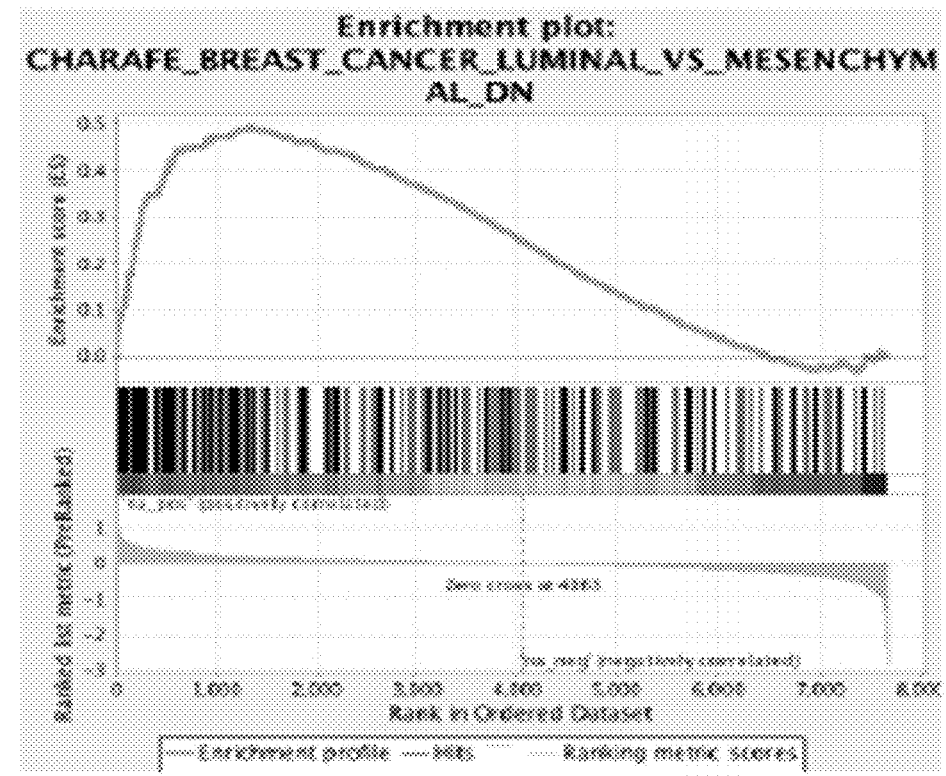
Figure 10K:
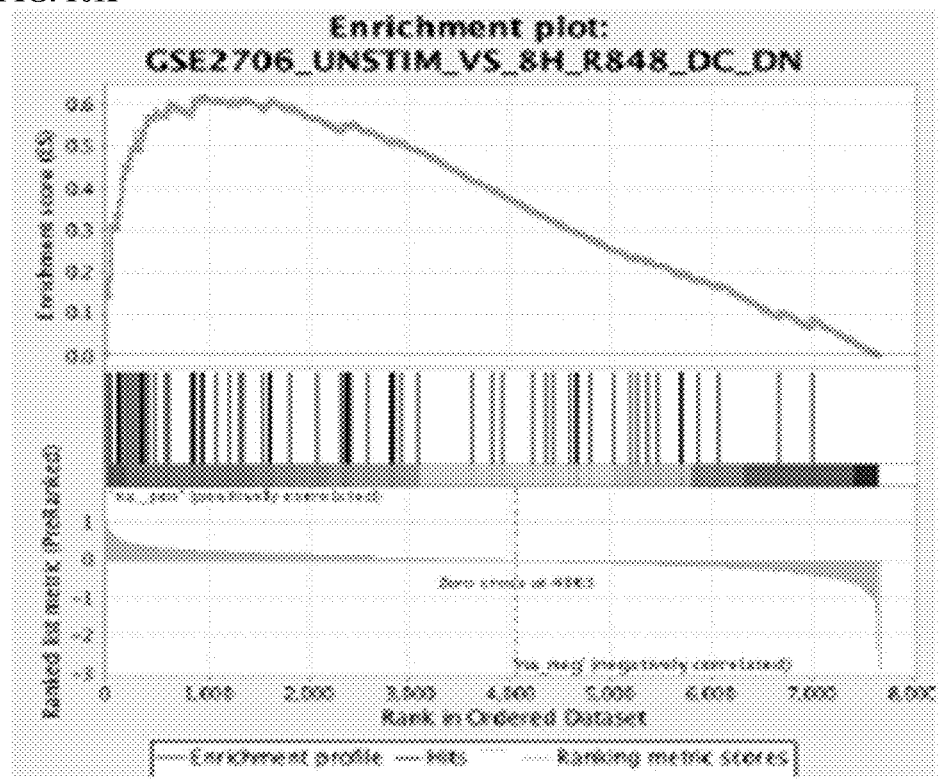
Figure 10L:
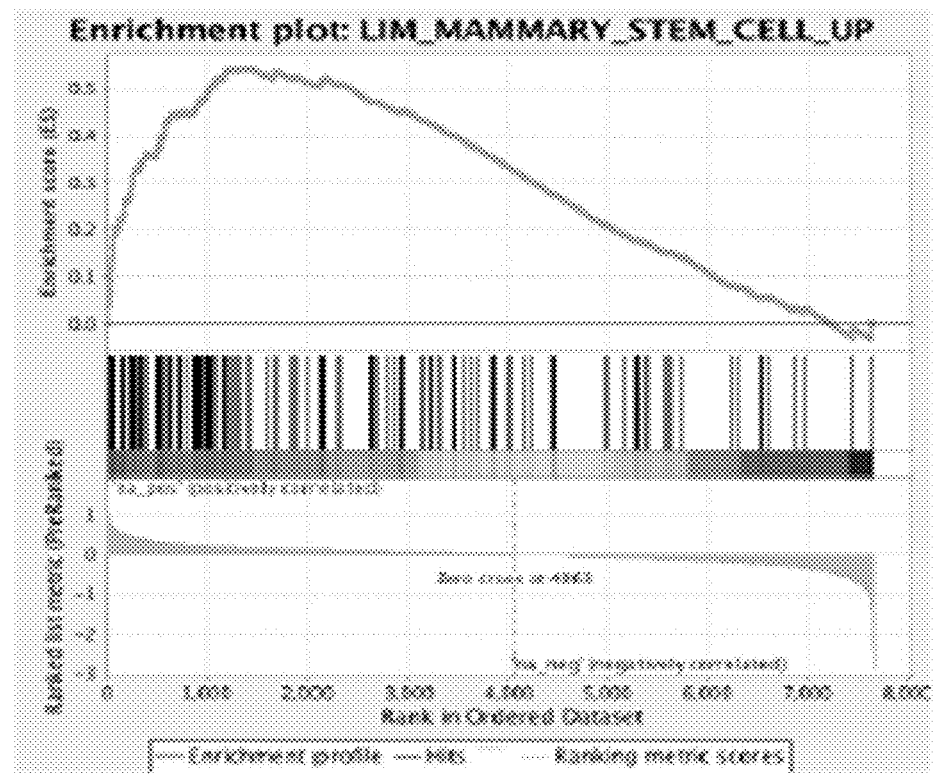
Figure 10M:
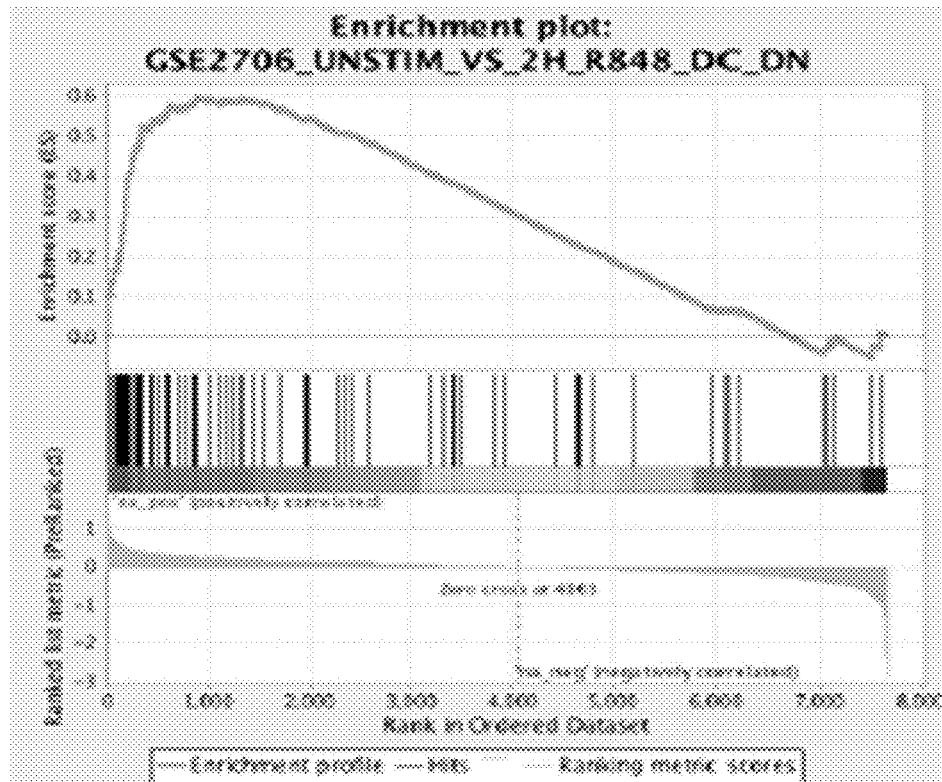
Figure 10N:
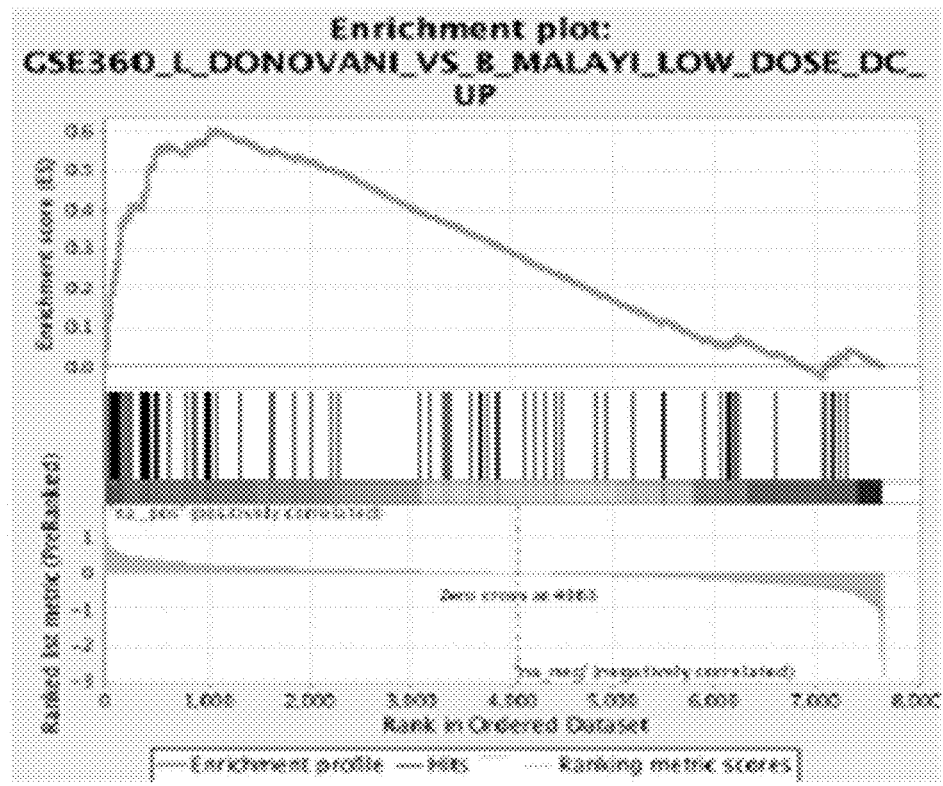
Figure 10O:
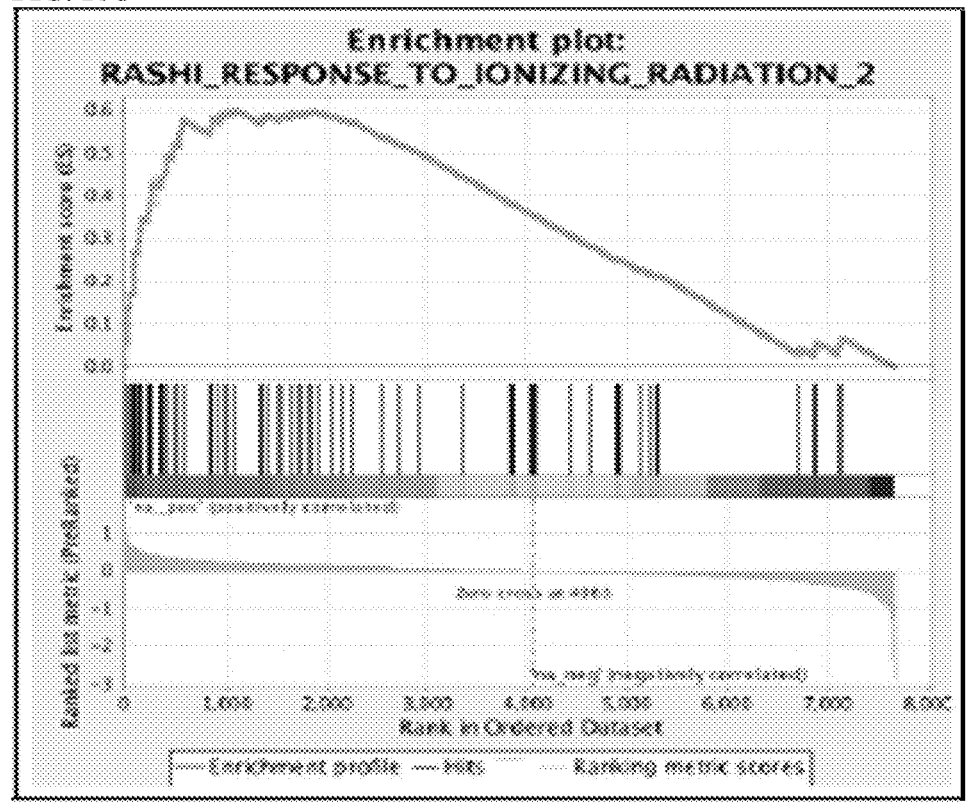
Figure 10P:
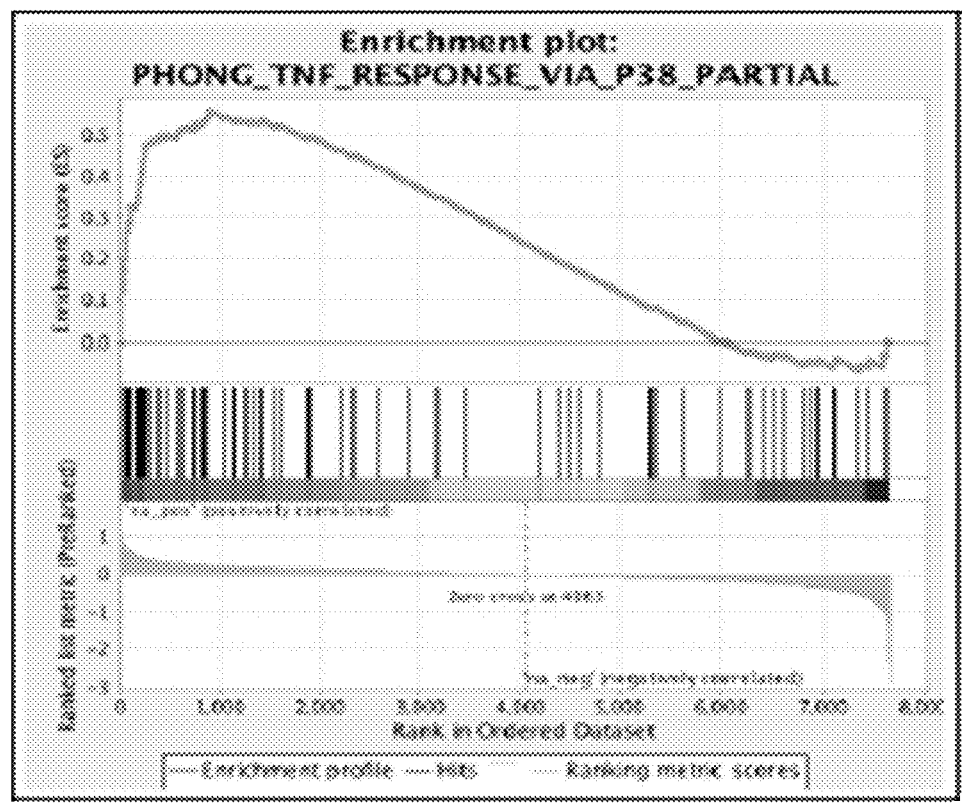
Figure 11A:
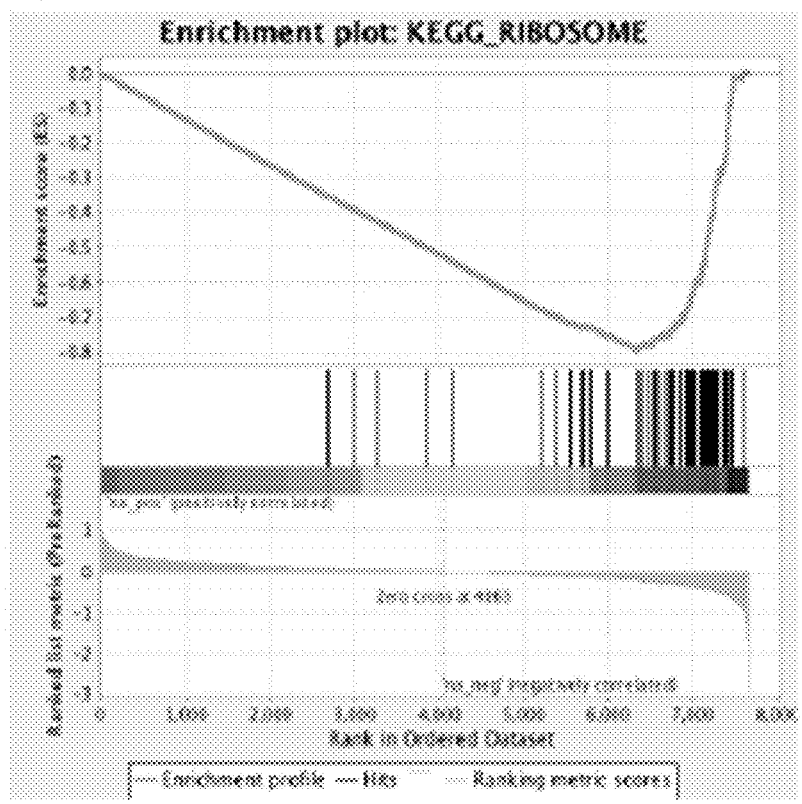
FIG. 11 GSEA plots of gene sets showing similarities with transcriptionally repressed genes in NCI/ADR-RES cell line treated with KJA03 (0.4 uM; 4 hours). (A) KEGG_RIBOSOME: Ribosome-related genes. (B) REACTOME_PEPTIDE_CHAIN_ELONGATION: Genes involved in Peptide chain elongation. (C) REACTOME_INFLUENZA_VIRAL_RNA_TRANSCRIPTION_AND_REPLICATION: Genes involved in Influenza Viral RNA Transcription and Replication. (D) STRUCTURAL_CONSTITUENT_OF_RIBOSOME: Genes annotated by the GO term GO:0003735. The action of a molecule that contributes to the structural integrity of the ribosome. (E) REACTOME_3_UTR_MEDIATED_TRANSLATIONAL_REGULATION: Genes involved in 3'-UTR-mediated translational regulation. (F) REACTOME_NONSENSE_MEDIATED_DECAY_ENHANCED_BY_THE_EXON_JUNCTION_COMPLEX: Genes involved in Nonsense Mediated Decay Enhanced by the Exon Junction Complex (G) REACTOME_SRP_DEPENDENT_COTRANSLATIONAL_PROTEIN_TARGETING_TO MEMBRANE: Genes involved in SRP-dependent cotranslational protein targeting to membrane. (H) GNF2_EIF3S6: Neighborhood of EIF3S6 eukaryotic translation initiation factor 3, subunit 6 48 kDa in the GNF2 expression compendium (I) REACTOME_TRANSLATION: Genes involved in Translation. (J) MARTENS_TRETINOIN_RESPONSE_DN: Genes down-regulated in NB4 cells (acute promyelocytic leukemia, APL) in response to tretinoin; based on Chip-seq data. (K) MORF_TPT1: Neighborhood of TPT1 tumor protein, translationally-controlled 1 in the MORF expression compendium. (L) REACTOME_INFLUENZA_LIFE_CYCLE: Genes involved in Influenza Life Cycle. (M) GCM_TPT1: Neighborhood of TPT1 tumor protein, translationally-controlled 1 in the GCM expression compendium (N) MODULE_114: Protein biosynthesis and ribosomes. (O) MODULE_151: Genes in the cancer module 151. (P) MORF_ACTG1: Neighborhood of ACTG1 actin, gamma 1 in the MORF expression compendium. (Q) GNF2_FBL: Neighborhood of FBL fibrillarin in the GNF2 expression compendium. (R) MORF_NME2: Neighborhood of NME2 non-metastatic cells 2, protein (NM23B) expressed in in the MORF expression compendium. (S) MODULE_83: Genes in the cancer module 83.
Figure 11B:
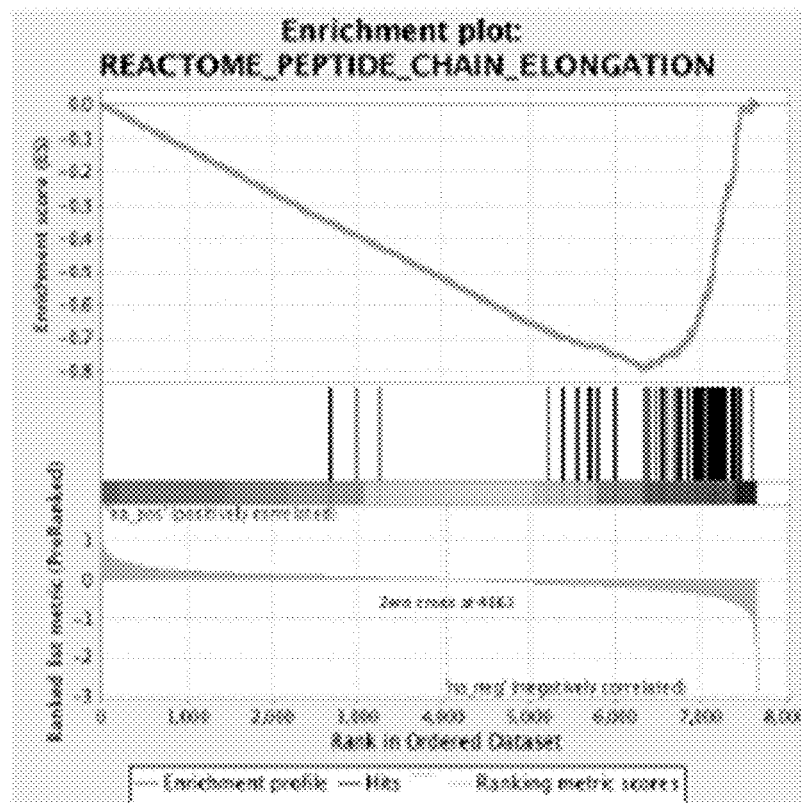
Figure 11C:
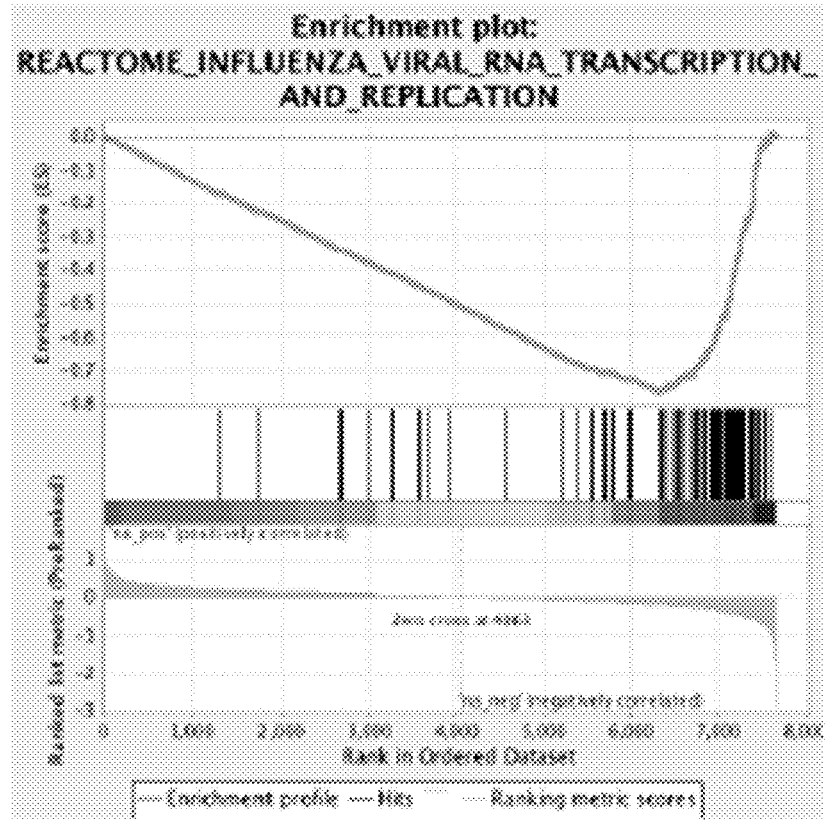
Figure 11D:
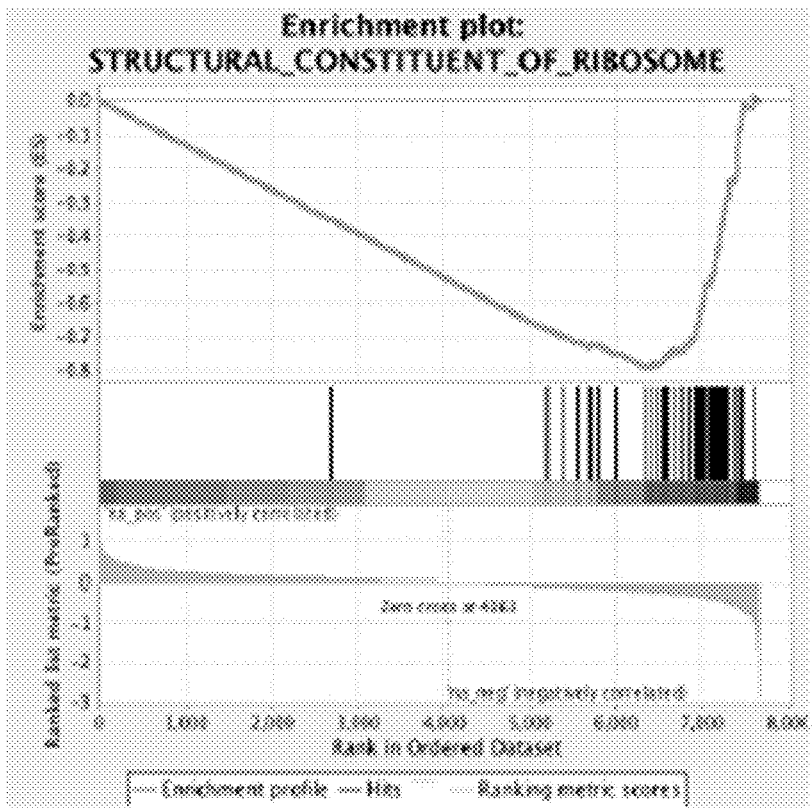
Figure 11E:
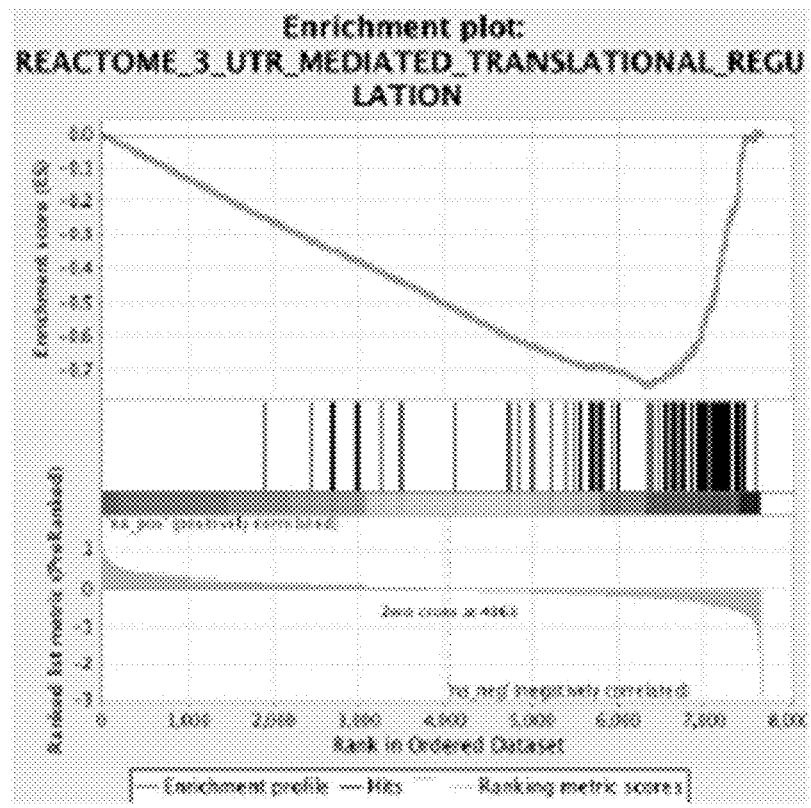
Figure 11F:
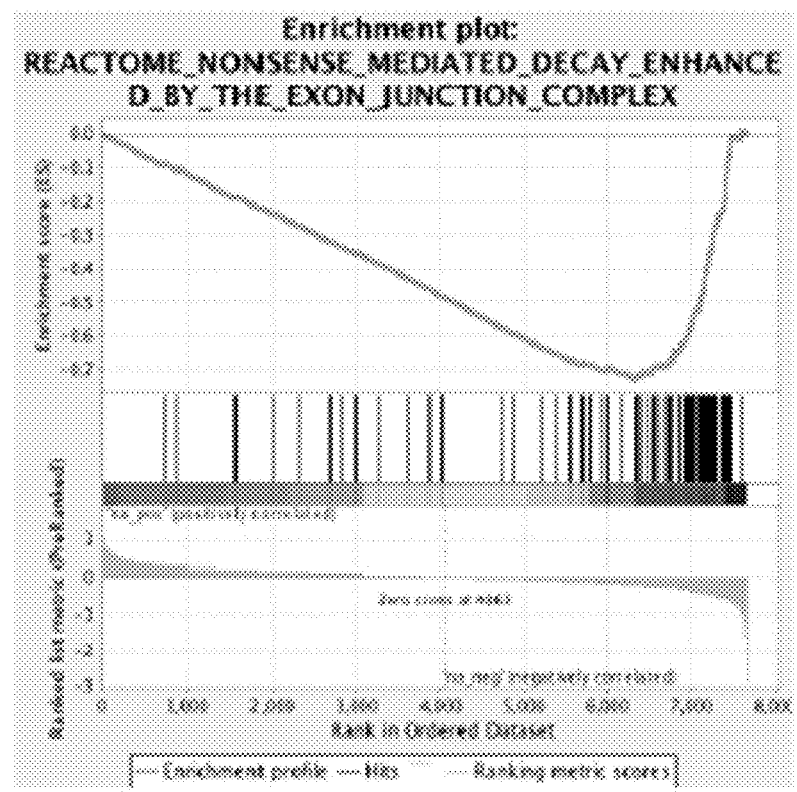
Figure 11G:
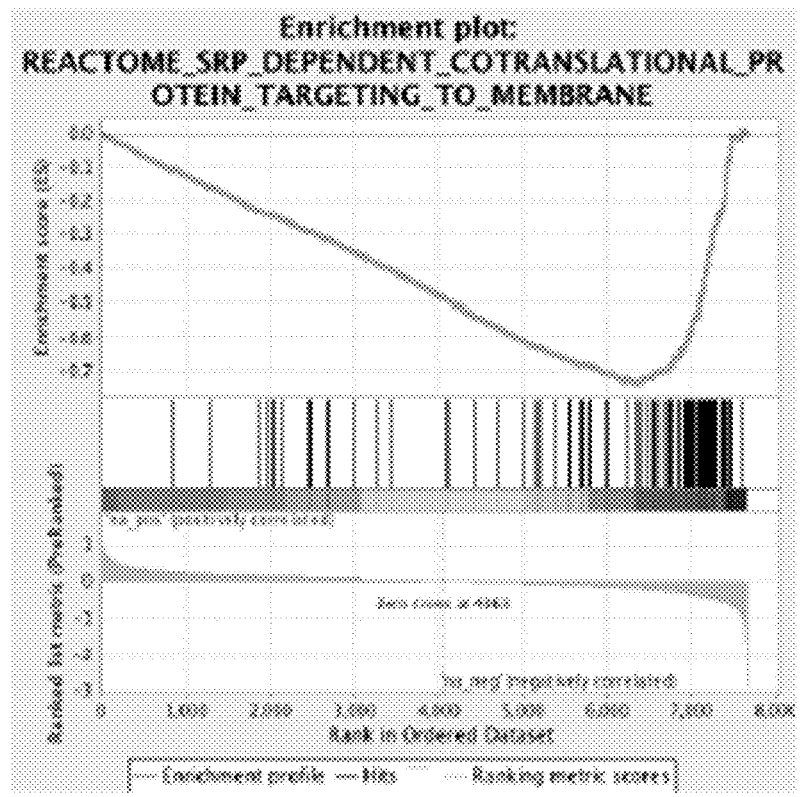
Figure 11H:
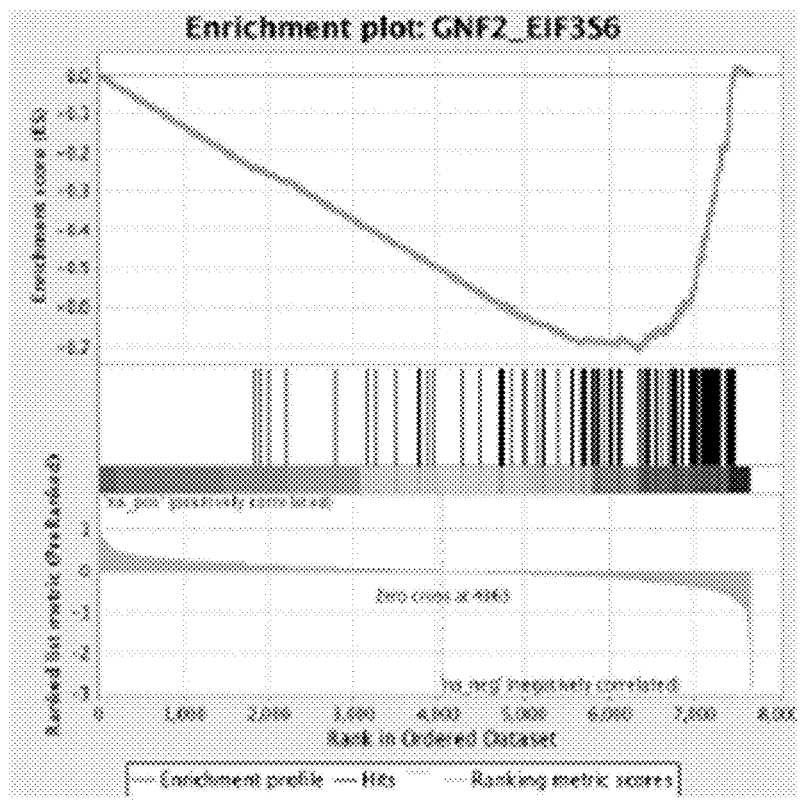
Figure 11I:
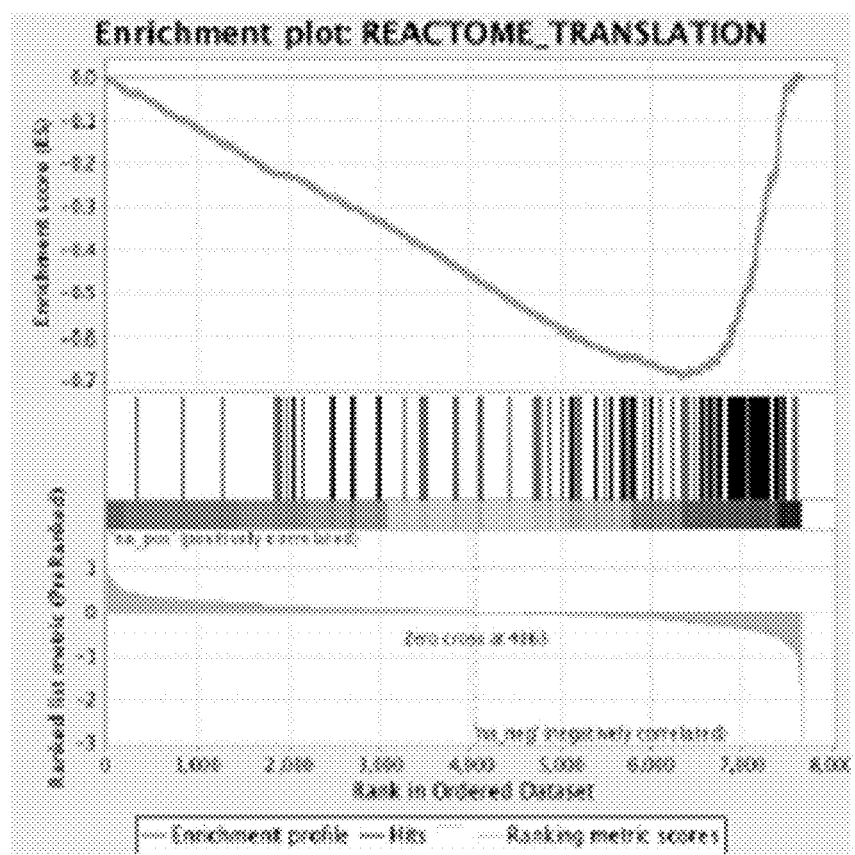
Figure 11J:
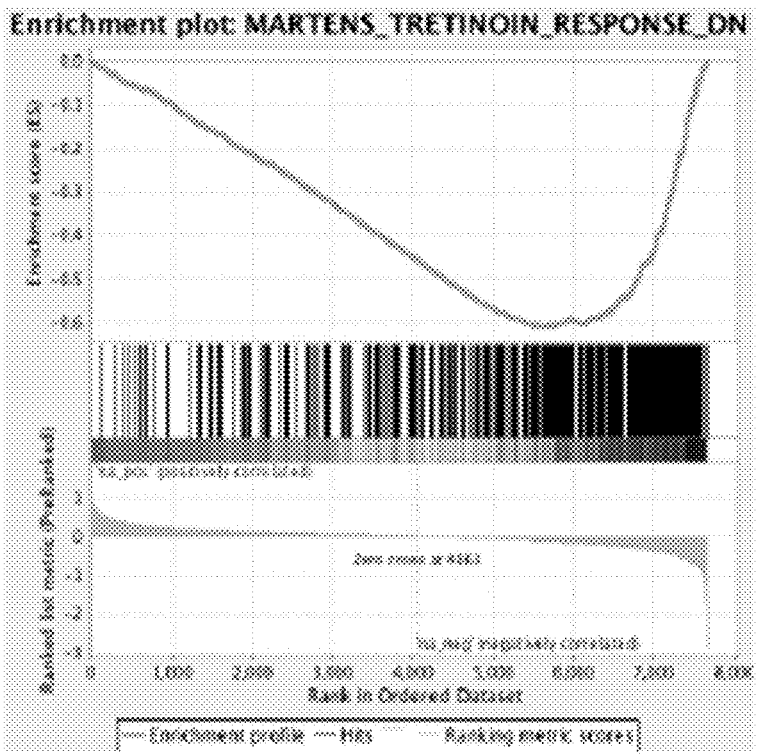
Figure 11K:
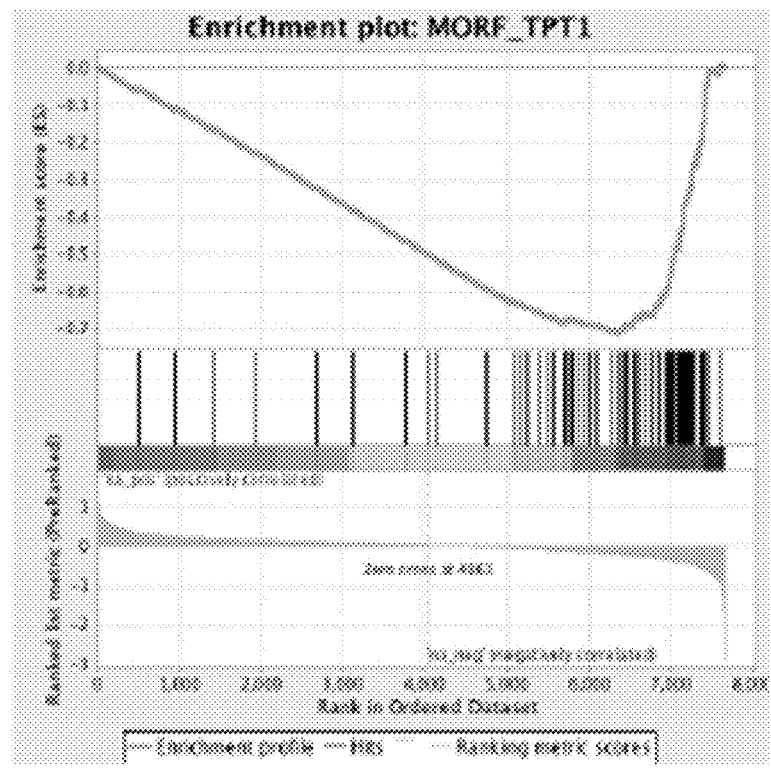
Figure 11L:
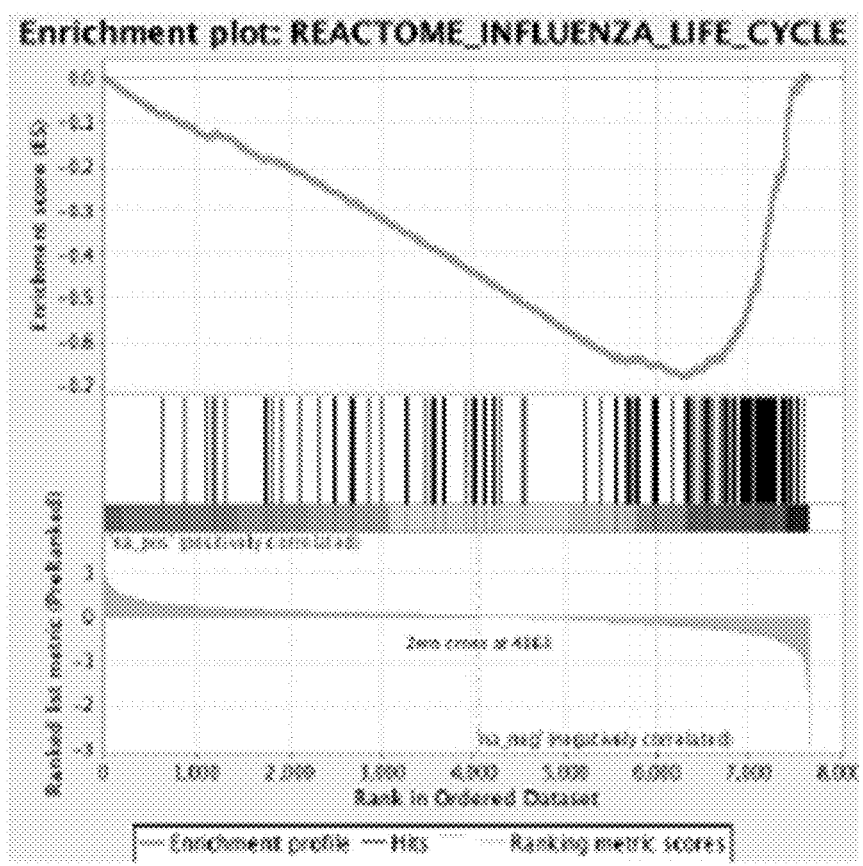
Figure 11M:
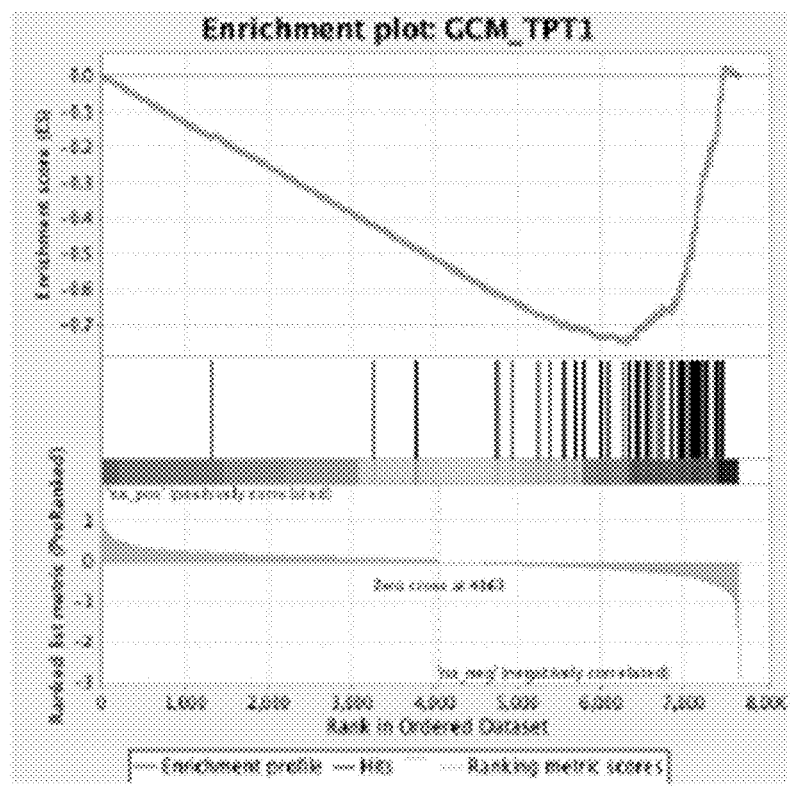
Figure 11N:
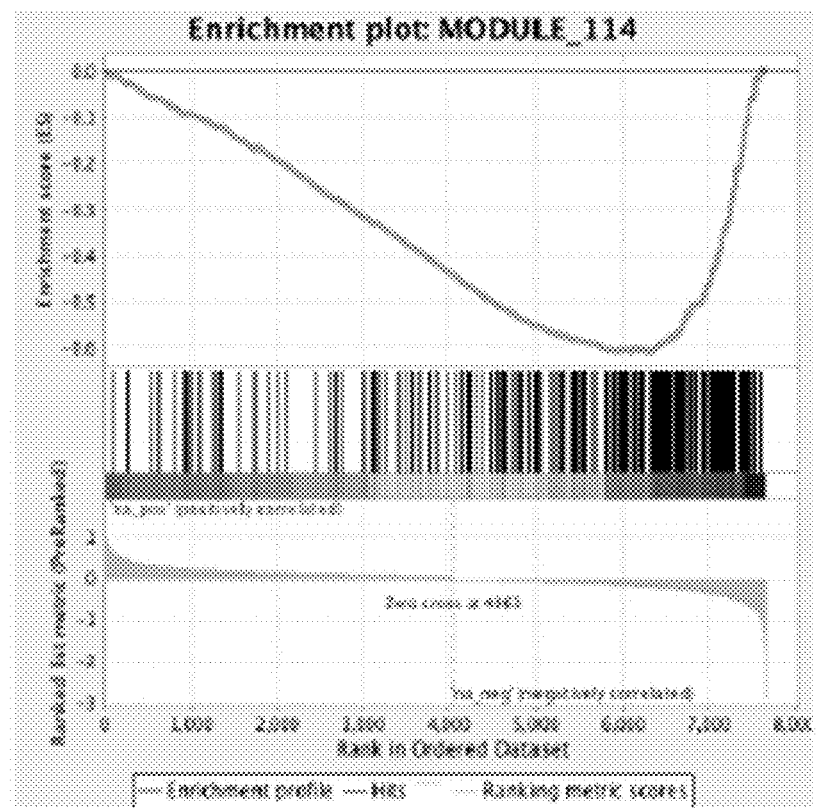
Figure 11O:
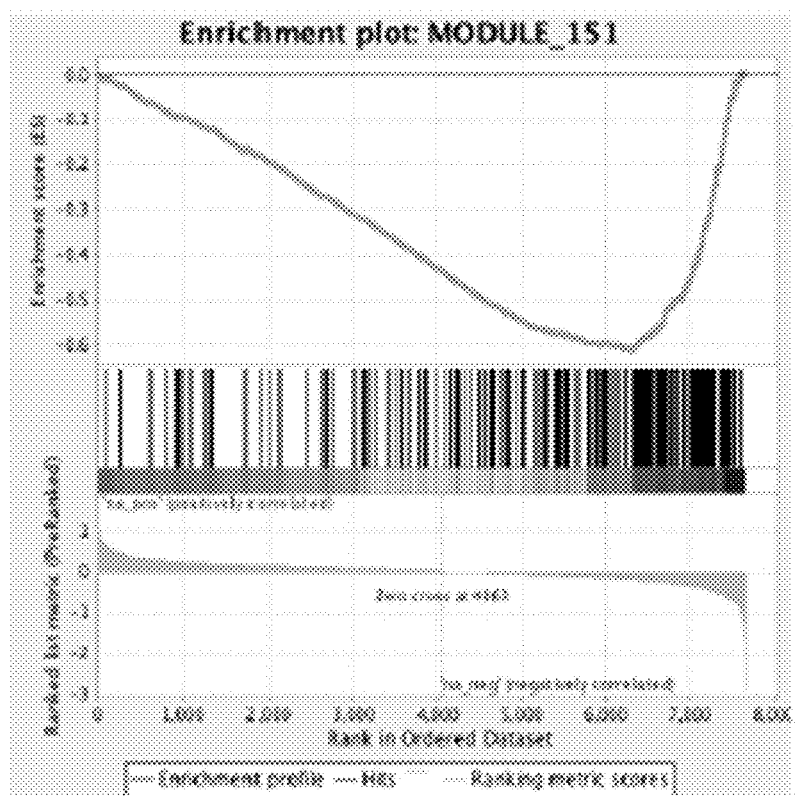
Figure 11P:
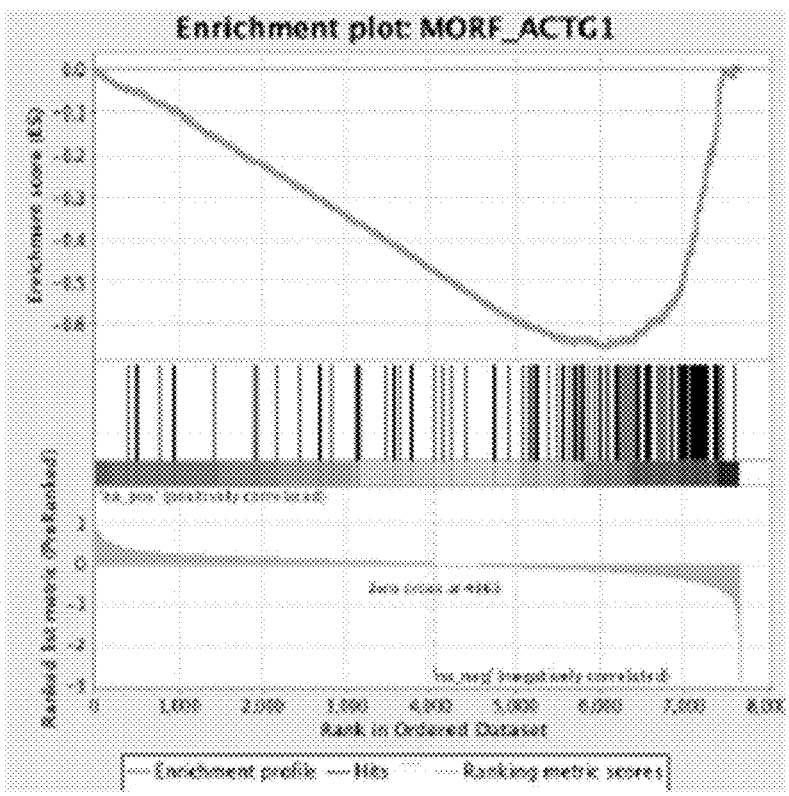
Figure 11Q:
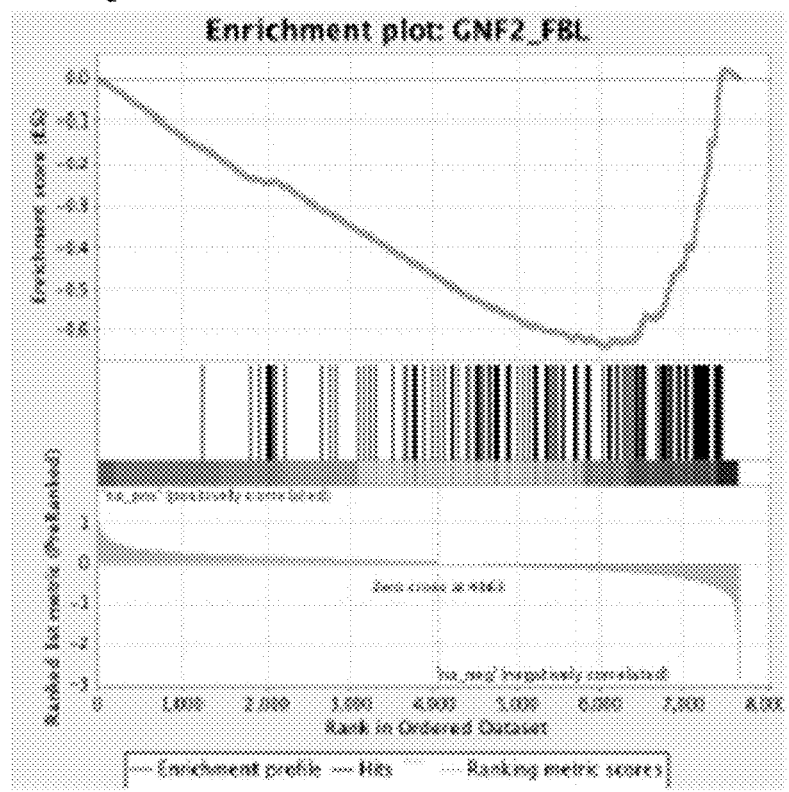
Figure 11R:
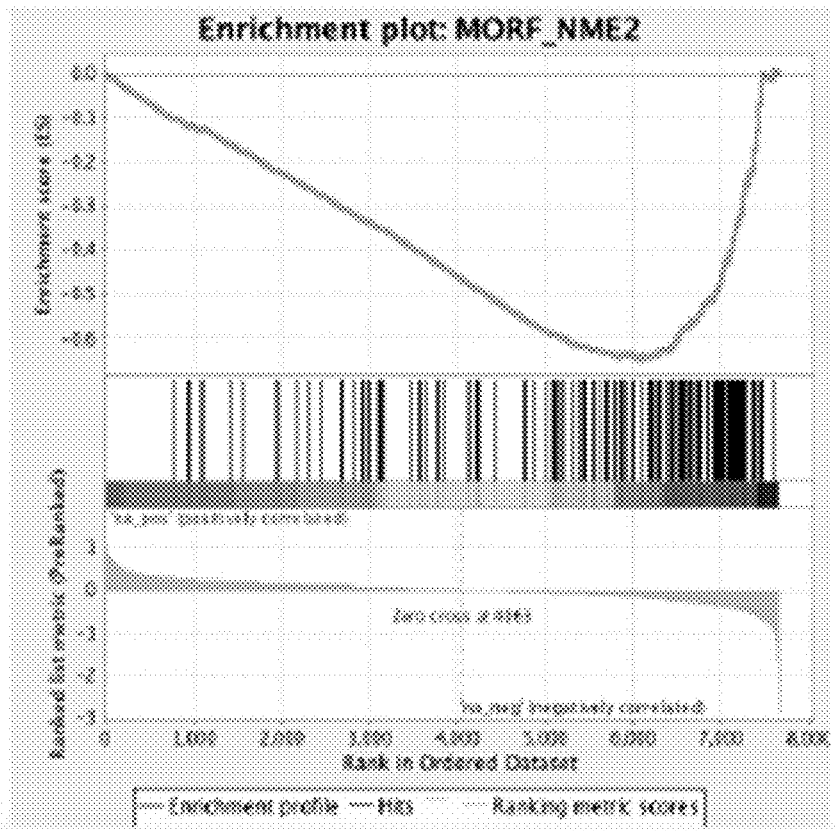
Figure 11S:
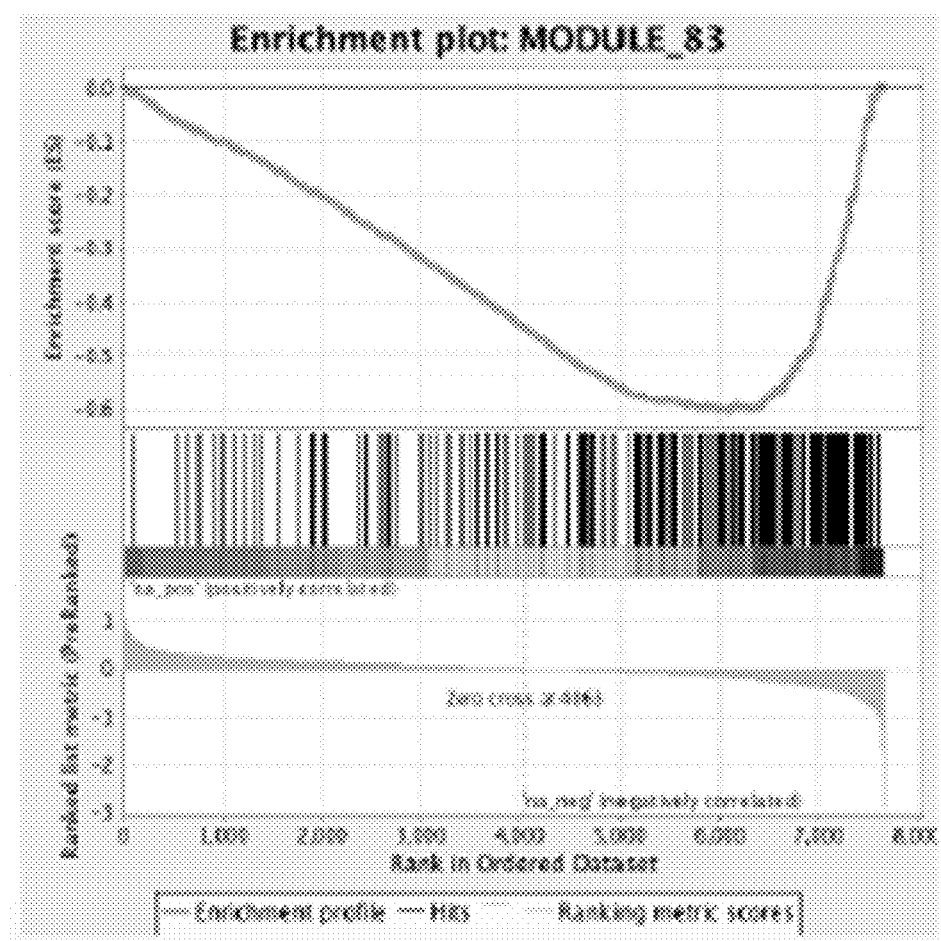

FIG. 9. Genes transcriptionally repressed by KJA03 treatment (0.4 uM; 4 hours). (A) The synthesis of the EGR1 gene is repressed 0.198-fold following KJA03 treatment. (B) The synthesis of the TXNIP gene is repressed 0.281-fold following KJA03 treatment. (C) The synthesis of the SFTA1P gene is repressed 0.387-fold following KJA03 treatment.

FIG. 10. GSEA plots of gene sets showing similarities with transcriptionally induced genes in NCI/ADR-RES cell line treated with KJA03 (0.4 uM; 4 hours). (A) ZWANG_CLASS_3_TRANSIENTLY_INDUCED_BY_EGF: Class III of genes transiently induced by EGF 184A1 cells (mammary epithelium). (B) ZHANG_RESPONSE_TO_IK-K_INHIBITOR_AND_TNF_UP: Genes up-regulated in BxPC3 cells (pancreatic cancer) after treatment with TNF or IM-1, an inhibitor of IkappaB kinase (IKK). (C) GSE2706_UNSTIM_VS_2H_LPS_AND_R848_DC_DN: Genes down-regulated in comparison of unstimulated dendritic cells (DC) at 0 h versus DCs stimulated with LPS (TLR4 agonist) and R848 for 2 h. (D) GSE26495_NAIVE_VS_PD1_HIGH_CD8_TCELL_DN: Genes down-regulated in comparison of naive CD8 T cells versus PD-1 high CD8 T cells. (E) GSE2706_UNSTIM_VS_2H_LPS_DC_DN: Genes down-regulated in comparison of unstimulated dendritic cells (DC) at 0 h versus DCs stimulated with LPS (TLR4 agonist) for 2 h. (F) GSE2706_UNSTIM_VS_8H_LPS_DC_DN: Genes down-regulated in comparison of unstimulated dendritic cells (DC) at 0 h versus DCs stimulated with LPS (TLR4 agonist) for 8 h. (G) MM_WT1_TARGETS_UP: Genes up-regulated in UB27 cells (osteosarcoma) at any time point after inducing the expression of a mutant form of WT1. (H) GSE26495_NAIVE_VS_PD1_LOW_CD8_TCELL_DN: Genes down-regulated in comparison of naive CD8 T cells versus PD-1 low CD8 T cells. (I) ZHOU_INFLAMMATORY_RESPONSE_LIVE_UP: Genes up-regulated in macrophage by live P. gingivalis. (J) CHARAFE_BREAST_CANCER_LUMINAL_VS_MESENCHYMAL_DN: Genes down-regulated in luminal-like breast cancer cell lines compared to the mesenchymal-like ones. (K) GSE2706_UNSTIM_VS_8H_R848_DC_DN: Genes down-regulated in comparison of unstimulated dendritic cells (DC) at 0 h versus DCs stimulated with R848 for 8 h. (L) LIM_MAMMARY_STEM_CELL_UP: Genes consistently up-regulated in mammary stem cells both in mouse and human species. (M) GSE2706_UNSTIM_VS_2H_R848_DC_DN: Genes down-regulated in comparison of unstimulated dendritic cells (DC) at 0 h versus DCs stimulated with R848 for 2 h. (N) GSE360_L_DONOVANI_VS_B_MALAYI_LOW_DOSE_DC_UP: Genes up-regulated in comparison of dendritic cells (DC) exposed to L. donovani versus DCs exposed to 5 worm/well B. malayi. (O) RASHI_RESPONSE_TO_IONIZING_RADIATION_2: Cluster 2: late ATM dependent genes induced by ionizing radiation treatment. (P) PHONG_TNF_RESPONSE_VIA_P38_PARTIAL: Genes whose expression changes in Calu-6 cells (lung cancer) by TNF were blocked partially by p38 inhibitor LY479754.

FIG. 11. GSEA plots of gene sets showing similarities with transcriptionally repressed genes in NCI/ADR-RES cell line treated with KJA03 (0.4 uM; 4 hours). (A) KEGG_RIBOSOME: Ribosome-related genes. (B) REACTOME_PEPTIDE_CHAIN_ELONGATION: Genes involved in Peptide chain elongation. (C) REACTOME_INFLUENZA_VIRAL_RNA_TRANSCRIPTION_AND_REPLICATION: Genes involved in Influenza Viral RNA Transcription and Replication. (D) STRUCTURAL_CONSTITUENT_OF_RIBOSOME: Genes annotated by the GO term GO:0003735. The action of a molecule that contributes to the structural integrity of the ribosome. (E) REACTOME_3_UTR_MEDIATED_TRANSLATIONAL_REGULATION: Genes involved in 3'-UTR-mediated translational regulation. (F) REACTOME_NONSENSE_MEDIATED_DECAY_ENHANCED_BY_THE_EXON_JUNCTION_COMPLEX: Genes involved in Nonsense Mediated Decay Enhanced by the Exon Junction Complex (G) REACTOME_SRP_DEPENDENT_COTRANSLATIONAL_PROTEIN_TARGETING_TO_MEMBRANE: Genes involved in SRP-dependent cotranslational protein targeting to membrane. (H) GNF2 EIF3S6: Neighborhood of EIF3S6 eukaryotic translation initiation factor 3, subunit 6 48 kDa in the GNF2 expression compendium (I) REACTOME_TRANSLATION: Genes involved in Translation. (J)

MARTENS_TRETINOIN_RESPONSE_DN: Genes downregulated in NB4 cells (acute promyelocytic leukemia, APL) in response to tretinoin; based on Chip-seq data. (K) MORF_TPT1: Neighborhood of TPT1 tumor protein, translationally-controlled 1 in the MORF expression compendium. (L) REACTOME_INFLUENZA_LIFE_CYCLE: Genes involved in Influenza Life Cycle. (M) GCM_TPT1: Neighborhood of TPT1 tumor protein, translationally-controlled 1 in the GCM expression compendium (N) MODULE_114: Protein biosynthesis and ribosomes. (O) MODULE_151: Genes in the cancer module 151. (P) MORF_ACTG1: Neighborhood of ACTG1 actin, gamma 1 in the MORF expression compendium. (Q) GNF2_FBL: Neighborhood of FBL fibrillarin in the GNF2 expression compendium. (R) MORF_NME2: Neighborhood of NME2 non-metastatic cells 2, protein (NM23B) expressed in in the MORF expression compendium. (S) MODULE_83: Genes in the cancer module 83.

Figure 12:
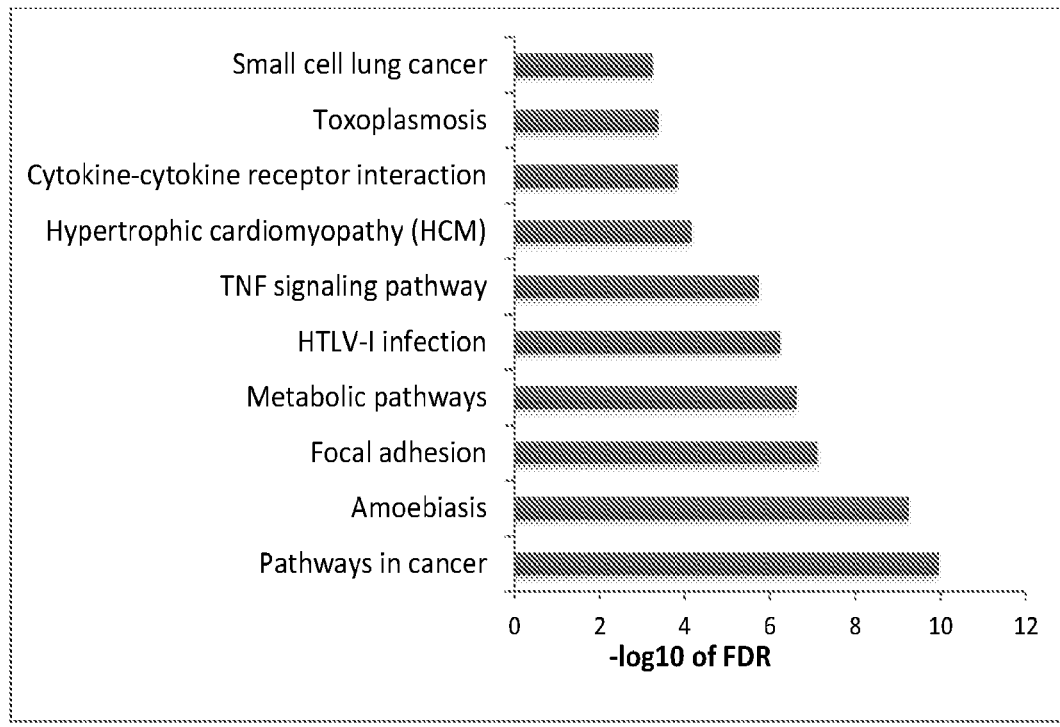
FIG. 12. DAVID output showing the 10 most upregulated KEGG pathways in NCI/ADR-RES cell line treated with 0.4 uM KJA03 for 4 hours.

FIG. 12. DAVID output showing the 10 most upregulated KEGG pathways in NCI/ADR-RES cell line treated with 0.4 uM KJA03 for 4 hours.

Figure 13:
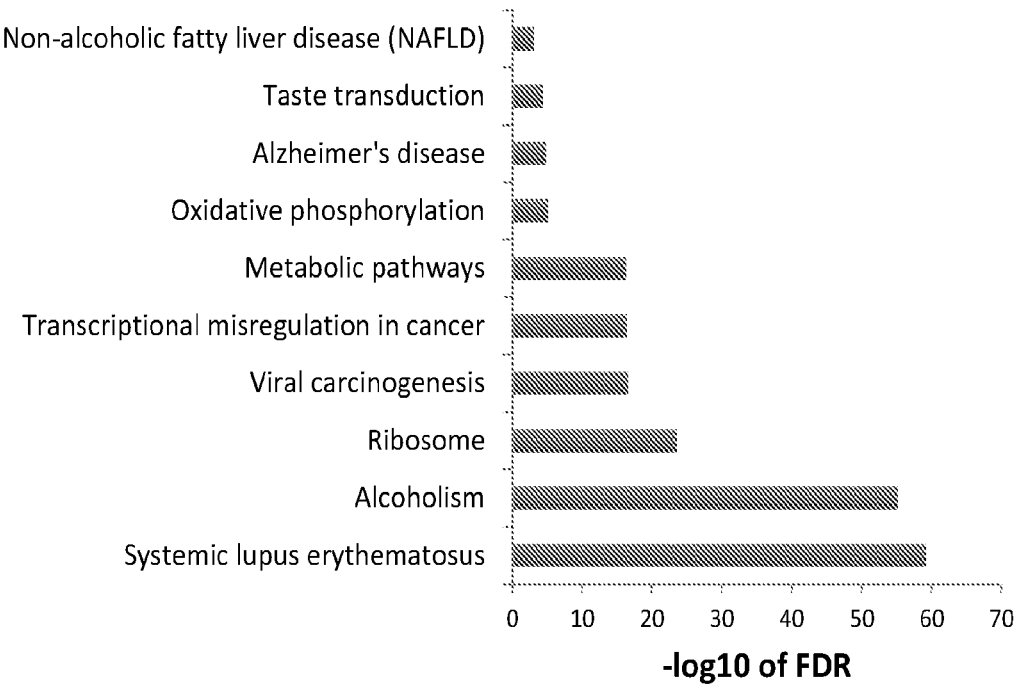
FIG. 13. DAVID output showing the 10 most downregulated KEGG pathways in NCI/ADR-RES cell line treated with 0.4 uM KJA03 for 4 hours.

FIG. 13. DAVID output showing the 10 most downregulated KEGG pathways in NCI/ADR-RES cell line treated with 0.4 uM KJA03 for 4 hours.

INCORPORATION BY REFERENCE

The entire disclosure of each of the patent documents and scientific articles referred to herein is incorporated by reference for all purposes.

The entire disclosure of each of the following scientific articles is incorporated by reference for all purposes:

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A compound having

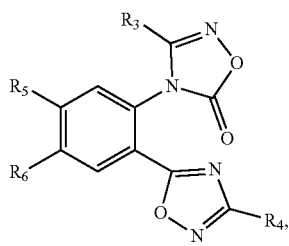

Formula VIII

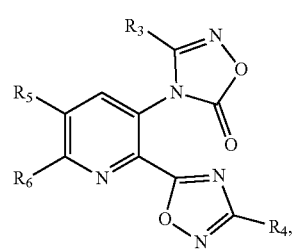

Formula IX

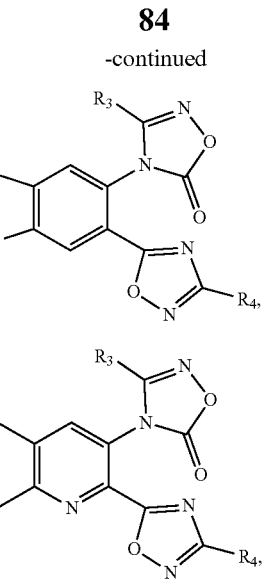

Formula X

Formula XI

Formula XII

Formula XIII including pharmaceutically acceptable salts, solvates, and/or prodrugs thereof;

wherein $R_3$ and $R_4$ are each independently a chemical moiety selected from hydrogen, methyl,

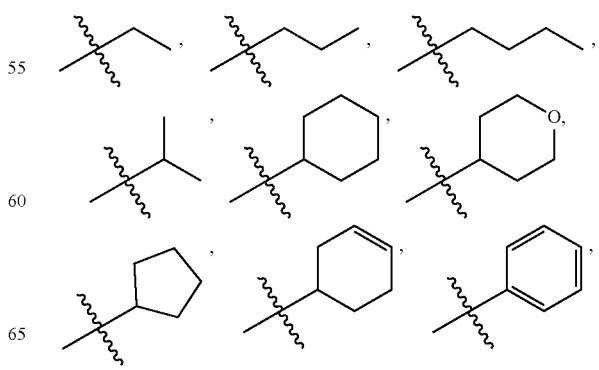

-continued

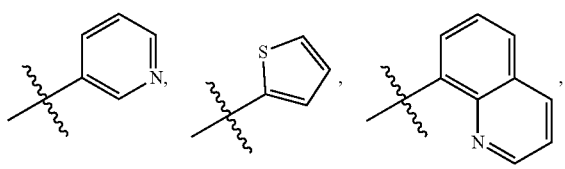

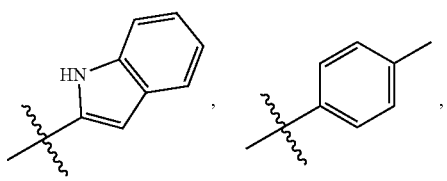

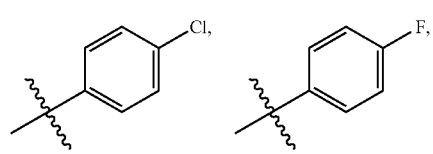

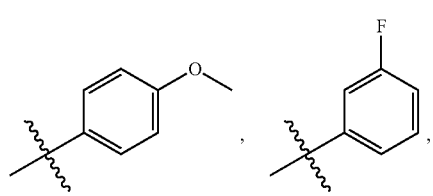

-continued

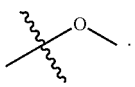

wherein $R_5$ and $R_6$ are each independently a chemical moiety selected from hydrogen, fluorine, chlorine, and

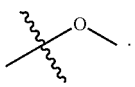 [SMILES: *OC ; "."]

and wherein if said compound has Formula VIII then:
$R_3$ and $R_4$ cannot both be phenyl, and $R_5$ and $R_6$ cannot both be hydrogen.

2. The compound of claim 1, wherein said compound is selected from the group consisting of:

| | | |
|---|---|---|
| KJA-21 | 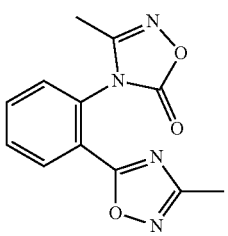 [SMILES: Cc1noc(-c2ccccc2-n2c(C)noc2=O)n1] | 3-methyl-4-(2-(3-(2-1,2,4-oxadiazol-5-yl)phenyl)-1,2,4-oxadiazol-5(4H)-one |
| KJA-22 | 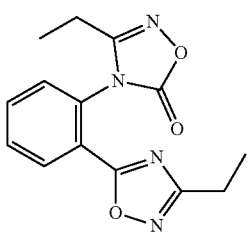 [SMILES: CCc1noc(-c2ccccc2-n2c(CC)noc2=O)n1] | 3-ethyl-4-(2-(3-ethyl-1,2,4-oxadiazol-5-yl)phenyl)-1,2,4-oxadiazol-5(4H)-one |
| KJA-23 | 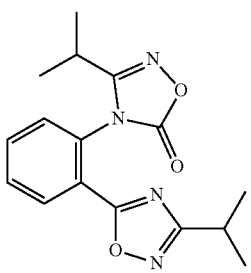 [SMILES: CC(C)c1noc(-c2ccccc2-n2c(C(C)C)noc2=O)n1] | 3-isopropyl-4-(2-(3-isopropyl-1,2,4-oxadiazol-5-yl)phenyl)-1,2,4-oxadiazol-5(4H)-one |

| | | |
|---|---|---|
| KJA-24 | 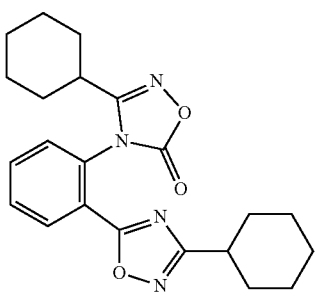 [SMILES: O=c1onc(C2CCCCC2)n1-c1ccccc1-c1nc(C2CCCCC2)no1] | 3-cyclohexyl-4-(2-(3-cyclohexyl-1,2,4-oxadiazol-5-yl)phenyl)-1,2,4-oxadiazol-5(4H)-one |
| KJA-25 | 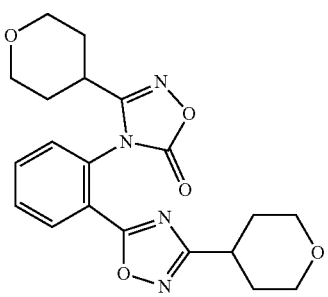 [SMILES: O=c1onc(C2CCOCC2)n1-c1ccccc1-c1nc(C2CCOCC2)no1] | 3-(tetrahydro-2H-pyran-4-yl)-4-(2-(3-(tetrahydro-2H-pyran-4-yl)-1,2,4-oxadiazol-5-yl)phenyl)-1,2,4-oxadiazol-5(4H)-one |
| KJA-26 | 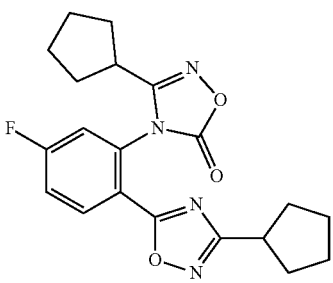 [SMILES: O=c1onc(C2CCCC2)n1-c1cc(F)ccc1-c1nc(C2CCCC2)no1] | 3-cyclopentyl-4-(2-(3-cyclopentyl-1,2,4-oxadiazol-5-yl)-5-fluorophenyl)-1,2,4-oxadiazol-5(4H)-one |
| KJA-27 | 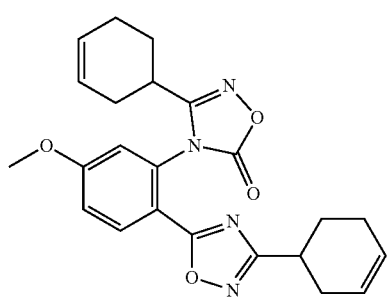 [SMILES: COc1ccc(-c2nc(C3CC=CCC3)no2)c(-n2c(C3CC=CCC3)noc2=O)c1] | 3-(cyclohex-3-en-1-yl)-4-(2-(3-(cyclohex-3-en-1-yl)-1,2,4-oxadiazol-5-yl)-5-methoxyphenyl)-1,2,4-oxadiazol-5(4H)-one |
| KJA-28 | 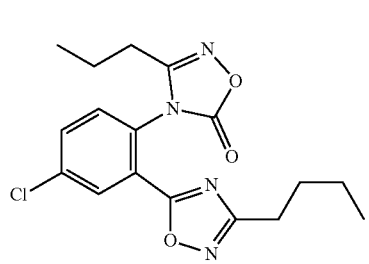 [SMILES: CCCCc1noc(-c2cc(Cl)ccc2-n2c(CCC)noc2=O)n1] | 4-(2-(5-butyl-1l3,2,4-chloraoxazol-3-yl)-4-chlorophenyl)-3-propyl-1,2,4-oxadiazol-5(4H)-one |

| | | |
|---|---|---|
| KJA-31 | 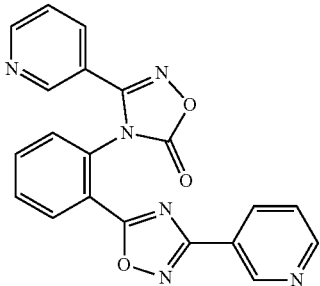 [SMILES: O=c1onc(-c2cccnc2)n1-c1ccccc1-c1nc(-c2cccnc2)no1] | 3-(pyridin-3-yl)-4-(2-(5-(pyridin-3-yl)-1l3,2,4-chloraoxazol-3-yl)phenyl)-1,2,4-oxadiazol-5(4H)-one |
| KJA-32 | 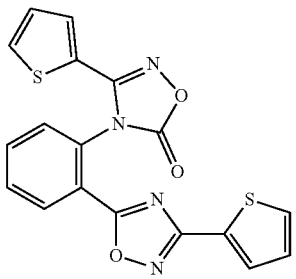 [SMILES: O=c1onc(-c2cccs2)n1-c1ccccc1-c1nc(-c2cccs2)no1] | 3-(thiophen-2-yl)-4-(2-(5-(thiophen-2-yl)-1l3,2,4-chloraoxazol-3-yl)phenyl)-1,2,4-oxadiazol-5(4H)-one |
| KJA-33 | 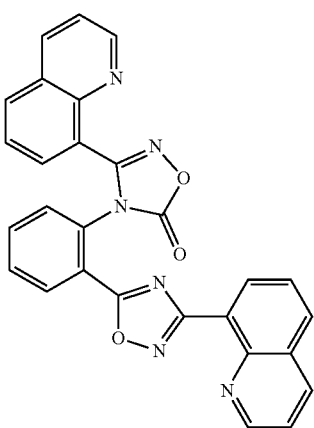 [SMILES: O=c1onc(-c2cccc3cccnc23)n1-c1ccccc1-c1nc(-c2cccc3cccnc23)no1] | 3-(quinolin-8-yl)-4-(2-(5-(quinolin-8-yl)-1l3,2,4-chloraoxazol-3-yl)phenyl)-1,2,4-oxadiazol-5(4H)-one |
| KJA-34 | 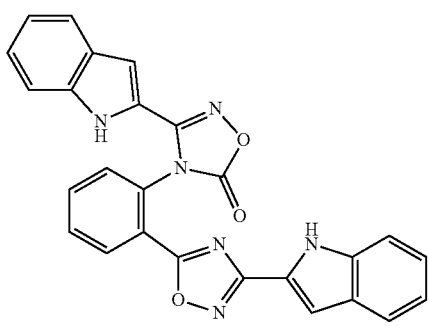 [SMILES: O=c1onc(-c2cc3ccccc3[nH]2)n1-c1ccccc1-c1nc(-c2cc3ccccc3[nH]2)no1] | 4-(2-(5-(1H-indol-2-yl)-1l3,2,4-chloraoxazol-3-yl)phenyl)-3-(1H-indol-2-yl)-1,2,4-oxadiazol-5(4H)-one |

| | | |
|---|---|---|
| KJA-02 | 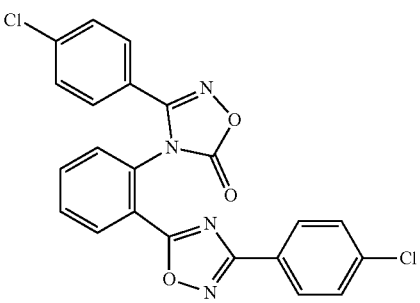 [SMILES: O=c1onc(-c2ccc(Cl)cc2)n1-c1ccccc1-c1nc(-c2ccc(Cl)cc2)no1] | 3-(4-chlorophenyl)-4-(2-(3-(4-chlorophenyl)-1,2,4-oxadiazol-5-yl)phenyl)-1,2,4-oxadiazol-5(4H)-one |
| KJA-03 | 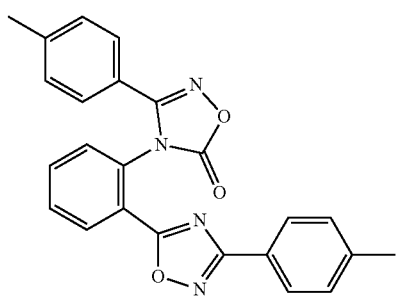 | 3-(p-tolyl)-4-(2-(3-(p-tolyl)-1,2,4-oxadiazol-5-yl)phenyl)-1,2,4-oxadiazol-5(4H)-one |
| KJA-04 | 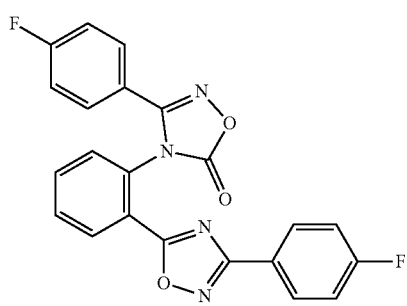 [SMILES: O=c1onc(-c2ccc(F)cc2)n1-c1ccccc1-c1nc(-c2ccc(F)cc2)no1] | 3-(4-fluorophenyl)-4-(2-(3-(4-fluorophenyl)-1,2,4-oxadiazol-5-yl)phenyl)-1,2,4-oxadiazol-5(4H)-one |
| KJA-05 | 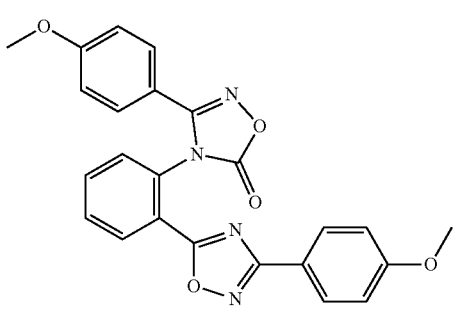 | 3-(4-methoxyphenyl)-4-(2-(3-(4-methoxyphenyl)-1,2,4-oxadiazol-5-yl)phenyl)-1,2,4-oxadiazol-5(4H)-one |
| KJA-07 | 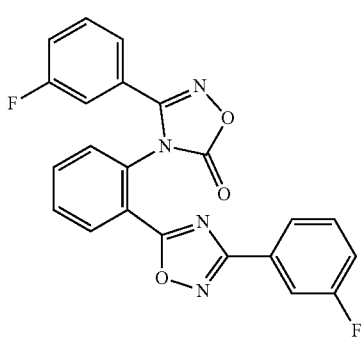 [SMILES: O=c1onc(-c2cccc(F)c2)n1-c1ccccc1-c1nc(-c2cccc(F)c2)no1] | 3-(3-fluorophenyl)-4-(2-(3-(3-fluorophenyl)-1,2,4-oxadiazol-5-yl)phenyl)-1,2,4-oxadiazol-5(4H)-one |

| | | |
|---|---|---|
| KJA-17 | 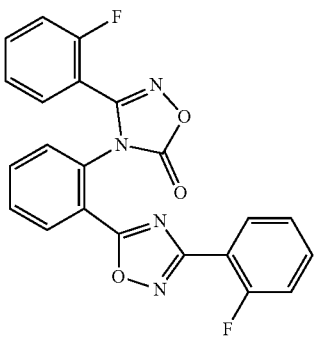 [SMILES: O=c1onc(-c2ccccc2F)n1-c1ccccc1-c1nc(-c2ccccc2F)no1] | 3-(2-fluorophenyl)-4-(2-(3-(2-fluorophenyl)-1,2,4-oxadiazol-5-yl)phenyl)-1,2,4-oxadiazol-5(4H)-one |
| KJA-06 | 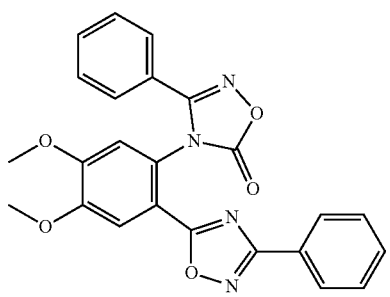 [SMILES: COc1cc(-c2nc(-c3ccccc3)no2)c(-n2c(-c3ccccc3)noc2=O)cc1OC] | 4-(4,5-dimethoxy-2-(3-phenyl-1,2,4-oxadiazol-5-yl)phenyl)-3-phenyl-1,2,4-oxadiazol-5(4H)-one |
| KJA-09 | 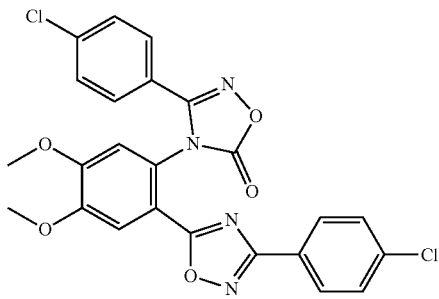 [SMILES: COc1cc(-c2nc(-c3ccc(Cl)cc3)no2)c(-n2c(-c3ccc(Cl)cc3)noc2=O)cc1OC] | 3-(4-chlorophenyl)-4-(2-(3-(4-chlorophenyl)-1,2,4-oxadiazol-5-yl)-4,5-dimethoxyphenyl)-1,2,4-oxadiazol-5(4H)-one |
| KJA-08 | 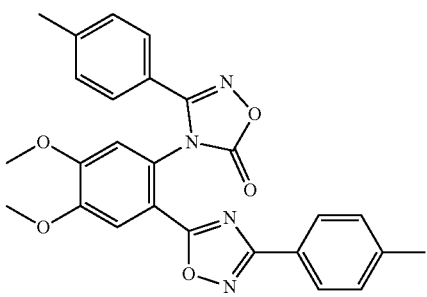 | 4-(4,5-dimethoxy-2-(3-(p-tolyl)-1,2,4-oxadiazol-5-yl)phenyl)-3-(p-tolyl)-1,2,4-oxadiazol-5(4H)-one |
| KJA-10 | 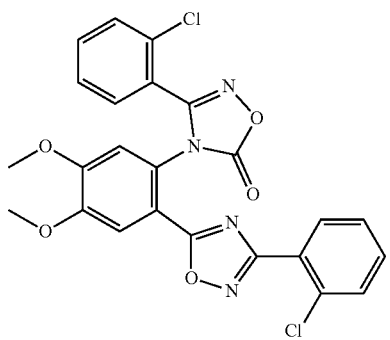 [SMILES: COc1cc(-c2nc(-c3ccccc3Cl)no2)c(-n2c(-c3ccccc3Cl)noc2=O)cc1OC] | 3-(2-chlorophenyl)-4-(2-(3-(2-chlorophenyl)-1,2,4-oxadiazol-5-yl)-4,5-dimethoxyphenyl)-1,2,4-oxadiazol-5(4H)-one |

| | | |
|---|---|---|
| KJA-16 | 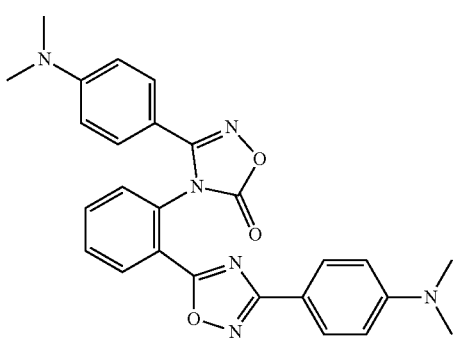 | 3-(4-(dimethylamino)phenyl)-4-(2-(3-(4-(dimethylamino)phenyl)-1,2,4-oxadiazol-5-yl)phenyl)-1,2,4-oxadiazol-5(4H)-one |
| KJA-43 | 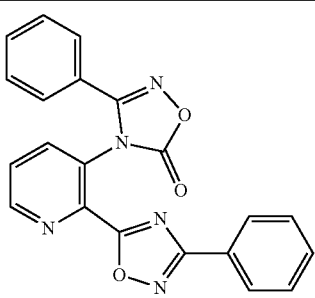 | 3-phenyl-4-(2-(3-phenyl-1,2,4-oxadiazol-5-yl)pyridin-3-yl)-1,2,4-oxadiazol-5(4H)-one |
| KJA-44 | 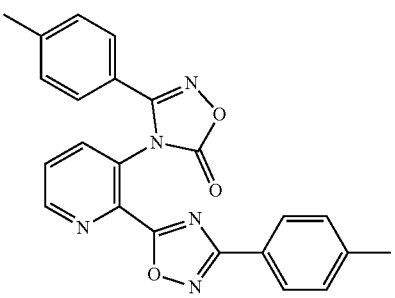 | 3-(p-tolyl)-4-(2-(3-(p-tolyl)-1,2,4-oxadiazol-5-yl)pyridin-3-yl)-1,2,4-oxadiazol-5(4H)-one |
| KJA-45 | 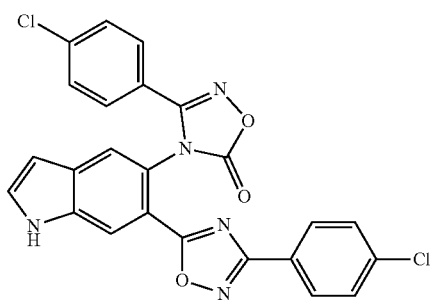 [SMILES: O=c1onc(-c2ccc(Cl)cc2)n1-c1cc2cc[nH]c2cc1-c1nc(-c2ccc(Cl)cc2)no1] | 3-(4-chlorophenyl)-4-(6-(3-(4-chlorophenyl)-1,2,4-oxadiazol-5-yl)-1H-indol-5-yl)-1,2,4-oxadiazol-5(4H)-one |
| KJA-46 | 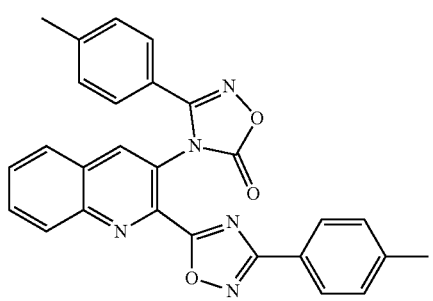 [SMILES: Cc1ccc(-c2noc(-c3nc4ccccc4cc3-n3c(-c4ccc(C)cc4)noc3=O)n2)cc1] | 3-(p-tolyl)-4-(2-(3-(p-tolyl)-1,2,4-oxadiazol-5-yl)quinolin-3-yl)-1,2,4-oxadiazol-5(4H)-one |

-continued
| | | |
|---|---|---|
| KJA-47 | 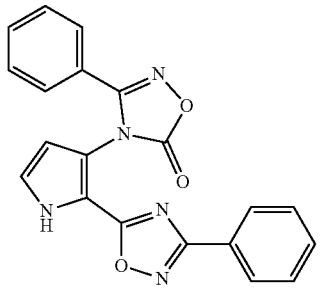 [SMILES: O=c1onc(-c2ccccc2)n1-c1cc[nH]c1-c1nc(-c2ccccc2)no1] | 3-phenyl-4-(2-(3-phenyl-1,2,4-oxadiazol-5-yl)-1H-pyrrol-3-yl)-1,2,4-oxadiazol-5(4H)-one |
| KJA-62 | 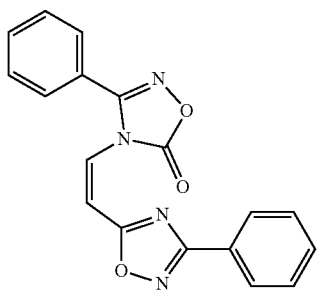 [SMILES: O=c1onc(-c2ccccc2)n1/C=C\c1nc(-c2ccccc2)no1] | (Z)-3-phenyl-4-(2-(3-phenyl-1,2,4-oxadiazol-5-yl)vinyl)-1,2,4-oxadiazol-5(4H)-one |
| KJA-63 | 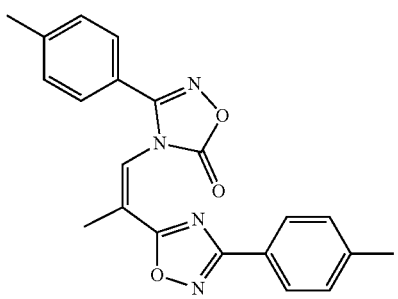 | (Z)-3-(p-tolyl)-4-(2-(3-(p-tolyl)-1,2,4-oxadiazol-5-yl)prop-1-en-1-yl)-1,2,4-oxadiazol-5(4H)-one |
| KJA-64 | 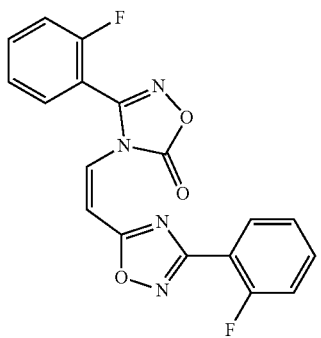 [SMILES: O=c1onc(-c2ccccc2F)n1/C=C\c1nc(-c2ccccc2F)no1]<br>and | (Z)-3-(2-fluorophenyl)-4-(2-(3-(2-fluorophenyl)-1,2,4-oxadiazol-5-yl)vinyl)-1,2,4-oxadiazol-5(4H)-one |
| KJA-65 | 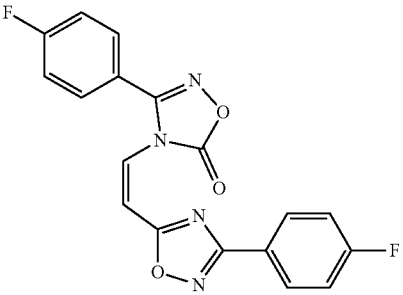 [SMILES: O=c1onc(-c2ccc(F)cc2)n1/C=C\c1nc(-c2ccc(F)cc2)no1] | (Z)-3-(4-fluorophenyl)-4-(2-(3-(4-fluorophenyl)-1,2,4-oxadiazol-5-yl)vinyl)-1,2,4-oxadiazol-5(4H)-one. |

3. A pharmaceutical composition comprising a compound of claim 1.

4. A method of treating, ameliorating, or preventing a hyperproliferative disease and/or condition related to MCL activity in a patient comprising administering to said patient a therapeutically effective amount of the pharmaceutical composition of claim 3.

5. The method of claim 4, wherein the hyperproliferative disease and/or condition is one or more of leukemia, non-small cell lung cancer, colon cancer, CNS cancer, melanoma, ovarian cancer, breast cancer, renal cancer, prostate cancer, age-related macular degeneration, macular dystrophy, and diabetes.

6. The method of claim 4, wherein said patient is a human patient.

7. The method of claim 4 further comprising administering to said patient one or more anticancer agents.

8. The method of claim 7 wherein said anticancer agent is a chemotherapeutic agent.

9. The method of claim 7 wherein said anticancer agent is radiation therapy.

10. A kit comprising a compound of claim 1 and instructions for administering said compound to a patient having a hyperproliferative disease and/or condition related to MCL activity.

11. The kit of claim 10, wherein the hyperproliferative disease and/or condition is one or more of leukemia, non-small cell lung cancer, colon cancer, CNS cancer, melanoma, ovarian cancer, breast cancer, renal cancer, prostate cancer, age-related macular degeneration, macular dystrophy, and diabetes.

12. The kit of claim 10 further comprising one or more anticancer agents.

13. The kit of claim 12, wherein said compound is to be administered together with one or more anticancer agents.

* * * * *